(12) United States Patent
Fraden et al.

(10) Patent No.: US 8,772,046 B2
(45) Date of Patent: Jul. 8, 2014

(54) MANIPULATION OF FLUIDS AND REACTIONS IN MICROFLUIDIC SYSTEMS

(75) Inventors: Seth Fraden, Newton, MA (US); Galder Cristobal-Azkarate, Bordeaux (FR)

(73) Assignee: Brandeis University, Waltham, MA (US)

( * ) Notice: Subject to any disclaimer, the term of this patent is extended or adjusted under 35 U.S.C. 154(b) by 1092 days.

(21) Appl. No.: 12/525,749

(22) PCT Filed: Feb. 6, 2008

(86) PCT No.: PCT/US2008/001544
§ 371 (c)(1),
(2), (4) Date: Mar. 9, 2010

(87) PCT Pub. No.: WO2008/097559
PCT Pub. Date: Aug. 14, 2008

(65) Prior Publication Data
US 2010/0163109 A1    Jul. 1, 2010

Related U.S. Application Data

(60) Provisional application No. 60/899,849, filed on Feb. 6, 2007.

(51) Int. Cl.
*G01N 1/38* (2006.01)
*B01L 3/00* (2006.01)

(52) U.S. Cl.
CPC ............. *G01N 1/38* (2013.01); *B01L 3/5027* (2013.01); *G01N 2001/386* (2013.01)
USPC .......................................... 436/180; 422/502

(58) Field of Classification Search
CPC ... G01N 1/38; G01N 2001/386; B01L 3/5027
USPC .................. 422/502, 503; 137/2, 14; 436/180
See application file for complete search history.

(56) References Cited

U.S. PATENT DOCUMENTS 2,097,692 A   11/1937   Fiegel
2,164,172 A    6/1939   Dalton
(Continued)

FOREIGN PATENT DOCUMENTS

AU    2004225691 B2   10/2004
CA       2520548 A1    9/2004
(Continued)

OTHER PUBLICATIONS

Adang, A.E. et al., The contribution of combinatorial chemistry to lead generation: an interim analysis, Curr Med Chem 8: 985-998 (2001).

(Continued)

*Primary Examiner* — Paul Hyun
(74) *Attorney, Agent, or Firm* — Thomas C. Meyers; Brown Rudnick LLP

(57) ABSTRACT

Microfluidic structures and methods for manipulating fluids and reactions are provided. Such structures and methods may involve positioning fluid samples, e.g., in the form of droplets, in a carrier fluid (e.g., an oil, which may be immiscible with the fluid sample) in predetermined regions in a microfluidic network. In some embodiments, positioning of the droplets can take place in the order in which they are introduced into the microfluidic network (e.g., sequentially) without significant physical contact between the droplets. Because of the little or no contact between the droplets, there may be little or no coalescence between the droplets. Accordingly, in some such embodiments, surfactants are not required in either the fluid sample or the carrier fluid to prevent coalescence of the droplets. Structures and methods described herein also enable droplets to be removed sequentially from the predetermined regions.

25 Claims, 18 Drawing Sheets

(56) References Cited

U.S. PATENT DOCUMENTS

| | | |
|---|---|---|
| 2,656,508 A | 10/1953 | Coulter |
| 2,692,800 A | 10/1954 | Nichols et al. |
| 2,797,149 A | 6/1957 | Skeggs |
| 2,879,141 A | 3/1959 | Skeggs |
| 2,971,700 A | 2/1961 | Peeps |
| 3,479,141 A | 11/1969 | Smythe et al. |
| 3,608,821 A | 9/1971 | Simm et al. |
| 3,698,635 A | 10/1972 | Sickles |
| 3,816,331 A | 6/1974 | Brown, Jr. et al. |
| 3,930,061 A | 12/1975 | Scharfenberger |
| 3,960,187 A | 6/1976 | Stock et al. |
| 3,980,541 A | 9/1976 | Aine |
| 3,982,541 A | 9/1976 | L'Esperance, Jr. |
| 4,014,469 A | 3/1977 | Sato |
| 4,022,575 A | 5/1977 | Hansen et al. |
| 4,034,966 A | 7/1977 | Suh et al. |
| 4,059,552 A | 11/1977 | Zweigle et al. |
| 4,091,042 A | 5/1978 | Alexanderson et al. |
| 4,117,550 A | 9/1978 | Folland et al. |
| 4,130,394 A | 12/1978 | Negersmith |
| 4,210,809 A | 7/1980 | Pelavin |
| 4,253,846 A | 3/1981 | Smythe et al. |
| 4,266,721 A | 5/1981 | Sickles |
| 4,279,345 A | 7/1981 | Allred |
| 4,297,345 A | 10/1981 | Howarth |
| 4,315,754 A | 2/1982 | Ruzicka et al. |
| 4,378,957 A | 4/1983 | Malkin et al. |
| 4,383,767 A | 5/1983 | Jido |
| 4,439,980 A | 4/1984 | Biblarz et al. |
| 4,508,265 A | 4/1985 | Jido |
| 4,533,634 A | 8/1985 | Maldonado et al. |
| 4,585,209 A | 4/1986 | Aine et al. |
| 4,618,476 A | 10/1986 | Columbus |
| 4,628,040 A | 12/1986 | Green |
| 4,675,285 A | 6/1987 | Clark et al. |
| 4,676,274 A | 6/1987 | Brown |
| 4,683,195 A | 7/1987 | Mullis et al. |
| 4,683,202 A | 7/1987 | Mullis |
| 4,739,044 A | 4/1988 | Stabinsky |
| 4,757,141 A | 7/1988 | Fung et al. |
| 4,767,515 A | 8/1988 | Scott et al. |
| 4,767,929 A | 8/1988 | Valentine |
| 4,779,805 A | 10/1988 | Jackson et al. |
| 4,801,086 A | 1/1989 | Noakes |
| 4,801,529 A | 1/1989 | Perlman |
| 4,829,996 A | 5/1989 | Noakes et al. |
| 4,853,336 A | 8/1989 | Saros et al. |
| 4,865,444 A | 9/1989 | Green et al. |
| 4,883,750 A | 11/1989 | Whiteley et al. |
| 4,908,112 A | 3/1990 | Pace |
| 4,931,225 A | 6/1990 | Cheng |
| 4,941,959 A | 7/1990 | Scott |
| 4,962,885 A | 10/1990 | Coffee |
| 4,963,498 A | 10/1990 | Hillman et al. |
| 4,981,580 A | 1/1991 | Auer |
| 4,996,004 A | 2/1991 | Bucheler et al. |
| 5,091,652 A | 2/1992 | Mathies et al. |
| 5,096,615 A | 3/1992 | Prescott et al. |
| 5,122,360 A | 6/1992 | Harris et al. |
| 5,180,662 A | 1/1993 | Sitkovsky |
| 5,185,099 A | 2/1993 | Delpuech et al. |
| 5,188,290 A | 2/1993 | Gebauer et al. |
| 5,188,291 A | 2/1993 | Cross |
| 5,204,112 A | 4/1993 | Hope et al. |
| 5,207,973 A | 5/1993 | Harris et al. |
| 5,241,159 A | 8/1993 | Chatteriee et al. |
| 5,260,466 A | 11/1993 | McGibbon |
| 5,262,027 A | 11/1993 | Scott |
| 5,270,163 A | 12/1993 | Gold et al. |
| 5,296,375 A | 3/1994 | Kricka et al. |
| 5,304,487 A | 4/1994 | Wilding et al. |
| 5,310,653 A | 5/1994 | Hanausek-Walaszek et al. |
| 5,313,009 A | 5/1994 | Guenkel et al. |
| 5,344,594 A | 9/1994 | Sheridon |
| 5,378,957 A | 1/1995 | Kelly |
| 5,397,605 A | 3/1995 | Barbieri et al. |
| 5,399,461 A | 3/1995 | Van et al. |
| 5,399,491 A | 3/1995 | Kacian et al. |
| 5,403,617 A | 4/1995 | Haaland |
| 5,413,924 A | 5/1995 | Kosak et al. |
| 5,417,235 A | 5/1995 | Wise et al. |
| 5,427,946 A | 6/1995 | Kricka et al. |
| 5,445,934 A | 8/1995 | Fodor et al. |
| 5,452,878 A | 9/1995 | Gravesen et al. |
| 5,452,955 A | 9/1995 | Lundstrom |
| 5,454,472 A | 10/1995 | Benecke et al. |
| 5,460,945 A | 10/1995 | Springer et al. |
| 5,475,096 A | 12/1995 | Gold et al. |
| 5,480,614 A | 1/1996 | Kamahori |
| 5,486,335 A | 1/1996 | Wilding et al. |
| 5,498,392 A | 3/1996 | Wilding et al. |
| 5,500,415 A | 3/1996 | Dollat et al. |
| 5,503,851 A | 4/1996 | Mank et al. |
| 5,512,131 A | 4/1996 | Kumar et al. |
| 5,516,635 A | 5/1996 | Ekins et al. |
| 5,518,709 A | 5/1996 | Sutton et al. |
| 5,523,162 A | 6/1996 | Franz et al. |
| 5,587,128 A | 12/1996 | Wilding et al. |
| 5,604,097 A | 2/1997 | Brenner |
| 5,612,188 A | 3/1997 | Shuler et al. |
| 5,616,478 A | 4/1997 | Chetverin et al. |
| 5,617,997 A | 4/1997 | Kobayashi et al. |
| 5,635,358 A | 6/1997 | Wilding et al. |
| 5,636,400 A | 6/1997 | Young |
| 5,641,658 A | 6/1997 | Adams et al. |
| 5,643,729 A | 7/1997 | Taniguchi et al. |
| 5,655,517 A | 8/1997 | Coffee |
| 5,656,155 A | 8/1997 | Norcross et al. |
| 5,661,222 A | 8/1997 | Hare |
| 5,662,874 A | 9/1997 | David |
| 5,670,325 A | 9/1997 | Lapidus et al. |
| 5,681,600 A | 10/1997 | Antinone et al. |
| 5,695,934 A | 12/1997 | Brenner |
| 5,726,026 A | 3/1998 | Wilding et al. |
| 5,726,404 A | 3/1998 | Brody |
| 5,733,526 A | 3/1998 | Trevino et al. |
| 5,739,036 A | 4/1998 | Parris |
| 5,744,366 A | 4/1998 | Kricka et al. |
| 5,750,988 A | 5/1998 | Apffel et al. |
| 5,762,775 A | 6/1998 | DePaoli et al. |
| 5,779,868 A | 7/1998 | Parce et al. |
| 5,783,431 A | 7/1998 | Peterson et al. |
| 5,840,506 A | 11/1998 | Giordano |
| 5,846,719 A | 12/1998 | Brenner et al. |
| 5,849,491 A | 12/1998 | Radomski et al. |
| 5,858,187 A | 1/1999 | Ramsey et al. |
| 5,858,655 A | 1/1999 | Arnold |
| 5,858,670 A | 1/1999 | Lam et al. |
| 5,863,722 A | 1/1999 | Brenner |
| 5,868,322 A | 2/1999 | Loucks, Jr. et al. |
| 5,872,010 A | 2/1999 | Karger et al. |
| 5,876,771 A | 3/1999 | Sizer et al. |
| 5,880,071 A | 3/1999 | Parce et al. |
| 5,882,680 A | 3/1999 | Suzuki et al. |
| 5,884,846 A | 3/1999 | Tan |
| 5,887,755 A | 3/1999 | Hood, III |
| 5,888,746 A | 3/1999 | Tabiti et al. |
| 5,888,778 A | 3/1999 | Shuber |
| 5,904,933 A | 5/1999 | Riess et al. |
| 5,921,678 A | 7/1999 | Desai et al. |
| 5,927,852 A | 7/1999 | Serafin |
| 5,928,870 A | 7/1999 | Lapidus et al. |
| 5,932,100 A | 8/1999 | Yager et al. |
| 5,935,331 A | 8/1999 | Naka et al. |
| 5,942,056 A | 8/1999 | Singh |
| 5,942,443 A | 8/1999 | Parce et al. |
| 5,958,203 A | 9/1999 | Parce et al. |
| 5,972,187 A | 10/1999 | Parce et al. |
| 5,980,936 A | 11/1999 | Krafft et al. |
| 5,989,815 A | 11/1999 | Skolnick et al. |
| 5,989,892 A | 11/1999 | Nishimaki et al. |
| 5,995,341 A | 11/1999 | Tanaka et al. |
| 5,997,636 A | 12/1999 | Gamarnik et al. |
| 6,008,003 A | 12/1999 | Haak-Frendscho et al. |

(56) References Cited

U.S. PATENT DOCUMENTS

| | | |
|---|---|---|
| 6,023,540 A | 2/2000 | Walt et al. |
| 6,028,066 A | 2/2000 | Unger |
| 6,042,709 A | 3/2000 | Parce et al. |
| 6,045,755 A | 4/2000 | Lebl et al. |
| 6,046,056 A | 4/2000 | Parce et al. |
| 6,048,551 A | 4/2000 | Hilfinger et al. |
| 6,068,199 A | 5/2000 | Coffee |
| 6,080,295 A | 6/2000 | Parce et al. |
| 6,086,740 A | 7/2000 | Kennedy |
| 6,096,495 A | 8/2000 | Kasai et al. |
| 6,103,537 A | 8/2000 | Ullman et al. |
| 6,105,571 A | 8/2000 | Coffee |
| 6,105,877 A | 8/2000 | Coffee |
| 6,116,516 A | 9/2000 | Ganan-Calvo |
| 6,118,849 A | 9/2000 | Tanimori et al. |
| 6,119,953 A | 9/2000 | Ganan-Calvo et al. |
| 6,120,666 A | 9/2000 | Jacobson et al. |
| 6,124,388 A | 9/2000 | Takai et al. |
| 6,124,439 A | 9/2000 | Friedman et al. |
| 6,130,052 A | 10/2000 | Van Baren et al. |
| 6,130,098 A | 10/2000 | Handique et al. |
| 6,137,214 A | 10/2000 | Raina |
| 6,138,077 A | 10/2000 | Brenner |
| 6,139,303 A | 10/2000 | Reed et al. |
| 6,140,053 A | 10/2000 | Koster |
| 6,143,496 A | 11/2000 | Brown et al. |
| 6,149,789 A | 11/2000 | Benecke et al. |
| 6,150,180 A | 11/2000 | Parce et al. |
| 6,150,516 A | 11/2000 | Brenner et al. |
| 6,165,778 A | 12/2000 | Kedar |
| 6,171,796 B1 | 1/2001 | An et al. |
| 6,171,850 B1 | 1/2001 | Nagle et al. |
| 6,172,214 B1 | 1/2001 | Brenner |
| 6,172,218 B1 | 1/2001 | Brenner |
| 6,174,160 B1 | 1/2001 | Lee et al. |
| 6,174,469 B1 | 1/2001 | Ganan-Calvo |
| 6,180,372 B1 | 1/2001 | Franzen |
| 6,184,012 B1 | 2/2001 | Neri et al. |
| 6,187,214 B1 | 2/2001 | Ganan-Calvo |
| 6,189,803 B1 | 2/2001 | Ganan-Calvo |
| 6,196,525 B1 | 3/2001 | Ganan-Calvo |
| 6,197,335 B1 | 3/2001 | Sherman |
| 6,197,835 B1 | 3/2001 | Ganan-Calvo |
| 6,203,993 B1 | 3/2001 | Shuber et al. |
| 6,210,396 B1 | 4/2001 | MacDonald et al. |
| 6,210,891 B1 | 4/2001 | Nyren et al. |
| 6,210,896 B1 | 4/2001 | Chan |
| 6,214,558 B1 | 4/2001 | Shuber et al. |
| 6,221,654 B1 | 4/2001 | Quake et al. |
| 6,227,466 B1 | 5/2001 | Hartman et al. |
| 6,234,402 B1 | 5/2001 | Ganan-Calvo |
| 6,235,383 B1 | 5/2001 | Hong et al. |
| 6,235,475 B1 | 5/2001 | Brenner et al. |
| 6,241,159 B1 | 6/2001 | Ganan-Calvo et al. |
| 6,243,373 B1 | 6/2001 | Turock |
| 6,248,378 B1 | 6/2001 | Ganan-Calvo |
| 6,251,661 B1 | 6/2001 | Urabe et al. |
| 6,252,129 B1 | 6/2001 | Coffee |
| 6,258,568 B1 | 7/2001 | Nyren |
| 6,258,858 B1 | 7/2001 | Nakajima et al. |
| 6,263,222 B1 | 7/2001 | Diab et al. |
| 6,266,459 B1 | 7/2001 | Walt et al. |
| 6,267,353 B1 | 7/2001 | Friedline et al. |
| 6,267,858 B1 | 7/2001 | Parce et al. |
| 6,268,165 B1 | 7/2001 | O'Brien |
| 6,268,222 B1 | 7/2001 | Chandler et al. |
| 6,274,320 B1 | 8/2001 | Rothberg et al. |
| 6,274,337 B1 | 8/2001 | Parce et al. |
| 6,294,344 B1 | 9/2001 | O'Brien |
| 6,296,673 B1 | 10/2001 | Santarsiero et al. |
| 6,299,145 B1 | 10/2001 | Ganan-Calvo |
| 6,301,055 B1 | 10/2001 | Legrand et al. |
| 6,306,659 B1 | 10/2001 | Parce et al. |
| 6,310,354 B1 | 10/2001 | Hanninen et al. |
| 6,310,653 B1 | 10/2001 | Malcolm, Jr. et al. |
| 6,316,208 B1 | 11/2001 | Roberts et al. |
| 6,316,213 B1 | 11/2001 | O'Brien |
| 6,318,640 B1 | 11/2001 | Coffee |
| 6,336,463 B1 | 1/2002 | Ohta |
| 6,344,325 B1 | 2/2002 | Quake et al. |
| 6,352,828 B1 | 3/2002 | Brenner |
| 6,355,193 B1 | 3/2002 | Stott |
| 6,355,198 B1 | 3/2002 | Kim et al. |
| 6,357,670 B2 | 3/2002 | Ganan-Calvo |
| 6,386,463 B1 | 5/2002 | Ganan-Calvo |
| 6,391,559 B1 | 5/2002 | Brown et al. |
| 6,394,429 B2 | 5/2002 | Ganan-Calvo |
| 6,399,339 B1 | 6/2002 | Wolberg et al. |
| 6,399,389 B1 | 6/2002 | Parce et al. |
| 6,403,373 B1 | 6/2002 | Scanlan et al. |
| 6,405,936 B1 | 6/2002 | Ganan-Calvo |
| 6,408,878 B2 | 6/2002 | Unger et al. |
| 6,409,832 B2 | 6/2002 | Weigl et al. |
| 6,429,025 B1 | 8/2002 | Parce et al. |
| 6,429,148 B1 | 8/2002 | Chu et al. |
| 6,432,143 B2 | 8/2002 | Kubiak et al. |
| 6,432,148 B1 | 8/2002 | Ganan-Calvo |
| 6,432,630 B1 | 8/2002 | Blankenstein |
| 6,439,103 B1 | 8/2002 | Miller |
| 6,440,706 B1 | 8/2002 | Vogelstein et al. |
| 6,450,139 B1 | 9/2002 | Watanabe |
| 6,450,189 B1 | 9/2002 | Ganan-Calvo |
| 6,454,193 B1 | 9/2002 | Busick et al. |
| 6,464,336 B1 | 10/2002 | Sharma |
| 6,464,886 B2 | 10/2002 | Ganan-Calvo |
| 6,475,441 B1 | 11/2002 | Parce et al. |
| 6,481,648 B1 | 11/2002 | Zimmermann |
| 6,489,103 B1 | 12/2002 | Griffiths et al. |
| 6,503,933 B1 | 1/2003 | Moloney et al. |
| 6,506,609 B1 | 1/2003 | Wada et al. |
| 6,508,988 B1 | 1/2003 | Van Dam et al. |
| 6,520,425 B1 | 2/2003 | Reneker |
| 6,524,456 B1 | 2/2003 | Ramsey et al. |
| 6,540,395 B2 | 4/2003 | Muhlbauer et al. |
| 6,540,895 B1 | 4/2003 | Spence et al. |
| 6,551,836 B1 | 4/2003 | Chow et al. |
| 6,553,944 B1 | 4/2003 | Allen et al. |
| 6,553,960 B1 | 4/2003 | Yoshikawa et al. |
| 6,554,202 B2 | 4/2003 | Ganan-Calvo |
| 6,557,334 B2 | 5/2003 | Jager |
| 6,557,834 B2 | 5/2003 | Ganan-Calvo |
| 6,558,944 B1 | 5/2003 | Parce et al. |
| 6,558,960 B1 | 5/2003 | Parce et al. |
| 6,560,030 B2 | 5/2003 | Legrand et al. |
| 6,565,010 B2 | 5/2003 | Anderson et al. |
| 6,569,631 B1 | 5/2003 | Pantoliano et al. |
| 6,576,420 B1 | 6/2003 | Carson et al. |
| 6,591,852 B1 * | 7/2003 | McNeely et al. ............... 137/14 |
| 6,592,321 B2 | 7/2003 | Bonker et al. |
| 6,592,821 B1 | 7/2003 | Wada et al. |
| 6,608,726 B2 | 8/2003 | Legrand et al. |
| 6,610,499 B1 | 8/2003 | Fulwyler et al. |
| 6,614,598 B1 | 9/2003 | Quake et al. |
| 6,627,603 B1 | 9/2003 | Bibette et al. |
| 6,630,006 B2 | 10/2003 | Santarsiero et al. |
| 6,630,353 B1 | 10/2003 | Parce et al. |
| 6,632,619 B1 | 10/2003 | Harrison et al. |
| 6,638,749 B1 | 10/2003 | Beckman et al. |
| 6,645,432 B1 | 11/2003 | Anderson et al. |
| 6,646,253 B1 | 11/2003 | Rohwer et al. |
| 6,653,626 B2 | 11/2003 | Fischer et al. |
| 6,656,267 B2 | 12/2003 | Newman |
| 6,659,370 B1 | 12/2003 | Inoue |
| 6,660,252 B2 | 12/2003 | Matathia et al. |
| 6,670,142 B2 | 12/2003 | Lau et al. |
| 6,679,441 B1 | 1/2004 | Borra et al. |
| 6,680,178 B1 | 1/2004 | Harris et al. |
| 6,682,890 B2 | 1/2004 | Mack et al. |
| 6,717,136 B2 | 4/2004 | Andersson et al. |
| 6,729,561 B2 | 5/2004 | Hirae et al. |
| 6,739,036 B2 | 5/2004 | Koike et al. |
| 6,744,046 B2 | 6/2004 | Valaskovic et al. |
| 6,752,922 B2 | 6/2004 | Huang et al. |
| 6,753,147 B2 | 6/2004 | Vogelstein et al. |

(56) References Cited

U.S. PATENT DOCUMENTS

| | | |
|---|---|---|
| 6,766,817 B2 | 7/2004 | da Silva |
| 6,767,194 B2 | 7/2004 | Jeon et al. |
| 6,767,704 B2 | 7/2004 | Waldman et al. |
| 6,790,328 B2 | 9/2004 | Jacobson et al. |
| 6,793,753 B2 | 9/2004 | Unger et al. |
| 6,797,056 B2 | 9/2004 | David |
| 6,800,849 B2 | 10/2004 | Staats |
| 6,806,058 B2 | 10/2004 | Jesperson et al. |
| 6,808,382 B2 | 10/2004 | Lanfranchi |
| 6,808,882 B2 | 10/2004 | Griffiths et al. |
| 6,814,980 B2 | 11/2004 | Levy et al. |
| 6,818,395 B1 | 11/2004 | Quake et al. |
| 6,832,787 B1 | 12/2004 | Renzi |
| 6,833,242 B2 | 12/2004 | Quake et al. |
| 6,841,350 B2 | 1/2005 | Ogden et al. |
| 6,872,250 B2 | 3/2005 | David et al. |
| 6,890,487 B1 | 5/2005 | Sklar et al. |
| 6,897,018 B1 | 5/2005 | Yuan et al. |
| 6,905,844 B2 | 6/2005 | Kim |
| 6,918,404 B2 | 7/2005 | Dias da Silva |
| 6,926,313 B1 | 8/2005 | Renzi |
| 6,935,768 B2 | 8/2005 | Lowe et al. |
| 6,936,417 B2 | 8/2005 | Orntoft |
| 6,942,978 B1 | 9/2005 | O'Brien |
| 6,949,342 B2 | 9/2005 | Golub et al. |
| 6,960,437 B2 | 11/2005 | Enzelberger et al. |
| 6,974,667 B2 | 12/2005 | Horne et al. |
| 6,998,232 B1 | 2/2006 | Feinstein et al. |
| 7,022,472 B2 | 4/2006 | Robbins et al. |
| 7,041,481 B2 | 5/2006 | Anderson et al. |
| 7,049,072 B2 | 5/2006 | Seshi |
| 7,056,674 B2 | 6/2006 | Baker et al. |
| 7,057,026 B2 | 6/2006 | Barnes et al. |
| 7,066,586 B2 | 6/2006 | da Silva |
| 7,068,874 B2 | 6/2006 | Wang et al. |
| 7,078,180 B2 | 7/2006 | Genetta |
| 7,081,192 B1 | 7/2006 | Wang et al. |
| 7,081,340 B2 | 7/2006 | Baker et al. |
| 7,090,983 B1 | 8/2006 | Muramatsu et al. |
| 7,115,230 B2 | 10/2006 | Sundararajan et al. |
| 7,118,910 B2 | 10/2006 | Unger et al. |
| 7,129,091 B2 | 10/2006 | Ismagilov et al. |
| 7,138,233 B2 | 11/2006 | Griffiths et al. |
| 7,153,700 B1 | 12/2006 | Pardee et al. |
| 7,156,917 B2 | 1/2007 | Moriyama et al. |
| 7,163,801 B2 | 1/2007 | Reed |
| 7,169,560 B2 | 1/2007 | Lapidus et al. |
| 7,171,311 B2 | 1/2007 | Dai et al. |
| 7,198,899 B2 | 4/2007 | Schleyer et al. |
| 7,204,431 B2 | 4/2007 | Li et al. |
| 7,229,770 B1 | 6/2007 | Price et al. |
| 7,252,943 B2 | 8/2007 | Griffiths et al. |
| 7,267,938 B2 | 9/2007 | Anderson et al. |
| 7,268,167 B2 | 9/2007 | Higuchi et al. |
| 7,282,337 B1 | 10/2007 | Harris |
| 7,291,462 B2 | 11/2007 | O'Brien et al. |
| 7,294,503 B2 | 11/2007 | Quake et al. |
| 7,300,765 B2 | 11/2007 | Patel |
| 7,308,364 B2 | 12/2007 | Shaughnessy et al. |
| 7,314,721 B2 | 1/2008 | Gure et al. |
| 7,316,906 B2 | 1/2008 | Chiorazzi et al. |
| 7,326,529 B2 | 2/2008 | Ali et al. |
| 7,332,280 B2 | 2/2008 | Levy et al. |
| 7,332,590 B2 | 2/2008 | Nacht et al. |
| 7,341,211 B2 | 3/2008 | Ganan Calvo et al. |
| 7,348,142 B2 | 3/2008 | Wang |
| 7,358,231 B1 | 4/2008 | McCaffey et al. |
| 7,361,474 B2 | 4/2008 | Siegler |
| 7,364,862 B2 | 4/2008 | Ali et al. |
| 7,368,255 B2 | 5/2008 | Bae et al. |
| 7,378,233 B2 | 5/2008 | Sidransky et al. |
| 7,378,280 B2 | 5/2008 | Quake et al. |
| 7,390,463 B2 | 6/2008 | He et al. |
| 7,393,665 B2 | 7/2008 | Brenner |
| 7,416,851 B2 | 8/2008 | Davi et al. |
| 7,429,467 B2 | 9/2008 | Holliger et al. |
| 7,432,064 B2 | 10/2008 | Salceda et al. |
| 7,442,507 B2 | 10/2008 | Polsky et al. |
| 7,449,303 B2 | 11/2008 | Coignet |
| 7,468,271 B2 | 12/2008 | Golovchenko et al. |
| 7,473,530 B2 | 1/2009 | Huttemann |
| 7,473,531 B1 | 1/2009 | Domon et al. |
| 7,476,506 B2 | 1/2009 | Schleyer et al. |
| 7,479,370 B2 | 1/2009 | Coignet |
| 7,479,371 B2 | 1/2009 | Ando et al. |
| 7,479,376 B2 | 1/2009 | Waldman et al. |
| 7,482,129 B2 | 1/2009 | Soyupak et al. |
| 7,501,244 B2 | 3/2009 | Reinhard et al. |
| 7,504,214 B2 | 3/2009 | Erlander et al. |
| 7,507,532 B2 | 3/2009 | Chang et al. |
| 7,507,541 B2 | 3/2009 | Raitano et al. |
| 7,510,707 B2 | 3/2009 | Platica et al. |
| 7,510,842 B2 | 3/2009 | Podust et al. |
| 7,514,209 B2 | 4/2009 | Dai et al. |
| 7,514,210 B2 | 4/2009 | Holliger et al. |
| 7,524,633 B2 | 4/2009 | Sidransky |
| 7,527,933 B2 | 5/2009 | Sahin et al. |
| 7,537,897 B2 | 5/2009 | Brenner et al. |
| 7,541,383 B2 | 6/2009 | Fu et al. |
| 7,544,473 B2 | 6/2009 | Brenner |
| 7,556,776 B2 | 7/2009 | Fraden et al. |
| 7,582,446 B2 | 9/2009 | Griffiths et al. |
| 7,622,081 B2 | 11/2009 | Chou et al. |
| 7,632,562 B2 | 12/2009 | Nair et al. |
| 7,635,562 B2 | 12/2009 | Harris et al. |
| 7,638,276 B2 | 12/2009 | Griffiths et al. |
| 7,655,435 B2 | 2/2010 | Holliger et al. |
| 7,655,470 B2 | 2/2010 | Ismagilov et al. |
| 7,666,593 B2 | 2/2010 | Lapidus |
| 7,678,565 B2 | 3/2010 | Schurmann-Mader |
| 7,691,576 B2 | 4/2010 | Holliger et al. |
| 7,698,287 B2 | 4/2010 | Becker et al. |
| 7,708,949 B2 | 5/2010 | Stone et al. |
| 7,718,578 B2 | 5/2010 | Griffiths et al. |
| 7,736,890 B2 | 6/2010 | Sia et al. |
| 7,741,130 B2 | 6/2010 | Lee, Jr. et al. |
| 7,814,175 B1 | 10/2010 | Chang et al. |
| 7,824,889 B2 | 11/2010 | Vogelstein et al. |
| 7,897,044 B2 | 3/2011 | Hoyos et al. |
| 7,897,341 B2 | 3/2011 | Griffiths et al. |
| 7,901,939 B2 | 3/2011 | Ismagilov et al. |
| 7,968,287 B2 | 6/2011 | Griffiths et al. |
| 8,012,382 B2 | 9/2011 | Kim et al. |
| 8,153,402 B2 | 4/2012 | Holliger et al. |
| 2001/0010338 A1 | 8/2001 | Ganan-Calvo |
| 2001/0020011 A1 | 9/2001 | Mathiowitz et al. |
| 2001/0023078 A1 | 9/2001 | Bawendi et al. |
| 2001/0029983 A1 | 10/2001 | Unger et al. |
| 2001/0034031 A1 | 10/2001 | Short et al. |
| 2001/0041343 A1 | 11/2001 | Pankowsky |
| 2001/0041344 A1 | 11/2001 | Sepetov et al. |
| 2001/0042793 A1 | 11/2001 | Ganan-Calvo |
| 2001/0048900 A1 | 12/2001 | Bardell et al. |
| 2001/0050881 A1 | 12/2001 | Depaoli et al. |
| 2002/0004532 A1 | 1/2002 | Matathia et al. |
| 2002/0005354 A1 | 1/2002 | Spence et al. |
| 2002/0008028 A1 | 1/2002 | Jacobson et al. |
| 2002/0012971 A1 | 1/2002 | Mehta |
| 2002/0022038 A1 | 2/2002 | Biatry et al. |
| 2002/0022261 A1 | 2/2002 | Anderson et al. |
| 2002/0033422 A1 | 3/2002 | Ganan-Calvo |
| 2002/0036139 A1 | 3/2002 | Becker et al. |
| 2002/0058332 A1* | 5/2002 | Quake et al. ............... 435/288.3 |
| 2002/0067800 A1 | 6/2002 | Newman et al. |
| 2002/0119459 A1 | 8/2002 | Griffiths |
| 2002/0143437 A1* | 10/2002 | Handique et al. ............ 700/266 |
| 2002/0155080 A1 | 10/2002 | Glenn et al. |
| 2002/0158027 A1 | 10/2002 | Moon et al. |
| 2002/0164271 A1 | 11/2002 | Ho |
| 2002/0164629 A1 | 11/2002 | Quake et al. |
| 2003/0012586 A1 | 1/2003 | Iwata et al. |
| 2003/0015425 A1 | 1/2003 | Bohm et al. |
| 2003/0017579 A1 | 1/2003 | Corn et al. |
| 2003/0039169 A1 | 2/2003 | Ehrfeld et al. |

(56) References Cited

U.S. PATENT DOCUMENTS

| | | |
|---|---|---|
| 2003/0059764 A1 | 3/2003 | Ravkin et al. |
| 2003/0061687 A1 | 4/2003 | Hansen et al. |
| 2003/0064414 A1 | 4/2003 | Benecky et al. |
| 2003/0082795 A1 | 5/2003 | Shuler et al. |
| 2003/0124586 A1 | 7/2003 | Griffiths et al. |
| 2003/0144260 A1 | 7/2003 | Gilon |
| 2003/0148544 A1 | 8/2003 | Nie et al. |
| 2003/0183525 A1 | 10/2003 | Elrod et al. |
| 2003/0224509 A1 | 12/2003 | Moon et al. |
| 2003/0229376 A1 | 12/2003 | Sandhu |
| 2003/0230486 A1 | 12/2003 | Chien et al. |
| 2003/0232356 A1 | 12/2003 | Dooley et al. |
| 2004/0005582 A1 | 1/2004 | Shipwash |
| 2004/0005594 A1 | 1/2004 | Holliger et al. |
| 2004/0018525 A1 | 1/2004 | Wirtz et al. |
| 2004/0027915 A1 | 2/2004 | Lowe et al. |
| 2004/0037813 A1 | 2/2004 | Simpson et al. |
| 2004/0041093 A1 | 3/2004 | Schultz et al. |
| 2004/0050946 A1 | 3/2004 | Wang et al. |
| 2004/0053247 A1 | 3/2004 | Cordon-Cardo et al. |
| 2004/0068019 A1 | 4/2004 | Higuchi et al. |
| 2004/0069632 A1 | 4/2004 | Ripoll |
| 2004/0071781 A1 | 4/2004 | Chattopadhyay et al. |
| 2004/0079881 A1 | 4/2004 | Fischer et al. |
| 2004/0096515 A1 | 5/2004 | Bausch et al. |
| 2004/0115224 A1 | 6/2004 | Ohno |
| 2004/0134854 A1 | 7/2004 | Higuchi |
| 2004/0136497 A1 | 7/2004 | Meldrum et al. |
| 2004/0146921 A1 | 7/2004 | Eveleigh et al. |
| 2004/0159633 A1 | 8/2004 | Whitesides et al. |
| 2004/0181131 A1 | 9/2004 | Maynard et al. |
| 2004/0181343 A1 | 9/2004 | Wigstrom et al. |
| 2004/0182712 A1 | 9/2004 | Basol |
| 2004/0188254 A1 | 9/2004 | Spaid |
| 2004/0224419 A1 | 11/2004 | Zheng et al. |
| 2004/0253731 A1 | 12/2004 | Holliger et al. |
| 2004/0258203 A1 | 12/2004 | Yamano et al. |
| 2005/0032238 A1 | 2/2005 | Karp et al. |
| 2005/0032240 A1 | 2/2005 | Lee et al. |
| 2005/0037392 A1 | 2/2005 | Griffiths et al. |
| 2005/0042648 A1 | 2/2005 | Griffiths et al. |
| 2005/0048467 A1 | 3/2005 | Sastry et al. |
| 2005/0064460 A1 | 3/2005 | Holliger et al. |
| 2005/0069920 A1 | 3/2005 | Griffiths et al. |
| 2005/0079510 A1 | 4/2005 | Berka et al. |
| 2005/0084923 A1 | 4/2005 | Mueller et al. |
| 2005/0087122 A1 | 4/2005 | Ismagliov et al. |
| 2005/0095611 A1 | 5/2005 | Chan et al. |
| 2005/0100895 A1 | 5/2005 | Waldman et al. |
| 2005/0129582 A1 | 6/2005 | Breidford et al. |
| 2005/0152908 A1 | 7/2005 | Liew et al. |
| 2005/0164239 A1 | 7/2005 | Griffiths et al. |
| 2005/0170431 A1 | 8/2005 | Ibrahim et al. |
| 2005/0172476 A1 | 8/2005 | Stone et al. |
| 2005/0183995 A1 | 8/2005 | Deshpande et al. |
| 2005/0207940 A1 | 9/2005 | Butler et al. |
| 2005/0221339 A1 | 10/2005 | Griffiths et al. |
| 2005/0226742 A1 | 10/2005 | Unger et al. |
| 2005/0227264 A1 | 10/2005 | Nobile et al. |
| 2005/0260566 A1 | 11/2005 | Fischer et al. |
| 2005/0272159 A1 | 12/2005 | Ismagilov et al. |
| 2006/0003347 A1 | 1/2006 | Griffiths et al. |
| 2006/0003429 A1 | 1/2006 | Frost et al. |
| 2006/0003439 A1 | 1/2006 | Ismagilov et al. |
| 2006/0036348 A1 | 2/2006 | Handique et al. |
| 2006/0046257 A1 | 3/2006 | Pollock et al. |
| 2006/0051329 A1 | 3/2006 | Lee et al. |
| 2006/0078888 A1 | 4/2006 | Griffiths et al. |
| 2006/0078893 A1 | 4/2006 | Griffiths et al. |
| 2006/0094119 A1 | 5/2006 | Ismagilov et al. |
| 2006/0108012 A1 | 5/2006 | Barrow et al. |
| 2006/0110759 A1 | 5/2006 | Paris et al. |
| 2006/0115821 A1 | 6/2006 | Einstein et al. |
| 2006/0147909 A1 | 7/2006 | Rarbach et al. |
| 2006/0153924 A1 | 7/2006 | Griffiths et al. |
| 2006/0154298 A1 | 7/2006 | Griffiths et al. |
| 2006/0160762 A1 | 7/2006 | Zetter et al. |
| 2006/0163385 A1 | 7/2006 | Link et al. |
| 2006/0169800 A1 | 8/2006 | Rosell et al. |
| 2006/0195269 A1 | 8/2006 | Yeatman et al. |
| 2006/0223127 A1 | 10/2006 | Yip et al. |
| 2006/0234254 A1 | 10/2006 | An et al. |
| 2006/0234259 A1 | 10/2006 | Rubin et al. |
| 2006/0252057 A1 | 11/2006 | Raponi et al. |
| 2006/0258841 A1 | 11/2006 | Michl et al. |
| 2006/0263888 A1 | 11/2006 | Fritz et al. |
| 2006/0269558 A1 | 11/2006 | Murphy et al. |
| 2006/0269971 A1 | 11/2006 | Diamandis |
| 2006/0281089 A1 | 12/2006 | Gibson et al. |
| 2007/0003442 A1 | 1/2007 | Link et al. |
| 2007/0026439 A1 | 2/2007 | Faulstich et al. |
| 2007/0053896 A1 | 3/2007 | Ahmed et al. |
| 2007/0054119 A1 | 3/2007 | Garstecki et al. |
| 2007/0056853 A1 | 3/2007 | Aizenberg et al. |
| 2007/0077572 A1 | 4/2007 | Tawfik et al. |
| 2007/0077579 A1 | 4/2007 | Griffiths et al. |
| 2007/0092914 A1 | 4/2007 | Griffiths et al. |
| 2007/0120899 A1 | 5/2007 | Ohnishi et al. |
| 2007/0154889 A1 | 7/2007 | Wang |
| 2007/0166705 A1 | 7/2007 | Milton et al. |
| 2007/0184439 A1 | 8/2007 | Guilford et al. |
| 2007/0184489 A1 | 8/2007 | Griffiths et al. |
| 2007/0195127 A1 | 8/2007 | Ahn et al. |
| 2007/0259351 A1 | 11/2007 | Chinitz et al. |
| 2007/0259368 A1 | 11/2007 | An et al. |
| 2007/0259374 A1 | 11/2007 | Griffiths et al. |
| 2007/0292869 A1 | 12/2007 | Becker et al. |
| 2008/0003142 A1 | 1/2008 | Link et al. |
| 2008/0009005 A1 | 1/2008 | Kruk |
| 2008/0014589 A1 | 1/2008 | Link et al. |
| 2008/0014590 A1 | 1/2008 | Dahary et al. |
| 2008/0020940 A1 | 1/2008 | Stedronsky et al. |
| 2008/0021330 A1 | 1/2008 | Hwang et al. |
| 2008/0023330 A1 | 1/2008 | Viovy et al. |
| 2008/0038754 A1 | 2/2008 | Farias-Eisner et al. |
| 2008/0044828 A1 | 2/2008 | Kwok |
| 2008/0050378 A1 | 2/2008 | Nakamura et al. |
| 2008/0050723 A1 | 2/2008 | Belacel et al. |
| 2008/0053205 A1 | 3/2008 | Pollack et al. |
| 2008/0057514 A1 | 3/2008 | Goldenring |
| 2008/0058432 A1 | 3/2008 | Wang et al. |
| 2008/0063227 A1 | 3/2008 | Rohrseitz |
| 2008/0064047 A1 | 3/2008 | Zetter et al. |
| 2008/0081330 A1 | 4/2008 | Kahvejian |
| 2008/0081333 A1 | 4/2008 | Mori et al. |
| 2008/0092973 A1 | 4/2008 | Lai |
| 2008/0113340 A1 | 5/2008 | Schlegel |
| 2008/0118462 A1 | 5/2008 | Alani et al. |
| 2008/0138806 A1 | 6/2008 | Chow et al. |
| 2008/0166772 A1 | 7/2008 | Hollinger et al. |
| 2008/0171078 A1 | 7/2008 | Gray |
| 2008/0176211 A1 | 7/2008 | Spence et al. |
| 2008/0176236 A1 | 7/2008 | Tsao et al. |
| 2008/0181850 A1 | 7/2008 | Thaxton et al. |
| 2008/0206756 A1 | 8/2008 | Lee et al. |
| 2008/0222741 A1 | 9/2008 | Chinnaiyan |
| 2008/0234138 A1 | 9/2008 | Shaughnessy et al. |
| 2008/0234139 A1 | 9/2008 | Shaughnessy et al. |
| 2008/0268473 A1 | 10/2008 | Moses et al. |
| 2008/0269157 A1 | 10/2008 | Srivastava et al. |
| 2008/0274908 A1 | 11/2008 | Chang |
| 2008/0280302 A1 | 11/2008 | Kebebew |
| 2008/0286199 A1 | 11/2008 | Livingston et al. |
| 2008/0286801 A1 | 11/2008 | Arjol et al. |
| 2008/0286811 A1 | 11/2008 | Moses et al. |
| 2008/0293578 A1 | 11/2008 | Shaugnessy et al. |
| 2008/0311570 A1 | 12/2008 | Lai |
| 2008/0311604 A1 | 12/2008 | Elting et al. |
| 2009/0004687 A1 | 1/2009 | Mansfield et al. |
| 2009/0005254 A1 | 1/2009 | Griffiths et al. |
| 2009/0012187 A1 | 1/2009 | Chu et al. |
| 2009/0017463 A1 | 1/2009 | Bhowmick |
| 2009/0021728 A1 | 1/2009 | Heinz et al. |
| 2009/0023137 A1 | 1/2009 | Van Der Zee et al. |

(56) References Cited

U.S. PATENT DOCUMENTS

| | | |
|---|---|---|
| 2009/0026082 A1 | 1/2009 | Rothberg et al. |
| 2009/0029372 A1 | 1/2009 | Wewer |
| 2009/0042737 A1 | 2/2009 | Katz et al. |
| 2009/0053700 A1 | 2/2009 | Griffiths et al. |
| 2009/0053732 A1 | 2/2009 | Vermesh et al. |
| 2009/0060797 A1 | 3/2009 | Mathies et al. |
| 2009/0062144 A1 | 3/2009 | Guo |
| 2009/0068170 A1 | 3/2009 | Weitz et al. |
| 2009/0075265 A1 | 3/2009 | Budiman et al. |
| 2009/0075307 A1 | 3/2009 | Fischer et al. |
| 2009/0075311 A1 | 3/2009 | Karl |
| 2009/0081237 A1 | 3/2009 | D'Andrea et al. |
| 2009/0081685 A1 | 3/2009 | Beyer et al. |
| 2009/0087849 A1 | 4/2009 | Malinowski et al. |
| 2009/0092973 A1 | 4/2009 | Erlander et al. |
| 2009/0098542 A1 | 4/2009 | Budiman et al. |
| 2009/0098543 A1 | 4/2009 | Budiman et al. |
| 2009/0118128 A1 | 5/2009 | Liu et al. |
| 2009/0124569 A1 | 5/2009 | Bergan et al. |
| 2009/0127454 A1 | 5/2009 | Ritchie et al. |
| 2009/0127589 A1 | 5/2009 | Rothberg et al. |
| 2009/0131353 A1 | 5/2009 | Insel et al. |
| 2009/0131543 A1 | 5/2009 | Weitz et al. |
| 2009/0191565 A1 | 7/2009 | Lapidus et al. |
| 2009/0197248 A1 | 8/2009 | Griffiths et al. |
| 2009/0197772 A1 | 8/2009 | Griffiths et al. |
| 2009/0246788 A1 | 10/2009 | Albert et al. |
| 2009/0325236 A1 | 12/2009 | Griffiths et al. |
| 2010/0003687 A1 | 1/2010 | Simen et al. |
| 2010/0009353 A1 | 1/2010 | Barnes et al. |
| 2010/0022414 A1 | 1/2010 | Link et al. |
| 2010/0035252 A1 | 2/2010 | Rothberg et al. |
| 2010/0075436 A1 | 3/2010 | Urdea et al. |
| 2010/0105112 A1 | 4/2010 | Holtze et al. |
| 2010/0113768 A1 | 5/2010 | Banerjee et al. |
| 2010/0124759 A1 | 5/2010 | Wang et al. |
| 2010/0136544 A1 | 6/2010 | Agresti et al. |
| 2010/0137143 A1 | 6/2010 | Rothberg et al. |
| 2010/0137163 A1 | 6/2010 | Link et al. |
| 2010/0159592 A1 | 6/2010 | Holliger et al. |
| 2010/0172803 A1 | 7/2010 | Stone et al. |
| 2010/0188073 A1 | 7/2010 | Rothberg et al. |
| 2010/0197507 A1 | 8/2010 | Rothberg et al. |
| 2010/0210479 A1 | 8/2010 | Griffiths et al. |
| 2010/0213628 A1 | 8/2010 | Bausch et al. |
| 2010/0233026 A1 | 9/2010 | Ismagliov et al. |
| 2010/0282617 A1 | 11/2010 | Rothberg et al. |
| 2010/0300559 A1 | 12/2010 | Schultz et al. |
| 2010/0300895 A1 | 12/2010 | Nobile et al. |
| 2010/0301398 A1 | 12/2010 | Rothberg et al. |
| 2010/0304982 A1 | 12/2010 | Hinz et al. |
| 2011/0000560 A1 | 1/2011 | Miller et al. |
| 2011/0142734 A1 | 6/2011 | Ismagliov et al. |
| 2011/0174622 A1 | 7/2011 | Ismagilov et al. |
| 2011/0176966 A1 | 7/2011 | Ismagilov et al. |
| 2011/0177494 A1 | 7/2011 | Ismagilov et al. |
| 2011/0177586 A1 | 7/2011 | Ismagilov et al. |
| 2011/0177609 A1 | 7/2011 | Ismagilov et al. |
| 2011/0188717 A1 | 8/2011 | Baudry et al. |
| 2011/0190146 A1 | 8/2011 | Boehm et al. |
| 2011/0244455 A1 | 10/2011 | Larson et al. |
| 2011/0250597 A1 | 10/2011 | Larson et al. |
| 2011/0275063 A1 | 11/2011 | Weitz et al. |
| 2012/0010098 A1 | 1/2012 | Griffiths et al. |
| 2012/0015382 A1 | 1/2012 | Weitz et al. |
| 2012/0015822 A1 | 1/2012 | Weitz et al. |

FOREIGN PATENT DOCUMENTS

| | | |
|---|---|---|
| EP | 0047130 B1 | 2/1985 |
| EP | 0249007 A3 | 3/1991 |
| EP | 0476178 A1 | 3/1992 |
| EP | 0540281 B1 | 7/1996 |
| EP | 0528580 B1 | 12/1996 |
| EP | 0895120 | 2/1999 |
| EP | 1741482 | 1/2007 |
| EP | 2127736 | 12/2009 |
| GB | 0114854.3 | 4/1969 |
| GB | 1446998 | 8/1976 |
| GB | 2005224 | 4/1979 |
| GB | 2047880 | 12/1980 |
| GB | 2062225 | 5/1981 |
| GB | 2064114 | 6/1981 |
| GB | 2097692 A | 11/1982 |
| GB | 0221053.2 | 6/1989 |
| WO | WO-84/02000 | 5/1984 |
| WO | WO-91/05058 | 4/1991 |
| WO | WO-91/07772 | 5/1991 |
| WO | WO-92/03734 | 3/1992 |
| WO | WO-92/21746 | 12/1992 |
| WO | WO-93/03151 | 2/1993 |
| WO | WO-93/08278 | 4/1993 |
| WO | WO-93/22053 | 11/1993 |
| WO | WO-93/22054 | 11/1993 |
| WO | WO-93/22055 | 11/1993 |
| WO | WO-93/22058 | 11/1993 |
| WO | WO-93/22421 | 11/1993 |
| WO | WO-94/16332 | 7/1994 |
| WO | WO-94/23738 | 10/1994 |
| WO | WO-94/24314 | 10/1994 |
| WO | WO-94/26766 | 11/1994 |
| WO | WO-95/11922 | 5/1995 |
| WO | WO-95/19922 | 7/1995 |
| WO | WO-95/24929 | 9/1995 |
| WO | WO-95/33447 | 12/1995 |
| WO | WO-96/34112 | 10/1996 |
| WO | WO-96/38730 | 12/1996 |
| WO | WO-96/40062 | 12/1996 |
| WO | WO-96/40723 | 12/1996 |
| WO | WO-97/00125 | 1/1997 |
| WO | WO-97/00442 | 1/1997 |
| WO | WO-97/04297 | 2/1997 |
| WO | WO-97/04748 | 2/1997 |
| WO | WO-97/23140 | 7/1997 |
| WO | WO-97/28556 | 8/1997 |
| WO | WO-97/39814 | 10/1997 |
| WO | WO-97/40141 | 10/1997 |
| WO | WO-97/45644 | 12/1997 |
| WO | WO-97/47763 | 12/1997 |
| WO | WO-98/00231 | 1/1998 |
| WO | WO-98/00705 | 1/1998 |
| WO | WO-98/02237 | 1/1998 |
| WO | WO-98/10267 | 3/1998 |
| WO | WO-98/13502 | 4/1998 |
| WO | WO-98/23733 | 6/1998 |
| WO | WO-98/31700 | 7/1998 |
| WO | WO-98/33001 | 7/1998 |
| WO | WO-98/34120 | 8/1998 |
| WO | WO-98/37186 | 8/1998 |
| WO | WO-98/41869 | 9/1998 |
| WO | WO-98/52691 | 11/1998 |
| WO | WO-98/58085 | 12/1998 |
| WO | WO-99/02671 | 1/1999 |
| WO | WO-99/22858 | 5/1999 |
| WO | WO-99/28020 | 6/1999 |
| WO | WO-99/31019 | 6/1999 |
| WO | WO-99/54730 | 10/1999 |
| WO | WO-99/61888 | 12/1999 |
| WO | WO-00/04139 | 1/2000 |
| WO | WO-00/47322 | 2/2000 |
| WO | WO-00/52455 | 2/2000 |
| WO | WO-00/40712 | 6/2000 |
| WO | WO-00/61275 | 10/2000 |
| WO | WO-00/70080 | 11/2000 |
| WO | WO-00/76673 | 12/2000 |
| WO | WO-01/12327 | 2/2001 |
| WO | WO-01/14589 | 3/2001 |
| WO | WO-01/18244 | 3/2001 |
| WO | WO-01/64332 | 9/2001 |
| WO | WO-01/68257 | 9/2001 |
| WO | WO-01/69289 | 9/2001 |
| WO | WO-01/72431 | 10/2001 |
| WO | WO-01/80283 | 10/2001 |

(56) References Cited

FOREIGN PATENT DOCUMENTS

| WO | WO-02/18949 | 3/2002 |
|---|---|---|
| WO | WO-02/22869 | 3/2002 |
| WO | WO-02/23163 | 3/2002 |
| WO | WO-02/31203 | 4/2002 |
| WO | WO-02/47665 | 6/2002 |
| WO | WO-02/060275 | 8/2002 |
| WO | WO-02/078845 | 10/2002 |
| WO | WO-02/103011 | 12/2002 |
| WO | WO-02/103363 | 12/2002 |
| WO | WO-03/011443 | 2/2003 |
| WO | WO-03/037302 | 5/2003 |
| WO | WO-03/044187 | 5/2003 |
| WO | WO-03/078659 | 9/2003 |
| WO | WO-03/099843 | 12/2003 |
| WO | WO-2004/002627 | 1/2004 |
| WO | WO-2004/018497 | 3/2004 |
| WO | WO-2004/024917 | 3/2004 |
| WO | WO-2004/038363 | 5/2004 |
| WO | WO-2004/069849 | 8/2004 |
| WO | WO-2004/074504 | 9/2004 |
| WO | WO-2004/083443 | 9/2004 |
| WO | WO-2004/087308 | 10/2004 |
| WO | WO-2004/088314 | 10/2004 |
| WO | WO-2004/091763 | 10/2004 |
| WO | WO-2004/102204 | 11/2004 |
| WO | WO-2004/103565 | 12/2004 |
| WO | WO-2005/000970 | 1/2005 |
| WO | WO-2005/002730 | 1/2005 |
| WO | WO-2005/021151 | 3/2005 |
| WO | WO-2005/103106 | 11/2005 |
| WO | WO-2005/118138 | 12/2005 |
| WO | WO-2006/002641 | 1/2006 |
| WO | WO-2006/009657 | 1/2006 |
| WO | WO-2006/027757 | 3/2006 |
| WO | WO-2006/038035 | 4/2006 |
| WO | WO-2006/040551 | 4/2006 |
| WO | WO-2006/040554 | 4/2006 |
| WO | WO-2006/078841 | 7/2006 |
| WO | WO-2006/096571 | 9/2006 |
| WO | WO-2006/101851 | 9/2006 |
| WO | WO-2007/021343 | 2/2007 |
| WO | WO-2007/030501 | 3/2007 |
| WO | WO-2007/081385 | 7/2007 |
| WO | WO-2007/081387 | 7/2007 |
| WO | WO-2007/089541 | 8/2007 |
| WO | WO-2007/114794 | 10/2007 |
| WO | WO-2007/123744 | 11/2007 |
| WO | WO-2007/133710 | 11/2007 |
| WO | WO-2007/138178 | 12/2007 |
| WO | WO-2008/021123 | 2/2008 |
| WO | WO-2008/063227 | 5/2008 |
| WO | WO-2008/097559 | 8/2008 |
| WO | WO-2008/121342 | 10/2008 |
| WO | WO-2008/130623 | 10/2008 |
| WO | WO-2009/029229 | 3/2009 |
| WO | WO-2010/040006 | 4/2010 |
| WO | WO-2010/056728 | 5/2010 |
| WO | WO-2010/151776 | 12/2010 |
| WO | WO-2011/042564 | 4/2011 |

OTHER PUBLICATIONS

Affholter and F. Arnold, Engineering a Revolution, Chemistry in Britain, Apr. 1999, p. 48.
Agrawal and Tang, Site-specific functionalization of oligodeoxynucleotides for non-radioactive labelling, Tetrahedron Letters 31:1543-1546 (1990).
Aharoni et al., High-Throughput screens and selections of enzyme-encoding genes, Curr Opin Chem Biol, 9(2): 210-6 (2005).
Ahn et al., Dielectrophoretic manipulation of drops for high-speed microluidic sorting devices, Applied Phys Lett 88, 024104 (2006).
Allen et al., High throughput fluorescence polarization: a homogeneous alternative to radioligand binding for cell surface receptors J Biomol Screen. 5(2):63-9 (2000).
Altman et al., Solid-state laser using a rhodamine-doped silica gel compound, IEEE Photonics technology letters 3(3):189-190 (1991).
Amstutz, P. et al., In vitro display technologies: novel developments and applications. Curr Opin Biotechnol, 12, 400-405 (2001).
Anarbaev et al., Klenow fragment and DNA polymerase alpha-primase fromserva calf thymus in water-in-oil microemulsions, Biochim Biophy Acta 1384:315-324 (1998).
Anderson et al., Preparation of a cell-free protein-synthesizing system from wheat germ, Methods Enzymol 101:635-44 (1983).
Anderson, J.E., Restriction endonucleases and modification methylases, Curr. Op. Struct. Biol., 3:24-30 (1993).
Ando, S. et al., PLGA microspheres containing plasmid DNA: preservation of supercoiled DNA via cryopreparation and carbohydrate stabilization, J Pharm Sci, 88(1):126-130 (1999).
Angell et al., Silicon micromechanical devices, Scientific American 248:44-55 (1983).
Anhuf et al., Determination of SMN1 and SMN2 copy number using TaqMan technology, Hum Mutat 22(1):74-78 (2003).
Anna et al., Formation of dispersions using flow focusing in microchannels, Applied Physics Letters,82(3): 364-366 (2003).
Arkin, M.R. et al., Probing the importance of second sphere residues in an esterolytic antibody by phage display, J Mol Biol 284(4):1083-94 (1998).
Armstrong et al., Multiple-Component Condensation Strategies for Combinatorial Library Synthesis, Acc. Chem. Res. 29(3):123-131 (1996).
Ashkin et al., Optical trapping and manipulation of single cells using infrared laser beams, Nature 330:769-771 (1987).
Ashkin and Dziedzic, Optical trapping and manipulation of viruses and bacteria, Science 235(4795):1517-20 (1987).
Atwell, S. & Wells, J.A., Selection for Improved Subtiligases by Phage Display, PNAS 96: 9497-9502(1999).
Auroux, Pierre-Alain et al., Micro Total Analysis Systems. 2. Analytical Standard Operations and Applications, Analytical Chemistry, vol. 74, No. 12, 2002, pp. 2637-2652.
Baccarani et al., *Escherichia coli* dihydrofolate reductase: isolation and characterization of tWO isozymes, Biochemistry 16(16):3566-72 (1977).
Baez et al., Glutathione transferases catalyse the detoxication of oxidized metabolites (o-quinones) of catecholamines and may serve as an antioxidant system preventing degenerative cellular processes, Biochem. J 324:25-28 (1997).
Baker, M., Clever PCR: more genotyping, smaller volumes, Nature Methods 7:351-356 (2010).
Ball and Schwartz, CMATRIX: software for physiologically based pharmacokinetic modeling using a symbolic matrix representation system, Comput Biol Med 24(4):269-76 (1994).
Ballantyne and Nixon, Selective Area Metallization by Electron-Beam Controlled Direct Metallic Deposition, J. Vac. Sci. Technol. 10:1094 (1973).
Barany F., The ligase chain reaction in a PCR WO rld, PCR Methods and Applications 1(1):5-16 (1991).
Barany, F. Genetic disease detection and DNA amplification using cloned thermostable ligase, PNAS 88(1): 189-93 (1991).
Baret et al., Fluorescence-activated droplet sorting (FADS): efficient microfluidic cell sorting based on enzymatic activity, Lab on a Chip 9:1850-1858 (2009).
Baret et al., Kinetic aspects of emulsion stabilization by surfactants: a microfluidic analysis, Langmuir 25:6088-6093 (2009).
Bass et al., Hormone Phage: An Enrichment Method for Variant Proteins With Altered Binding Properties, Proteins 8:309-314(1990).
Bauer, J., Advances in cell separation: recent developments in counterflow centrifugal elutriation and continuous flow cell separation, J Chromatography, 722:55-69 (1999).
Beebe et al., Functional hydrogel structures for autonomous flow control inside microfluidic channels, Nature 404:588-590 (2000).
Beer et al., On-Chip, Real-Time, Single-Copy Polymerase Chain Reaction in Picoliter Droplets, Anal. Chem., 2007, v. 79, pp. 847-8475.
Bein, Thomas, Efficient Assays for Combinatorial methods for the Discovery of Catalysts, Agnew. Chem. Int. Ed. 38:3, 323-26 (1999).

(56) References Cited

OTHER PUBLICATIONS

Benichou et al., Double Emulsions Stabilized by New Molecular Recognition Hybrids of Natural Polymers, Polym. Adv. Tehcnol 13:1019-1031 (2002).
Benner, S.A., Expanding the genetic lexicon: incorporating nonstandard amino acids into proteins by ribosome-based synthesis, Trends Biotechnol 12:158-63 (1994).
Benning, M.M. et al., The binding of substrate analogs to phosphotriesterase. J Biol Chem, 275, 30556-30560 (2000).
Berman et al., An agarose gel electrophoresis assay for the detection of DNA-binding activities in yeast cell extracts, Methods Enzymol 155:528-37 (1987).
Bernath et al, In Vitro Compartmentalization by Double Emulsions: Sorting and Gene Enrichment by Fluorescence Activated Cell Sorting, Anal. Biochem 325:151-157 (2004).
Bernath et al., Directed evolution of protein inhibitors of DNA-nucleases by in vitro compartmentalization (IVC) and nano-droplet delivery, J. Mol. Biol 345(5):1015-26 (2005).
Betlach, L. et al., A restriction endonuclease analysis of the bacterial plasmid controlling the EcoRI restriction and modification of DNA. Federation Proceedings, 35, 2037-2043 (1976).
Bibette et al., Emulsions: basic principles, Rep. Prog. Phys. 62: 969-1033 (1999).
Bico, Jose et al., Rise of Liquids and Bubbles in Angular Capillary Tubes, Journal of Colloid and Interface Science, vol. 247, 2002, pp. 162-166.
Bico, Jose et al., Self-Propelling Slugs, J. Fluid Mech., vol. 467, 2002, pp. 101-127.
Blattner and Dahlberg, RNA synthesis startpoints in bacteriophage lambda: are the promoter and operator transcribed?, Nature New Biol 237(77):227-32 (1972).
Boder et al., Yeast surface display for screening combinatorial polypeptide libraries, Nat Biotechnol 15(6):553-7 (1997).
Bougueleret, L. et al., Characterization of the gene coding for the EcoRV restriction and modification system of *Escherichia coli*, Nucleic Acids Res, 12(8):3659-76 (1984).
Boyum, A., Separation of leukocytes from blood and bone marrow. Introduction, Scand J Clin Lab Invest Suppl 97:7 (1968).
Branebjerg et al., Fast mixing by lamination, MEMS Proceedings 9th Ann WO rkshop, San Diego, Feb. 11-15, 1996, 9:441-446 (1996).
Braslavsky et al., Sequence information can be obtained from single DNA molecules, PNAS 100(7):3960-3964 (2003).
Bringer et al., Microfluidic Systems for Chemical Kinetics That Rely on Chaotic Mixing in Droplets, Philos Transact A Math Phys Eng Sci 362:1-18 (2004).
Brody et al., A self-assembled microlensing rotational probe, Applied Physics Letters, 74:144-46 (1999).
Brown et al., Chemical synthesis and cloning of a tyrosine tRNA gene, Methods Enzymol 68:109-151 (1979).
Bru, R. et al., Product inhibition of alpha-chymotrypsin in reverse micelles. Eur J Biochem 199(1): 95-103 (1991).
Bru, R. et al., Catalytic activity of elastase in reverse micelles, Biochem Mol Bio Int, 31(4):685-92 (1993).
Brummelkamp et al., A system for stable expression of short interfering RNAs in mammalian cells, Science 296(5567):550-3 (2002).
Buckpitt et al.,Hepatic and pulmonary microsomal metabolism of naphthalene to glutathione adducts: factors affecting the relative rates of conjugate formation, J. Pharmacol. Exp. Ther. 231:291-300 (1984).
Buican et al., Automated single-cell manipulation and sorting by light trapping, Applied Optics 26(24):5311-5316 (1987).
Burbaum, J., Miniaturization technologies in HTS: how fast, how small, how soon? Drug Discov Today 3:313-322 (1998).
Burns et al., Microfabricated structures for integrated DNA analysis, Proc. Natl. Acad. Sci. USA, May 1996, vol. 93, pp. 5556-5561.
Burns, Mark et al., An Integrated Nanoliter DNA Analysis Device, Science, vol. 282, 1998, pp. 484-487.
Burns, J.R. et al., The Intensification of Rapid Reactions in Multiphase Systems Using Slug Flow in Capillaries, Lab on a Chip, vol. 1, 2001 pp. 10-15.
Byrnes, P.J. et al., Sensitive fluorogenic substrates for the detection of trypsin-like proteases and pancreatic elastase, Anal Biochem, 126:447 (1982).
Cahill et al., Polymerase chain reaction and Q beta replicase amplification, Clin Chem 37(9):1482-5 (1991).
Caldwell, S.R. et al., Limits of diffusion in the hydrolysis of substrates by the phosphodiesterase from *Pseudomonas diminuta*, Biochemistry, 30: 7438-7444 (1991).
Calvert, P., Inkjet printing for materials and devices, Chem Mater 13: 3299-3305 (2001).
Caruthers, Gene synthesis machines: DNA chemistry and its uses, Science 230:281-285 (1985).
Chakrabarti, A.C. et al., Production of RNA by a polymerase protein encapsulated within phospholipid vesicles, J Mol Evol, 39(6):555-9 (1994).
Chamberlain and Ring, Characterization of T7-specific ribonucleic acid polymerase. 1. General properties of the enzymatic reaction and the template specificity of the enzyme, J Biol Chem 248:2235-44 (1973).
Chan, Emory M. et al., Size-Controlled Growth of CdSe Nanocrystals in Microfluidic Reactors, Nano Letters, vol. 3, No. 2, 2003, pp. 199-201.
Chang, T.M., Recycling of NAD(P) by multienzyme systems immobilized by microencapsulation in artifical cells, Methods Enzymol, 136(67):67-82 (1987).
Chang and Su, Controlled double emulsification utilizing 3D PDMS microchannels, Journal of Micromechanics and Microengineering 18:1-8 (2008).
Chao et al., Control of Concentration and Volume Gradients in Microfluidic Droplet Arrays for Protein Crystallization Screening, 26lh Annual International Conference of the IEEE Engineering in Medicine and Biology Society, San Francisco, California (Sep. 1-5, 2004).
Chao et al., Droplet Arrays in Microfluidic Channels for Combinatorial Screening Assays, Hilton Head 2004: A Solid State Sensor, Actuator and Microsystems WO rkshop, Hilton Head Island, South Carolina, (Jun. 6-10, 2004).
Chapman et al., In vitro selection of catalytic RNAs, Curr. op. Struct. Biol., 4:618-22 (1994).
Chayen, Crystallization with oils: a new dimension in macromolecular crystal growth Journal of Crystal Growth 196 (1999), pp. 434-441.
Chen et al., Capturing a Photoexcited Molecular Structure Through Time-Domain X-ray Absorption Fine Structure, Science 292(5515):262-264 (2001).
Chen et al., Microfluidic Switch for Embryo and Cell Sorting The 12th International Conference on Solid State Sensors, Actuators, and Microsystems, Boston, MA Jun. 8-12, 2003 Transducers, 1: 659-662 (2003).
Cheng, Z.,et al, Electro flow focusing inmicrofluidic devices, Microluidics Poster, presented at DBAS, Frontiers in Nanoscience, presented Apr. 10, 2003.
Chen-Goodspeed et al., Structural Determinants of the substrate and stereochemical specificity of phosphotriesterase, Biochemistry, 40(5):1325-31 (2001).
Chen-Goodspeed, M. et al., Enhancement, relaxation, and reversal of the stereoselectivity for phosphptriesterase by rational evolution of active site residues, Biochemistry, 40: 1332-1339 (2001b).
Chetverin and Spirin, Replicable RNA vectors: prospects for cell-free gene amplification, expression, and cloning, Prog Nucleic Acid Res Mol Biol, 51:225-70 (1995).
Chiba et al., Controlled protein delivery from biodegradable tyrosino-containing poly(anhydride-co-imide) microspheres, Biomaterials, 18(13): 893-901 (1997).
Chiou et al., A closed-cylce capillary polymerase chain reaction machine, Analytical Chemistry, American Chemical Society, 73:2018-21 (2001).
Chiu et al., Chemical transformations in individual ultrasmall biomimetic containers, Science, 283: 1892-1895 (1999).
Chou et al., A mirofabricated device for sizing and sorting DNA molecules 96:11-13(1998).
Clackson, T. et al., In vitro selection from protein and peptide libraries, Trends Biotechnol, 12:173-84 (1994).

(56) References Cited

OTHER PUBLICATIONS

Clausell-Tormos et al., Droplet-based microfluidic platforms for the encapsulation and screening of Mammalian cells and multicellular organisms, Chem Biol 15(5):427-437 (2008).
Cohen, S. et al., Controlled delivery systems for proteins based on poly(lactic/glycolic acid) microspheres, Pharm Res, 8(6):713-720 (1991).
Collins et al., Optimization of Shear Driven Droplet Generation in a Microluidic Device, ASME International Mechanical Engineering Congress and R&D Expo, Washington (2003).
Collins, J. et al., Microfluidic flow transducer based on the measurements of electrical admittance, Lab on a Chip, 4:7-10 (2004).
Compton, J., Nucleic acid sequence-based amplification, Nature, 350(6313):91-2 (1991).
Cormack, B.P. et al., FACS-optimized mutants of the green fluorescent protein (GFP), Gene 173(1):33-38 (1996).
Cortesi et al., Production of lipospheres as carriers for bioactive compounds, Biomateials, 23(11): 2283-2294 (2002).
Craig, D. et al., Fluorescence-based enzymatic assay by capillary electrophoresis laser-induced fluorescence detection for the determinination of a few alpha-galactosidase molecules, Anal. Biochem. 226: 147 (1995).
Creagh, A.L. et al., Structural and catalytic properties of enzymes in reverse micelles, Enzyme Microb Technol 15(5): 383-92 (1993).
Crosland-Taylor, A Device for Counting Small Particles suspended in a Fluid through a Tube, Nature 171:37-38 (1953).
Crowley, J. M., Electrical breakdown of bimolecular lipid membranes as an electromechanical instability, Biophys J. 13(7):711-724 (1973).
Cull, M.G. et al., Screening for receptor ligands using large libraries of peptides linked to the C terminus of the lac repressor, PNAS 89:1865-9 (1992).
Curran, D.P., Strategy-level separations in organic synthesis: from planning to practice. Angew Chem Int Ed, 37: 1174-11-96 (1998).
Czarnik, A.W., Encoding methods for combinatorial chemistry, Curr Opin Chem Biol 1:60-66 (1997).
Dankwardt et al., Combinatorial synthesis of small-molecule libraries using 3-amino-5-hydroxybenzoic acid, 1:113-120 (1995).
Davis, S.S. et al., Multiple emulsions as targetable delivery systems, Methods in Enzymology, 149: 51-64 (1987).
Davis, J.A. et al., Deterministic hydrodynamics: Taking blood apart, PNAS 103:14779-14784 (2006).
De-Bashan, L. E. et al., Removal of ammonium and phosphorus ions from synthetic wastewater by the microalgae *Chlorella vulgaris* coimmobilized in alginate beads with the microalgae growth-promoting bacterium *Azospirillum brasilense*, Water Research 36 (2002),pp. 2941-2948.
de Gans, B.J. et al., Inkjet printing of polymers: state of the art and future developments, Advanced materials, 16: 203-213 (2004).
Delagrave, S. et al., Red-shifted excitation mutants of the green fluorescent protein, Biotechnology 13(2):151-4 (1995).
DelRaso, In vitro methodologies for enhanced toxicity testing, Toxicol. Lett. 68:91-99 (1993).
Demartis et al., A strategy for the isolation of catalytic activities from repertoires of enzymes displayed on phage, J. Mol. Biol 286:617-633 (1999).
Dickinson, E., Emulsions and droplet size control, Wedlock, D.J., Ed., in Controlled Particle Droplet and Bubble Formulation, ButterWO rth-Heine-mann, 191-257 (1994).
DiMatteo, A., Genetic conversion of an SMN2 gene to SMN1: A novel approach to the treatment of spinal muscular atrophy, Exp Cell Res. 314(4):878-886 (2008).
Dinsmore et al., Colioidosomes: Selectively Permeable Capsules Composed of Colloidal Particles, Science 298(5595):1006-1009. (2002).
Dittrich et al., A new embedded process for compartmentalized cell-free protein expression and on-line detection in microfluidic devices, Chembiochem 6(5):811-814 (2005).
Doi, N. and Yanagawa, H. STABLE: protein-DNA fusion system for screening of combinatorial protein libraries in vitro, FEBS Lett., 457: 227-230 (1999).
Doi et al., In vitro selection of restriction endonucleases by in vitro compartmentilization, Nucleic Acids Res, 32(12): e95 (2004).
Doman, T.N. et al., Molecular docking and high-throughput screening for novel inhibitors of protein tyrosine phosphatase-1B, J Med Chem, 45: 2213-2221 (2002).
Domling and Ugi, Multicomponent Reactions with Isocyanides, Angew Chem Int Ed 39(18):3168-3210 (2000).
Domling A., Recent advances in isocyanide-based multicomponent chemistry, Curr Opin Chem Biol, 6(3):306-13 (2002).
Dove et al., In Brief, Nature Biotechnology 20:1213 (2002).
Dower et al., High efficiency transformation of *E. coli* by high voltage electroporation, Nucleic Acids Res 16:6127-6145 (1988).
Dressman et al., Transforming single DNA molecules into fluorescent magnetic particles for detection and enumeration of genetic variations, PNAS 100:8817-22 (2003).
Drmanac et al., Sequencing by hybridization: towards an automated sequencing of one million M13 clones arrayed on membranes, Elctrophoresis 13:566-573 (1992).
Dreyfus et al., Ordered and discordered patterns in tw-phase flows in microchannels, Phys Rev Lett 90(14):144505-1-144505-4 (2003).
Dubertret et al., In vivo imaging of quantum dots encapsulated in phospholipid micelles, Science, 298: 1759-1762 (2002).
Duffy et al., Rapid Protyping of Microfluidic Systems and Polydimethylsiloxane, Anal Chem 70:474-480 (1998).
Duggleby, R. G. Enzyme Kinetics and Mechanisms, Pt D. Academic Press 249:61-90 (1995).
Dumas, D.P., Purification and properties of the phosphotriesterase from *Psuedomonas diminuta*, J Biol Chem 264: 19659-19665 (1989).
Eckert and Kunkel, DNA polymerase fidelity and the polymerase chain reaction, Genome Res 1:17-24 (1991).
Edd et al., Controlled encapsulation of single-cells into monodisperse picolitre drops, Lab Chip 8(8):1262-1264 (2008).
Edel, Joshua B. et al., Microfluidic Routes to the Controlled Production of Nanopaticles, Chemical Communications, 2002 pp. 1136-1137.
Edris et al., Encapsulation of orange oil in a spray dried double emulsion, Nahrung/Food, 45(2):133-137 (2001).
Effenhauser et al., Glass chips for high-speed capillary electrophoresis separations with submicrometer plate heights, Anal Chem 65:2637-2642 (1993).
Eggers, Jens et al., Coalescence of Liquid Drops, J. Fluid Mech., vol. 401, 1999, pp. 293-310.
Ehrig, T. et al., Green-fluorescent protein mutants with altered fluorescence excitation spectra, Febs Lett, 367(2):163-66 (1995).
Eigen, Wie entsteht information? Prinzipien der selbstorganisation in der biologie, Berichte der punsen-gesellschaft fur physikalische chemi, 80:1059-81 (1976).
Eigen et al., hypercycles and compartments: compartments assists—but does not replace—hypercyclic organization of early genetic information, J Theor Biol, 85:407-11 (1980).
Eigen et al., The hypercycle: coupling of RNA and protein biosynthesis in the infection cycle of an RNA bacteriophage, Biochemistry, 30:11005-18 (1991).
Ellington and Szostak, In vitro selection of RNA molecules that bind specific ligands, Nature, 346:818-822 (1990).
Ellman et al., Biosynthetic method for introducing unnatural amino acids site-specifically into proteins, Methods Enzymol, 202:301-36 (1991).
Endo et al., Autocatalytic decomposition of cobalt complexes as an indicator system for the determination of trace amounts of cobalt and effectors, Analyst 121:391-394 (1996).
Endo et al. Kinetic determination of trace cobalt by visual autocatalytic indication, Talanta 47:349-353 (1998).
Eow et al., Electrostatic enhancement of coalescence of water droplets in oil: a review of the technology, Chemical Engineeing Journal 85:357-368 (2002).
Eow, et al. Electrostatic and hydrodynamic separation of aqueous drops in a flowing viscous oil, Chemical Eng Proc 41:649-657 (2002).

(56) References Cited

OTHER PUBLICATIONS

Eow et al., Electrocoalesce-separators for the separation of aqueous drops from a flowing dielectric viscous liquid, Separation and Purification Tech 29:63-77 (2002).
Eow et al., Motion, deformation and break-up of aqueous drops in oils under high electric ?eld strengths, Chemical Eng Proc 42:259-272 (2003).
Eow et al., The behavior of a liquid-liquid interface and drop-interface coalescence under the in?uence of an electric field, Colloids and Surfaces A: Physiochern. Eng. Aspects 215:101-123 (2003).
Faca et al., A mouse to human search for plasma proteome chagnes associated with pancreatic tumor development, PLoS Med 5(6):e123 (2008).
Fahy et al., Self-sustained sequence replication (3SR): an isothermal transcription-based amplification system alternative to PCR, PCR Methods Appl 1:25-33 (1991).
Fan and Harrison, Micromachining of capillary electrophoresis injectors and separators on glass chips and evaluation of flow at capillary intersections, Anal Chem 66:177-184 (1994).
Fastrez, J., In vivo versus in vitro screening or selection for catalytic activity in enzymes and abzymes, Mol Biotechnol 7(1):37-55 (1997).
Fettinger et al., Stacked modules for micro flow systems in chemical analysis: concept and studies using an enlarged model, Sens Actuat B. 17:19-25 (1993).
Fiedler et al., Dielectrophoretic sorting of particles and cells in a microsystem, Anal Chem 70(9):1909-1915 (1998).
Field, J. et al., Purification of a RAS-responsive adenylyl cyclase complex from *Saccharomyces cervisiae* by use of an epitope addition method. Mol Cell Biol, 8: 2159-2165 (1988).
Fields, S. and Song, O., A novel genetic system to detect protein-protein interactions, Nature 340(6230): 245-6 (1989).
Filella et al., TAG-72, CA 19.9 and CEA as tumor markers in gastric cancer, Acta Oncol. 33(7):747-751 (1994).
Finch, C.A., Industrial Microencapsulation: Polymers for Microcapsule Walls, pp. 1-12 in Encapsulation and Controlled Release, WO odhead Publishing (1993).
Finch, C.A., Encapsulation and controlled release, Spec Publ R Soc Chem, 138:35 (1993).
Fire & Xu, Rolling replication of short DNA circles, PNAS 92(10):4641-5 (1995).
Firestine, S.M. et al., Using an AraC-based three hybrid system to detect biocatalysts in vivo, Nat Biotechnol 18: 544-547 (2000).
Fisch et al., A strategy of exon shuffling for making large peptide repertoires displayed on filamentous bacteriophage, PNAS 93:7761-6 (1996).
Fisher et al., Cell Encapsulation on a Microfluidic Platform, The Eighth International Conference on Miniaturised Systems for Chemistry and Life Scieces, MicroTAS 2004, Sep. 26-30, Malmo, Sweden.
Fletcher et al., Micro reactors: principles and applications in organic synthesis, Tetrahedron 58:4735-4757 (2002).
Fluri et al., Integrated capillary electrophoresis devices with an efficient postcolumn reactor in planar quartz and glass chips, Anal Chem 68:4285-4290 (1996).
Fornusek, L. et al., Polymeric microspheres as diagnostic tools for cell surface marker tracing, Crit Rev Ther Drug Carrier Syst, 2:137-74 (1986).
Fowler, Enhancement of Mixing By Droplet-Based Microfluidics, Int Conf MEMS 97-100 (2002).
Freese, E., The specific mutagenic effect of base analogues on Phage T4, J Mol Biol, 1: 87 (1959).
Frenz et al., Reliable microfluidic on-chip incubation of droplets in delay-lines, Lab on a Chip 9:1344-1348 (2008).
Fu et al., A microfabricated fluorescence-activated cell sorter, Nature Biotechnology, 17(11):1109-1111 (1999).
Fu et al., An Integrated Microfabricated Cell Sorter, Anal. Chem., 74: 2451-2457 (2002).
Fulton et al., Advanced multiplexed analysis with the FlowMetrix system, Clin Chem 43:1749-1756 (1997).
Fulwyler, Electronic Separation of Biological Cells by Volume, Science 150(3698):910-911 (1965).
Gallarate et al., On the stability of ascorbic acid in emulsified systems for topical and cosmetic use, Int J Pharm 188(2):233-241 (1999).
Ganan-Calvo, Generation of Steady Liquid Microthreads and Micron-Sized Monodisperse Sprays and Gas Streams, Phys Rev Lett 80(2):285-288 (1998).
Ganan-Calvo, A.M., Perfectly Monodisperse Microbubbling by Capillary Flow Focusing, Phys Rev Lett 87(27): 274501-1-4 (2001).
Garcia-Ruiz et al., Investigation on protein crystal growth by the gel acupuncture method{, Acta, Cryst., 1994, D50, 99. pp. 484-490.
Garcia-Ruiz et al. A super-saturation wave of protein crystallization, J. Crystal Growth, 2001, v232, pp. 149-155.
Gasperlin et al., The structure elucidation of semisolid w/o emulsion systems containin silicone surfactant, Intl J Pharm, 107:51-6 (1994).
Gasperlin et al., Viscosity prediction of lipophillic semisolid emulsion systems by neural netWO rk modeling, Intl J Pharm, 196:37-50 (2000).
Georgiou et al., Display of heterologous proteins on the surface of microorganisms: from the screeign of combinatiorial libraires to live recombinant vaccines. Nat Biotechnol 15(1), 29-34 (1997).
Georgiou, G., Analysis of large libraries of protein mutants using flow cytometry, Adv Protein Chem, 55: 293-315 (2000).
Gerdts et al., A Synthetic Reaction NetWO rk: Chemical Amplification Using Nonequilibrium Autocatalytic Reactions Coupled in Time, J. Am. Chem. Soc 126:6327-6331 (2004).
Ghadessy et al., Directed Evolution of Polymerase Function by Compartmentalized Self-Replication, PNSAS 98(8): 4552-4557 (2001).
Gibbs et al., Detection of single DNA base differences by competitive oligonucleotide priming, Nucleic Acids Res. 17(7): 2437-48 (1989).
Gilliland, G., Analysis of cytokine mRNA and DNA: Detection and quantitation by competitive polymerase chain reaction, PNAS, 87(7):2725-9 (1990).
Giusti et al., Synthesis and characterization of 5{ fluorescent dye labeled oligonucleotides, Genome Res 2:223-227 (1993).
Gold et al., Diversity of Oligonucleotide Functions Annu Rev Biochem, 64: 763-97 (1995).
Goodall, J. L. et al., Operation of Mixed-Culture Immobilized Cell Reactors for the Metabolism of Meta- and Para-Nitrobenzoate by *Comamonas* Sp. JS46 and *Comamonas* Sp. JS47, Biotechnology and Bioengineering, vol. 59, No. 1, Jul. 5, 1998, pp. 21-27.
Gordon and Balasubramanian, Solid phase synthesis—designer linkers for combinatorial chemistry: a review, J. Chem. Technol. Biotechnol., 74(9):835-851 (1999).
Grasland-Mongrain et al., Droplet coalescence in microfluidic devices, 30 pages (Jul. 2003) From internet: http://www.eleves.ens.fr/home/grasland/rapports/stage4.pdf.
Green, R. and Szostak, J.W., Selection of a Ribozyme That Functions as a Superior Template in a Sel£ Copying Reaction, Science, 258: 1910-5 (1992).
Gregoriadis, G., Enzyme entrapment in liposomes, Methods Enzymol 44:218-227 (1976).
Griffiths et al., Isolation of high affinity human antibodies directly from large synthetic repertoires, Embo J 13(14):3245-60 (1994).
Griffiths, A.D. et al., Strategies for selection of antibodies by phage display, Curr Opin Biotechnol, 9:102-8 (1998).
Griffiths et al., Man-made enzymes—from design to in vitro compartmentalisation, Curr Opin Biotechnol 11:338-353 (2000).
Griffiths et al., Directed evolution of an extremely fast phosphotriesterase by in vitro compartmentalization, EMBO J, 22:24-35 (2003).
Griffiths, A., and Tawfik, D., Miniaturising the laboratory in emulsion droplets, Trend Biotech 24(9):395-402 (2006).
Guatelli, J.C. et al., Isothermal, in vitro amplification of nucleic acids by a multienzyme reaction modeled after retroviral replication, PNAS, 87(5):1874-8 (1990).
Guixe et al., Ligand-Induced Conformational Transitions in *Escherichia coli* Phosphofructokinase 2: Evidence for an Allosteric Site for MgATP2n, Biochem., 37: 13269-12375 (1998).
Gupta, K.C., et al., A general method for the synthesis of 3'-sulfhydryl and phosphate group containing oligonucleotides, Nucl Acids Res 19 (11): 3019-3026 (1991).
Haber et al., Activity and spectroscopic properties of bovine liver catalase in sodium bis(2-ethylhexyl) sulfosuccinate/isooctane reverse micelles, Eur J Biochem 217(2): 567-73 (1993).

(56) References Cited

OTHER PUBLICATIONS

Habig and Jakoby, Assays for differentiation of glutathione S-transferases, Methods in Enzymology, 77: 398-405 (1981).
Hadd et al., Microchip Device for Performing Enzyme Assays, Anal. Chem 69(17): 3407-3412 (1997).
Haddad et al., A methodology for solving physiologically based pharmacokinetic models without the use of simulation software, Toxicol Lett. 85(2): 113-26 (1996).
Hagar and Spitzer, The effect of endotoxemia on concanavalin A induced alterations in cytoplasmic free calcium in rat spleen cells as determined with Fluo-3, Cell Calcium 13:123-130 (1992).
Hai et al., Investigation on the release of fluorescent markers from the w/o/w emulsions by fluorescenec-activated cell sorter, J Control Release, 96(3): 393-402 (2004).
Haies et al., Morphometric study of rat lung cells. I. Numerical and dimensional characteristics of parenchymal cell population, Am. Rev. Respir. Dis. 123:533-54 (1981).
Hall, Experimental evolution of Ebg enzyme provides clues about the evolution of catalysis and to evolutionary potential, FEMS Microbiol Lett, 174(1):1-8 (1999).
Hall, The EBG system of *E. coli*: origin and evolution of a novel beta-galactosidase for the metabolism of lactose, Genetica 118(2-3):143-56 (2003).
Han et al., Quantum-dot-tagged Microbeads for Multiplexed Optical Coding of Biomolecules, Nat Biotech 19(7): 631-635 (2001).
Handen, J.S., High-throughput screening—challenges for the future, Drug Discov WO rld, 47-50 (2002).
Handique, K. et al., On-Chip Thermopneumatic Pressure for Discrete Drop Pumping, Analytical Chemistry, vol. 73, 2001, pp. 1831-1838.
Hanes et al., In vitro selection and evolution of functional proteins by using ribosome display, PNAS 94:4937-42 (1997).
Hanes et al., Degradation of porous poly(anhydide-co-imide) microspheres and implication for controlled macromolecule delivery, Biomaterials, 19(1-3): 163-172(1998).
Hansen et al., A robust and scalable microfluidic metering method that allows protein crystal growth by free interface diffusion, PNAS 99(26):16531-16536 (2002).
Harada et al., Monoclonal antibody G6K12 specific for membrane-associated differentiation marker of human stratified squamous epithelia and squamous cell carcinoma, J. Oral Pathol. Med 22(4):145-152 (1993).
Harder, K.W. et al., Characterization and kinetic analysis of the intracellular domain of human protein tyrosine phosphatase beta (HPTP beta) using synthetic phosphopeptides, Biochem J 298 (Pt 2): 395-401 (1994).
Harries et al., A Numerical Model for Segmented Flow in a Microreactor, Int J of Heat and Mass Transfer, 46:3313-3322 (2006).
Harris et al., Single-molecule DNA sequencing of a viral genome, Science 320(5872):106-109 (2008).
Harrison et al., Micromachining a miniaturized capillary electrophoresis-based chemical analysis system on a chip, Science 261(5123):895-897 (1993).
Hasina et al., Plasminogen activator inhibitor-2: a molecular biomarker for head and neck cancer progression, Cancer Research 63:555-559 (2003).
Hayward et al., Dewetting Instability during the Formation of Polymersomes from BloceCopolymer-Stabilized Double Emulsions, Langmuir, 22(10): 4457-4461 (2006).
He et al., Selective encapsulation of single cells and subcellular organelles into picoliter- and femtoliter-volume droplets, Anal Chem 77(6):1539-1544 (2005).
Heim et al., Engineering Green Fluorescent Protein for Improved Brightness, Longer Wavelengths and Fluorescence Response Energy Transfer, Carr. Biol, 6(2): 178-182 (1996).
Hellman et al., Differential tissue-specific protein markers of vaginal carcinoma, Br J Cancer, 100(8): 1303-131 (2009).
Hergenrother et al., Small-Molecule Microarrays: Covalent Attachment and Screening of Alcohol-Containing Small Molecules on Glass Slides, J. Am. Chem. Soc, 122: 7849-7850 (2000).

Hildebrand et al., Liquid-Liquid Solubility of Perfluoromethylcyclohexane with Benzene, Carbon Tetrachloride, Chlorobenzene, Chloroform and Toluene, J. Am. Chem. Soc, 71:22-25 (1949).
Hjelmfelt et al, Pattern-Recognition in Coupled Chemical Kinetic Systems, Science, 260(5106):335-337 (1993).
Ho, S.N. et al., Site-directed mutageneiss by overlap extension using the polymerase chain reaction, Gene, 77(1):51-9 (1989).
Hoang, Physiologically based pharmacokinetic models: mathematical fundamentals and simulation implementations, Toxicol Lett 79(1-3):99-106 (1995).
Hochuli et al., New metal chelate adsorbent selective for proteins and peptides containing neighbouring histidine residues, J Chromatogr 411: 177-84 (1987).
Holmes et al., Reagents for Combinatorial Organic Synthesis: Development of a New O-Nitrobenzyl Photolabile Linder for Solid Phase Synthesis, J. OrgChem., 60: 2318-2319(1995).
Hong, S.B. et al., Stereochemical constraints on the substrate specificity of phosphodiesterase, Biochemistry, 38: 1159-1165 (1999).
Hoogenboom et al., Multi-subunit proteins on the surface of filamentous phage: methodologies for displaying antibody (Fab) heavy and light chains, Nucl Acids Res., 91: 4133-4137 (1991).
Hoogenboom, H.R., Designing and optimizing library selection strategies for generating high-affinity antibodies, Trends Biotechnol, 15:62-70 (1997).
Hopfinger & Lasheras, Explosive Breakup of a Liquid Jet by a Swirling Coaxial Jet, Physics of Fluids 8(7):1696-1700 (1996).
Hopman et al., Rapid synthesis of biotin-, digoxigenin-, trinitrophenyl-, and fluorochrome-labeled tyramides and their application for In situ hybridization using CARD amplification, J of Histochem and Cytochem, 46(6):771-77 (1998).
Horton et al., Engineering hybrid genes without the use of restriction enzymes: gene splicing by overlap extension, Gene 77(1), 61-8 (1989).
Hosokawa, Kazuo et al., Handling of Picoliter Liquid Samples in a Poly(dimethylsiloxane)-Based Microfluidic Device, Analytical Chemistry, vol. 71, No. 20, 1999 pp. 4781-4785.
Hsu et al., Comparison of process parameters for microencapsulation of plasmid DNA in poly(D, L-lactic-co-glycolic acid microspheres, J Drug Target, 7:313-23 (1999).
Huang, Z.J., Kinetic assay of fluorescein mono-beta-D-galactosidase hydrolysis by beta-galactosidase: a front-face measurement for strongly absorbing fluorogenic substrates, Biochemistry, 30:8530-4 (1991).
Huang, Z. et al., A sensitive competitive ELISA for 2,4-dinitrophenol using 3,6-fluorescein diphosphate as a fluorogenic substrate, J Immunol Meth, 149:261 (1992).
Huang L. R. et al., Continuous particle separation through deterministic lateral displacement, Science 304(5673):987-990 (2004).
Hubert et al. Data Concordance from a Comparison between Filter Binding and Fluorescence Polarization Assay Formats for Identification of RUOCK-II Inhibitors, J biomol Screen 8(4):399-409 (2003).
Huebner, A. et al., Quantitative detection of protein expression in single cells using droplet microfluidics, Chem Com 12:1218-1220 (2007).
Hung et al., Optimization of Droplet Generation by controlling PDMS Surface Hydrophobicity, 2004 ASME International Mechanical Engineering Congres and RD&D Expo, Nov. 13-19, 2004, Anaheim, CA.
Hung, et al, Controlled Droplet Fusion in Microfluidic Devices, MicroTAS 2004, Sep. 26-30, Malmo, Sweden (2004).
Hutchison et al., Cell-free cloning using Phi29 polymerase, PNAS 102(48):17332-17336 (2005).
Ibrahim, S.F. et al., High-speed cell sorting: fundamentals and recent advances, Curr Opin Biotchnol, 14(1):5-12 (2003).
Ikeda et al., Bioactivation of tegafur to 5-fluorouracil is catalyzed by cytochrome P-450 2A6 in human liver microsomes in vitro, Clin Cancer Res 6(11):4409-4415 (2000).
Inai et al., Immunohistochemical detection of an enamel protein-related epitope in rat bone at an early stage of osteogenesis, Histochemistry 99(5):335-362 (1993).

(56) References Cited

OTHER PUBLICATIONS

Ismagilov, Integrated Microfluidic Systems, Angew. Chem. Int. Ed 42:4130-4132 (2003).
Janda, et al, Chemical selection for catalysis in combinatorial antibody libraries, Science, 275:945-948 (1997).
Jang et al., Controllable delivery of non-viral DNA from porous scaffold, J Controlled Release 86(1):157-168 (2003).
Jermutus et al., Recent advances in producing and selecting functional proteins by using cell-free translation, Curr Opin Biotechnol 9(5): 534-48 (1998).
Jestin et al., A Method for the Selection of Catalytic Activity Using Phage Display and Proximity Coupling, Agnew. Chem. Int. Ed. Engi. 38(8):1124-1127 (1999).
Jo, et al, Encapsulation of Bovine Serum Albumin in Temperature-Programmed Shell-in-Shell Structures, Macromol. Rapid Comm 24:957-962 (2003).
Joerger et al., Analyte detection with DNA-labeled antibodies and polymerase chain reaction, Clin. Chem. 41(9):1371-7 (1995).
Johannsson et al., Amplification by Second Enzymes, In ELISA and Other Solid Phase Immunoassays, Kemeny et al (ed.), Chapter 4, pp. 85-106 John Wiley (1988).
Johannsson, A., Heterogeneous Enzyme Immunoassays, In Principles and Practice of Immunoassay, pp. 295-325 Stockton Press (1991).
Johnson, T.O. et al., Protein tyrosine phosphatase 1B inhibitors for diabetes, Nature Review Drug Discovery 1, 696-709 (2002).
Jones, L.J. et al., Quenched BODIPY dye-labeled casein substrates for the assay of protease activity by direct fluorescence measurement, Anal Biochem, 251:144 (1997).
Jones et al. Glowing jellyfish, luminescence and a molecule called coelenterazine, Trends Biotechnol. 17(12):477-81 (1999).
Joo et al., Laboratory evolution of peroxide-mediated cytochrome P450 hydroxylaion, Nature 399:670 (1999).
Joos et al., Covalent attachment of hybridizable oligonucleotides to glass supports, Analytical Biochemistry 247:96-101 (1997).
Joyce, G.F., In vitro Evolution of Nucleic Acids, Curr. Opp. Structural Biol, 4: 331-336 (1994).
Kadir and Moore, Haem binding to horse spleen ferritin, Febs Lett, 276: 81-4 (1990).
Kallen, R.G. et al., The mechanism of the condensation of formaldehyde with tetrahydrofolic acid, J. Biol. Chem., 241:5851-63 (1966).
Kambara et al., Optimization of Parameters in a DNA Sequenator Using Fluorescence Detection, Nature Biotechnology 6:816-821 (1988).
Kamensky et al., Spectrophotometer: new instrument for ultrarapid cell analysis, Science 150(3696):630-631 (1965).
Kanouni et al., Preparation of a stable double emulsion (W1/0/W2): role of the interfacial ilms on the stability of the system, Adv. Collid. Interf. Sci., 99(3): 229-254 (2002).
Katanaev et al., Viral Q beta RNA as a high expression vector for mRNA translation in a cell-free system, Febs Lett, 359:89-92 (1995).
Katsura et al., Indirect micromanipulation of single molecules in water-in-oil emulsion, Electrophoresis, 22:289-93 (2001).
Kawakatsu et al., Regular-sized cell creation in microchannel emulsification by visual microprocessing method, Journal of the American Oil ChemistS Society, 74:317-21 (1997).
Keana J. & Cai, S. X., New reagents for photoaffinity labeling: synthesis and photolysis of functionalized perfluorophenyl azides, J. Org. Chem.55(11):3640-3647 (1990).
Keefe, A.D. et al., Functional proteins from a random-sequence library, Nature, 410: 715-718 (2001).
Keij, J.F., et al., High-speed photodamage cell sorting: An evaluation of the ZAPPER prototype, Methods in cell biology, 42: 371-358 (1994).
Keij et al., High-Speed Photodamage Cell Selection Using a Frequency-Doubled Argon Ion Laser, Cytometry, 19(3): 209-216 (1995).
Kelly et al., Miniaturizing chemistry and biology in microdroplets, Chem Commun 18:1773-1788 (2007).
Kerker, M., Elastic and inelastic light scattering in flow cytometry, Cytometry, 4:1-10 (1983).
Khandjian, UV crosslinking of RNA to nylon membrane enhances hybridization signals, Mol. Bio. Rep. 11: 107-115 (1986).
Kim S. et al, Type II quantum dots: CdTe/CdSe (core/shell) and CdSe/ZnTe (core/shell) heterostructures, J. Am Chem Soc. 125:11466-11467 (2003).
Kim et al., Comparative study on sustained release of human growth hormone from semi-crystalline poly(L-lactic acid) and amorphous poly(D,L-lactic-co-glycolic acid) microspheres: morphological effect on protein release, Journal of Controlled Release, 98(1):115-125 (2004).
Kircher et al., High-throughput DNA sequencing—concepts and limitations, Bioessays 32(6):524-536 (2010).
Kiss et al., High-throughput quantitative polymerase chain reaction in picoliter droplets, Anal. Chem 80:8975-8981 (2008).
Kitagawa et al., Manipulation of a single cell with microcapillary tubing based on its electrophoretic mobility, Electrophoresis 16:1364-1368 (1995).
Klug and Famulok, All you wanted to know about selex, Molecular Biology Reports, 20:97-107 (1994).
Klug, A., Gene Regulatory Proteins and Their Interaction with DNA, Ann NY Acad Sci, 758: 143-60 (1995).
Klug and Schwabe, Protein motifs 5. Zinc fingers, FASEB J 9(8):597-604 (1995).
Knaak et al., Development of partition coefficients, Vmax and Km values, and allometric relationships, Toxicol Lett. 79(I-3):87-98 (1995).
Knight, James B., Hydrodynamic Focusing on a Silicon Chip: Mixing Nanoliters in Microseconds, Physical Review Lett 80(17):3863-3866 (1998).
Kojima et al. PCR amplification from single DNA molecules on magnetic beads in emulsion: application for high-throughput screening of transcription factor targets. Nucleic Acids Res. 33:e150 (2005).
Kolb et al., Cotranslational folding of proteins, Biochem Cell Biol, 73:1217-20 (1995).
Kopp et al., Chemical amplification: continuous flow PCR on a chip, Science, 280:1046-48 (1998).
Koster et al., Drop-based micro?uidic devices for encapsulation of single cells, Lab on a Chip 8:1110-1115 (2008).
Kowalczykowski et al., Biochemistry of homologous recombination in *Escherichia coli*, Microbiol Rev 58(3):401-65 (1994).
Krafft et al., Emulsions and microemulsions with a ?uorocarbon phase, Colloid and Interface Science 8(3):251-258 (2003).
Krafft et al., Synthesis and preliminary data on the biocompatibility and emulsifying properties of perfluoroalkylated phosphoramidates as injectable surfactants, Eur. J. Med. Chem., 26:545-550 (1991).
Kralj et al., Surfactant-enhanced liquid-liquid extraction in microfluidic channels with inline electric-field enhanced coalescence, Lab Chip 5:531-535 (2005).
Kricka and Wilding, Micromachining: a new direction for clinical analyzers, Pure and Applied Chemistry 68(10):1831-1836 (1996).
Kricka and Wilding, Microchip PCR, Anal Bioanal Chem 377(5):820-825 (2003).
Krumdiek, C.L. et al., Solid-phase synthesis of pteroylpolyglutamates, Methods Enzymol, 524-29 (1980).
Kumar, A. et al., Activity and kinetic characteristics of gltathione reductase in vitro in reverse micellar waterpool, Biochem Biophys Acta, 996(1-2):1-6 (1989).
Lage et al., Whole genome analysis of genetic alterations in small DNA samples using hyperbranched strand displacement amplification and array-CGH. Genome Res. 13: 294-307 (2003).
Lamprecht et al., pH-sensitive microsphere delivery increases oral bioavailability of calcitonin, Journal of Controlled Release, 98(1): 1-9(2004).
Lancet, D. et al., Probability model for molecular recognition in biuological receptor repertoirs: significance to the olfactory system, PNAS, 90(8):3715-9 (1993).
Landergren et al., A ligase mediated gene detection technique. Science 241(4869):1077-80 (1988).
Lasheras, et al., Breakup and Atomization of a Round Water Jet by a High Speed Annular Air Jet, J Fluid Mechanics 357:351-379 (1998).

(56) References Cited

OTHER PUBLICATIONS

Leary et al., Application of Advanced Cytometric and Molecular Technologies to Minimal Residual Disease Monitoring, Proceedings of SPIE 3913:36-44 (2000).
Lee, et al, Preparation of Silica Paticles Encapsulating Retinol Using O/W/O Multiple Emulsions, Journal of Colloid and Interface Science, 240(1): 83-89 (2001).
Lee, et al, Effective Formation of Silicone-in-Fluorocarbon-in-Water Double Emulsions: Studies on Droplet Morphology and Stability, Journal of Dispersion Sci Tech 23(4):491-497(2002).
Lee et al, Investigating the target recognition of DNA cytosine-5 methyltransferase Hhal by library selection using in vitro compartmentalisation (IVC), Nucleic Acids Res 30:4937-4944 (2002).
Lemof, et al, An AC Magnetohydrodynamic Microfluidic Switch for Micro Total Analysis Systems, Biomedical Microdevices, 5(I):55-60 (2003).
Lesley et al., Use of in vitro protein synthesis from PCR-generated templates to study interaction of *E coli* transcription factors with core RNA polymerase, J Biol Chem 266(4):2632-8 (1991).
Lesley, S.A., Preparation and use of *E. coli* S-30 extracts, Methods Mol Biol, 37:265-78 (1995).
Leung et al., A method for random mutagenesis of a defined DNA segment using a modified polymerase chain reaction. Technique 1:11-15 (1989).
Li et al., Single-step procedure for labeling DNA strand breaks with lourescein-or BODIPY-conjugated deoxynucleotides: detection of apoptosis and bromodeoxyuridine incorporation. Cytometry 20:172-180 (1995).
Li and Harrison, Transport, Manipulation, and Reaction of Biological Cells On-Chip Using Electrokinetic Effects, Analytical Chemistry 69(8):1564-1568 (1997).
Li et al., Nanoliter microfluidic hybrid method for simultaneous screening and optimization validated with crystallization of membrane proteins, PNAS 103: 19243-19248 (2006).
Liao et al., Isolation of a thermostable enzyme variant by cloning and selection in a thermophile, PNAS 83:576-80 (1986).
Lim et al., Microencapsulated islets as bioartificial endocrine pancreas, Science 210(4472):908-10 (1980).
Link et al, Geometrically Mediated Breakup of Drops in Microfluidic Devices, Phys. Rev. Lett., 92(5): 054503-1 thru 054503-4 (2004).
Link et al., Electric control droplets in microfluidic devices, Angew Chem Int Ed 45:2556-2560 (2006).
Lipinski et al., Experimental and Computational Approaches to Estimate Solubility and Permeability in Drug Discovery and Development Settings,A.:iv. Drug Deliv. Rev., 46:3-26 (2001).
Lipkin et al., Biomarkers of increased susceptibility to gastreointestinal cancer: new application to studies of cancer prevention in human subjects, Cancer Research 48:235-245 (1988).
Liu et al., Passive Mixing in a Three-Dimensional Serpentine MicroChannel, J MEMS 9(2):190-197 (2000).
Liu et al., Fabrication and characterization of hydrogel-based microvalves, Mecoelectromech. Syst.11:45-53 (2002).
Lizardi et al., Mutation detection and single-molecule counting using isothermal rolling-circle amplification. Nat Genet 19(3):225-32 (1998).
Loakes and Brown, 5-Nitroindole as a universal base analogue. Nucleic Acids Res 22: 4039-4043 (1994).
Loakes et al., Stability and structure of DNA oligonucleotides containing non-specific base analogues. J. Mol. Biol 270:426-435 (1997).
Loeker et al., Colloids and Surfaces A: Physicochem. Eng. Aspects 214: 143-150, 2003).
Lopez-Herrera, et al, {The electrospraying of viscous and non-viscous semi-insulating liquids. Scalilng laws,{ Bulletin of the American Physical Society, vol. 40, No. 12, pp. 2041 (1995).
Lopez-Herrera, et al, {One-Dimensional Simulation of the Breakup of Capillary Jets of Conducting Liquids Application to E.H.D. Spraying,{./. Aerosol. Set, vol. 30, No. 7, pp. 895-912 (1999).
Lopez-Herrera, et al, {Coaxial jets generated from electrified Taylor cones. Scaling laws.,{ Aerosol Science, vol. 34, pp. 535-552 (2003).
Lorenceau et al, Generation of Polymerosomes from Double-Emulsions, Langmuir, 21(20): 9183-9186 (2005).
Lorenz et al, Isolation and expression of a cDNA encoding *Renilla reniformis* luciferase, PNAS 88(10):4438-42 (1991).
Loscertales, et al, Micro/Nano Encapsulation via Electrified Coaxial Liquid Jets, Science, 295(5560): 1695-1698 (2002).
Low N.M. et al., Mimicking somatic hypermutaion: affinity maturation of antibodies displayed on bacteriophage using a bacterila mutator strain. J Mol Biol 260(3), 359-68 (1996).
Lowe, K.C., Perfluorochemical respiratory gas carriers: benefits to cell culture systems, J Fluorine Chem 118:19-26 (2002).
Lowman et al., Selecting high affinity binding proteins by monovalent phage display, Biochemistry 30(45):10832-8 (1991).
Lu et al., Robust fluorescein-doped silica nanoparticles via dense-liquid treatment, Colloids and Surfaces A Physicachemical and Engineering Aspects, 303(3):207-210 (2007).
Luisi et al, Activity and Conformation of Enzymes in Reverse Micellar Solutions, Meth. Enzymol 136:188-216 (1987).
Lund et al., Assesment of methods for covalent binding of nucleic acids to magnetic beads, Dynabeads, and the characteristics of the bound nucleic acids in hybridization reactions, Nucleic Acids Research, Oxford University Press, 16(22) (1998).
Lunderberg et al., Solid-phase technology: magnetic beads to improve nucleic acid detection and analysis, Biotechnology Annual Review, 1:373-401 (1995).
Lundstrom, et al, Breakthrough in cancer therapy: Encapsulation of drugs and viruses, www.currentdrugdiscovery.com, (Nov. 19-23, 2002).
Lyne, P.D., Structure-Based Virtual Screening: An Overview, Drug Discov. Today, 7(20):1047-1055 (2002).
Ma, C. et al., In vitro protein engineering using synthetic tRNA(Ala) with different anticodons, Biochemistry 32(31):7939-45 (1993).
Mackenzie et al., The application of flow microfluorimetry to biomedical research and diagnosis: a review, Dev Biol Stand 64:181-193 (1986).
Maclean, D. et al., Glossary of terms used in combinatorial chemistry, Pure Appl. Chem. 71(12):2349-2365 (1999).
Magdassi et al., Multiple Emulsions: HLB Shift Caused by Emulsifier Migration to External Interface, J. Colloid Interface Sci 97:374-379 (1984).
Mahajan et al., Bcl-2 and Bax Interactions in Mitochondria Probed with Green Florescent Protein and Fluorescence Resonance Energy Transfer, Nat. Biotechnol. 16(6): 547-552 (1998).
Manley et al., In vitro transcription: whole cell extract, Methods Enzymol, 101:568-82 (1983).
Manz et al., Micromachining of monocrystalline silicon and glass for chemical analysis systems A look into next century{s technology or just a fashionable craze?, Trends in Analytical Chemistry 10(5):144-149 (1991).
Mao, Q. et al., Substrate effects on the enzymatic activity of alphachymotrypsin in reverse micelles, Biochem Biophys Res Commun, 178(3):1105-12 (1991).
Mao et al., Kinetic behaviour of alpha-chymotrypsin in reverse micelles: a stopped-flow study, Eur J Biochem 208(1):165-70 (1992).
Mardis, E.R., The impact of next-generation sequencing technology on genetics, Trends Genet 24:133-141 (2008).
Margulies, M et al., Genome sequencing in microfabricated high-density picolitre reactors, Nature 437(7057):376-380 (2005).
Marques et al., Porous Flow within Concentric Cylinders, Bull Am Phys Soc Div Fluid Dyn 41:1768 (1996).
Mason, T.J. and Bibette, J. Shear Rupturing of Droplets in Complex Fluids, Langmuir, 13(17):4600-4613 (1997).
Mastrobattista et al., High-throughput screening of enzyme libraries: in vitro evolution of a beta-galactosidase by fluorescence-activated sorting of double emulsions, Chem. Biol. 12(12): 1291-1300 (2005).
Masui et ai., Probing of DNA-Binding Sites of *Escherichia coli* RecA Protein Utilizing 1-anilinonaphthalene-8-Sulfonic Acid, Biochem 37(35):12133-12143 (1998).
Matayoshi, E.D. et al., Novel fluorogenic substrates for assaying retroviral proteases by resonance energy transfer, Science 247:954 (1990).

(56) References Cited

OTHER PUBLICATIONS

Mattheakis et al., An in vitro polysome display system for identifying ligands from very large peptide libraries, PNAS 91:9022-6 (1994).
Mayr, L.M., and Fuerst, P., The Future of High-Throughput Screening, JBiomol Screen 13:443-448 (2008).
Mazutis et al., Droplet-Based Microfluidic Systems for High-Throughput Single DNA Molecule Isothermal Amplification and Analysis, Anal Chem 81(12):4813-4821 (2009).
Mazutis et al., Multi-step microfluidic droplet processing: kinetic analysis of an in vitro translated enzyme, Lab Chip 9:2902-2908 (2009).
McCafferty et al., Phage antibodies: filamentous phage displaying antibody variable domains,Nature, 348: 552-4 (1990).
McDonald et al. Fabrication of microfluidic systems in poly(dimethylsiloxane), Electrophoresis 21(1):27-40 (2000).
McDonald and Whitesides, Poly(dimethylsiloxane) as a material for fabricating microfluidic devices, Account Chem. Res. 35:491-499 (2002).
Melton et al., Efficient in vitro synthesis of biologically active RNA and RNA hybridization probes from plasmids containing a bacteriophage SP6 promoter, Nucl. Acids Res. 12(18):7035-7056 (1984).
Mendel, D. et al., Site-Directed Mutagenesis with an Expanded Genetic Code, Annu Rev Biophys Biomol Struct, 24:435-62 (1995).
Menger and Yamada, Enzyme catalysis in water pools, J. Am. Chem. Soc., 101:6731-4 (1979).
Meylan and Howard, Atom/fragment contribution method for estimating octanol-water partition coefficients, J Pharm Sci. 84(1):83-92 (1995).
Miele et al., Autocatalytic replication of a recombinant RNA, J Mol Biol, 171:281-95 (1983).
Minshuil, J. and Stemmer, W.P., Protein evolution by molecular breeding, Curr Opin Chem Biol 3(3): 284-90 (1999).
Miroux and Walker, Over-production of proteins in *Escherichia coli*: mutant hosts that allow synthesis of some membrane proteins and globular proteins at high levels, J of Mol Biol 260(3):289-98 (1996).
Miyawaki at at., Fluorescent Indicators for Ca2+ Based on Green Fluorescent Proteins and Calmodulin, Nature, 388: 882-887 (1997).
Mize et al., Dual-enzyme cascade—an amplified method for the detection of alkaline phosphatase, Anal Biochem 179(2): 229-35 (1989).
Mock et al., A fluorometric assay for the biotin-avidin interaction based on displacement of the fluorescent probe 2-anilinonaphthalene-6-sulfonic acid, Anal Biochem, 151:178-81 (1985).
Moldavan, A., Photo-electric technique for the counting of microscopical cells, Science 80:188-189 (1934).
Montigiani, S. et al., Alanine substitutions in calmodulin-binding peptides result in unexpected affinity enhancement, J Mol Biol, 258:6-13 (1996).
Moore, M.J., Exploration by lamp light, Nature, 374:766-7 (1995).
Moudrianakis and Beer, Base sequence determination in nucelic acids with the electron microscope 3. Chemistry and microscopy of guanine-labeled DNA, PNAS 53:564-71 (1965).
Mudler et al., Characterization of tWO human monoclonal antibodies reactive with HLA-B12 and HLA-B60, respectively, raised by in vitro secondary immunization of peripheral blood lymphocytes, Hum. Immunol., 36(3):186 192, 1993.
Mulbry, W.W. et al., Parathion hydrolase specified by the *Flavobacterium* opd gene: relationshio between the gene and protein. J Bacteriol, 171: 6740-6746 (1989).
Nakano et al., Single-molecule reverse transcription polymerase chain reaction using water-in-oil emulsion, J Biosci Bioeng 99:293-295 (2005).
Nakano et al., Single-molecule PCR using water-in-oil emulsion, J Biotech, 102:117-24 (2003).
Nametkin, S.N. et al., Cell-free translation in reversed micelles, FEB Letters, 309(3):330-32.
Narang et al, Improved phosphotriester method for the synthesis of gene fragments, Methods Enzymol, 68:90-98 (1979).

Nelson, P. S., et al., Bifunctional oligonucleotide probes synthesized using a novel CPG support are able to detect single base pair mutations, Nucl Acids Res 17(18): 7187-7194 (1989).
Nemoto et al., In vitro virus: bonding of mRNA bearing puromycin at the 3{-terminal end to the C-terminal end of its encoded protein on the ribosome in vitro, Federation of European Biochemical Societies, 414:405-8 (1997).
Ness, J.E. et al., Molecular Breeding: the natural approach to protein design. Adv Protein Chem, 55: 261-292 (2000).
Ng et al., Protein crystallization by capillary counter-diffusion for applied crystallographic structure determination, J. Struct. Biol. 2003, v142, pp. 218-231.
Ng, B.L. et al., Factors affecting flow karyotype resolution, Cytometry, Part A 69A: 1028-1036 (2006).
Nguyen et al., Optical detection for droplet size control in microfluidic droplet-based analysis systems, Sensors and Actuators B 117(2):431-436 (2006).
Nihant et al., Polylactide Microparticles Prepared by Double Emulsion/Evaporation Technique. I. Effect of Primary Emulsion Stability, Pharmaceutical Research, 11(10):1479-1484 (1994).
Nisisako, Takasi et al., Droplet Formation in a MicroChannel NetWOrk, Lab on a Chip, vol. 2, 2002, pp. 24-26.
Nisisako et al., Formation of droplets using branch channels in a microfluidic circuit, Proceedings of the SICE Annual Conference. International Session Papers 1262-1264 (2002).
Nisisako et al., Controlled formulation of monodisperse double emulsions in a multiple-phase microluidic system, Sot Matter, 1:23-27 (2005).
Nisisako et al., Microstructuerd Devices for Preparing Controlled Multiple Emulsions. Chem. Eng. Technol 31(8):1091-1098 (2008).
Nissim, A. et al., Antibody fragments from a {single pot{ phage display library as immunochemical reagents, Embo J, 13:692-8 (1994).
Nof and Shea, Drug-releasing scaffolds fabricated from drug-loaded microspheres, J. Biomed Mater Res 59:349-356 (2002).
Norman, A., Flow Cytometry, Med. Phys., 7(6):609-615 (1980).
Oberholzer et al., Enzymatic RNA replication in self-reproducing vesicles: an approach to a minimal cell, Biochem Biophys Res Commun 207(1):250-7 (1995).
Oberholzer et al., Polymerase chain reaction in liposomes, Chem. Biol. 2(10):677-82 (1995).
Obukowicz, M.G. et al., Secretion and export of IGF-1 in *Escerichia coli* strain JM101, Mol Gen Genet, 215:19-25 (1988).
Ogura, Y., Catalase activity at high concentrations of hydrogen peroxide, Archs Biochem Biophys, 57: 288-300 (1955).
Oh et al., Distribution of Macropores in Silica Particles Prepared by Using Multiple Emulsions, Journal of Colloid and Interface Science, 254(1): 79-86 (2002).
Okushima et al. Controlled production of monodisperse double emulsions by tWO-step droplet breakup in microfluidic devices, Langmuir 20(23): 9905-8 (2004).
Olsen et ai., Function-based isolation of novel enzymes from a large library, Nat Bioteoltnol 13(10):1071-4 (2000).
Omburo, G.A. et al., Characterization of the zinc binding site of bacterial phosphotriesterase, J of Biological Chem, 267:13278-83 (1992).
Oroskar et al., Detection of immobilized amplicons by ELISA-like techniques, Clin. Chem. 42:1547-1555 (1996).
Ostermeier, M. et al., A combinatorial approach to hybrid enzymes independent of DNA homology, Nat Biotechnol, 17(12):1205-9 (1999).
Ouelette, A new wave of microfluidic devices, Indust Physicist pp. 14-17 (2003).
Pabit et al., Laminar-Flow Fluid Mixer for Fast Fluorescence Kinetics Studies, Biophys J 83:2872-2878 (2002).
Paddison et al., Stable suppression of gene expression by RNAi in mammalian cells, PNAS 99(3):1443-1448 (2002).
Pannacci et al., Equilibrium and Nonequilibrium States in Microluidic Double Emulsions Physical Review Leters, 101(16):164502 (2008).
Park et al., Cylindrical compact thermal-cycling device for continuous-flow polymeras chain reaction, Anal Chem, ACS, 75:6029-33 (2003).

(56) References Cited

OTHER PUBLICATIONS

Park et al., Model of Formation of Monodispersed Colloids, J. Phys. Chem. B 105:11630-11635 (2001).
Parker et al., Development of high throughput screening assays using fluorescence polarization: nuclear receptor-ligand-binding and kinase/phosphatase assays, J Biomol Screen, 5(2): 77-88 (2000).
Parmley et al., Antibody-selectable filamentous fd phage vectors: affinity purification of target genes. Gene 73(2):305-18 (1988).
Pedersen et al., A method for directed evolution and functional cloning of enzymes, PNAS 95(18):10523-8 (1998).
Pelham and Jackson, An efficient mRNA-dependent translation system from reticulocyte lysates, Eur J Biochem 67:247-56 (1976).
Pelletier et al., An in vivo library-versus-library selection of optimized protein-protein interactions, Nature Biotechnology, 17:683-90 (1999).
Peng et al., Controlled Production of Emulsions Using a Crossflow Membrane, Particle & Particle Systems Characterization 15:21-25 (1998).
Perelson et al., Theoretical studies of clonal selection: minimal antibody repertoire size and relaibility of self-non-self discrimination. J Theor Biol 81(4):645-70 (1979).
Perez-Gilabert et al., Application of active-phase plot to the kinetic analysis of lipoxygenase in reverse micelles, Biochemistry J. 288:1011-1015 (1992).
Perrin, J., Polarisation de la lumiere de fluorescence vie moyenne des molecules dans I{etat excite, J. Phys. Rad. 1:390-401 (1926).
Petrounia, I.P. et al., Designed evolution of enzymatic properties, Curr Opin Biotechnol, 11:325-330 (2000).
Piemi et al., Transdermal delivery of glucose through hairless rat skin in vitro: effect of multiple and simple emulsions, Int J Pharm, 171:207-215 (1998).
Pirrung et al., A General Method for the Spatially De?ned Immobilization of Biomolecules on Glass Surfaces Using 'Caged' Biotin, Bioconjug Chem 7: 317-321 (1996).
Ploem, in Fluorescent and Luminescent Probes for Biological Activity Mason, T. G. Ed., Academic Press, Landon, pp. 1-11, 1993.
Pluckthun, A. et al., In vitro selection and evolution of proteins, Adv Protein Chem, 55: 367-403 (2000).
Pollack et al., Electrowetting-based actuation of droplets for integrated microfluidics, Lab Chip 2:96-101 (2002).
Pollack et al., Selective chemical catalysis by an antibody, Science 234(4783):1570-3 (1986).
Pons et al, Synthesis of Near-Infrared-Emitting, Water-Soluble CdTeSe/CdZnS Core/Shell Quantum Dots, Chemistry of Materials 21(8):1418-1424 (2009).
Posner et al., Engineering specificity for folate into dihydrofolate reductase from *Escherichia coli*, Biochemistry, 35: 1653-63 (1996).
Poulin and Theil A priori prediction of tissue: plasma partition coefficients of drugs to facilitate the use of physiologically-based pharmokinetic models in drug discovery, J Pharm Sci 89(1):16-35 (2000).
Priest, et al. Generation of Monodisperse Gel Emulsions in a Microfluidic Device, Applied Physics Letters, 88:024106 (2006).
Qi et al., Acid Beta-Glucosidase: Intrinsic Fluorescence and Conformational Changes Induced by Phospholipids and Saposin C, Biochem., 37(33): 11544-11554 (1998).
Raghuraman et al., Emulston Liquid Membranes for Wastewater Treatment: Equillibrium Models for Some Typical Metal-Extractant Systems,Environ. Sci. Technol 28:1090-1098 (1994).
Ralhan, Discovery and Verification of Head-and-neck Cancer Biomarkers by Differential Protein Expression Analysis Using iTRAQ Labeling, Multidimensional Liquid Chromatography, and Tandem Mass Spectrometry, Mol Cell Proteomics 7(6):1162-1173 (2008).
Ramsey, J.M., The burgeoning power of the shrinking laboratory, Nat Biotechnol 17(11):1061-2 (1999).
Ramstrom and Lehn, Drug discovery by dynamic combinatorial libraries, Nat Rev Drug Discov 1:26-36 (2002).
Raushel, F.M. et al., Phosphotriesterase: an enzyme in search of its natural substrate, Adv Enzymol Relat Areas Mol Biol, 74: 51-93 (2000).
Rech et al., Introduction of a yeast artificial chromosome vector into *Sarrachomyeces cervesia* by electroporation, Nucleic Acids Res 18:1313 (1990).
Reyes et al., Micro Total Analysis Systems. 1. Introduction, Theory and Technology, Anal Chem 74(12):2623-2636 (2002).
Riess, J.S., Fluorous micro- and nanophases with a biomedical perspective, Tetrahedron 58(20):4113-4131 (2002).
Roach et al., Controlling nonspeci?c protein adsorption in a plug-based micro?uidic system by controlling inteifacial chemistry using ?uorous-phase surfactants, Anal. Chem. 77:785-796 (2005).
Roberts, J.W.,Termination factor for RNA synthesis, Nature, 224: 1168-74 (1969).
Roberts et al., Simian virus 40 DNA directs synthesis of authentic viral polypeptides in a linked transcription-translation cell-free system 72(5):1922-1926 (1975).
Roberts, et al., RNA-peptide fusion for the in vitro selection of peptides and proteins, PNAS 94:12297-302 (1997).
Roberts, R.W. Totally in vitro protein selection using mRNA-protein fusions and ribosome display. Curr Opin Chem Biol 3(3), 268-73 (1999).
Roberts & Ja, In vitro selection of nucleic acids and proteins: What are we learning?, Curr Opin Struct Biol 9(4): 521-9 (1999).
Rodriguez-Antona et al., Quantitative RT-PCR measurement of human cytochrome P-450s: application to drug induction studies. Arch. Biochem. Biophys., 376:109-116 (2000).
Rolland et al., Fluorescence Polarization Assay by Flow Cytometry, J. Immunol. Meth., 76(1): 1-10 (1985).
Rosenberg et al.,Termination of transcription in bacteriophage lambda, J Biol Chem, 250: 4755-64 (1975).
Rosenberry, T.L., Acetylcholinesterase, Adv Enzymol Relat Areas Mol Biol, 43: 103-218 (1975).
Rotman, Measurement of activities of single molecules of beta-galactosidase, PNAS, 47:1981-91 (1961).
Russon et al., Single-nucleotide polymorphism analysis by allele-specific extension of fluorescently labeled nucleotides in a microfluidic flow-through device, Electrophoresis, 24:158-61 (2003).
Sadtler et al., Achieving stable, reverse water-in-fluorocarbon emulsions. Angew Chem Int Ed 35:1976-1978 (1996).
Saiki, R.K, et al, Primer directed enzymatic amplification of DNA with a thermostable DNA polymerase. Science 239(4839):487-91 (1988).
Sanchez et al., Breakup of Charged Capillary Jets, Bulletin of the American Physical Society Division of Fluid Dynamics 41:1768-1768 (1996).
Sano, T. et al., Immuno-PCR-Very sensitive antigen-detection by means of sepcific antibody-DNA conjugates. Science 258(5079), 120-122 (1992).
SantaLucia, A unified view of polymer, dumbbell, and oligonucleotide DNA nearest-neighbor thermodynamics, PNAS 95(4):1460-5 (1998).
Santra et al., Fluorescence lifetime measurements to determine the core-shell nanostructure of FITC-doped silica nanoparticles: An optical approach to evaluate nanoparticle photostability, J Luminescence 117(1):75-82 (2006).
Schatz et al., Screening of peptide libraries linked to lac repressor, Methods Enzymol 267: 171-91 (1996).
Schneegass et al., Miniaturized flow-through PCR with different template types in a silicone chip thermocycler, Lab on a Chip, Royal Soc of Chem, 1:42-9 (2001).
Schubert et al., Designer Capsules, Nat Med 8:1362 (2002).
Schweitzer et al., Immunoassays with rolling circle DNA amplification: A versatile platform for ultrasensitive antigen detection, PNAS 97(18), 10113-10119 (2000).
Schweitzer, B. et al., Combining nucleic acid amplification and detection. Curr Opin Biotechnol 12(1):21-7 (2001).
Scott, R.L., The Solubility of Fluorocarbons, J. Am. Chem. Soc, 70: 4090-4093 (1948).

(56) References Cited

OTHER PUBLICATIONS

Seethala and Menzel, Homogeneous, Fluorescence Polarization Assay for Src-Family Tyrosine Kinases, Anal Biochem 253(2):210-218 (1997).
Seiler et al., Planar glass chips for capillary electrophoresis: repetitive sample injection, quantitation, and separation efficiency, Anal Chem 65(10):1481-1488 (1993).
Selwyn M. J., A simple test for inactivation of an enzyme during assay, Biochim Biophys Acta 105:193-195 (1965).
Seo et al., Microfluidic consecutive flow-focusing droplet generators, Soft Matter, 3:986-992 (2007).
Seong et al., Fabrication of Microchambers Defined by Photopolymerized Hydrogels and Weirs Within Microfluidic Systems: Application to DNA Hybridization, Analytical Chem 74(14):3372-3377 (2002).
Seong and Crooks, Efficient Mixing and Reactions Within Microfluidic Channels Using Microbead-Supported Catalysts, J Am Chem Soc 124(45):13360-1 (2002).
Sepp et al., Microbead display by in vitro compartmentalisation: selection for binding using flow cytometry, FEBS Letters 532:455-58 (2002).
Serpersu et al., Reversible and irreversible modification of erythrocyte membranse permeability by electric field, Biochim Biophys Acta 812(3):779-785 (1985).
Shapiro, H.M., Multistation multiparameter flow cytometry: a critical review and rationale, Cytometry 3: 227-243 (1983).
Shestopalov et al., Multi-Step Synthesis of Nanoparticles Performed on Millisecond Time Scale in a Microfluidic Droplet-Based System, The Royal Society of Chemistry 4:316-321, 2004.
Shtern V, and Hussain F., Hysteresis in swirling jets, J. Fluid Mech. 309:1-44 (1996).
Sia &Whitesides, Micro?uidic devices fabricated in poly(dimethylsiloxane) for biological studies, Electrophoresis 24(21):3563-3576 (2003).
Sidhu, S.S., Phage display in pharmaceutical biotechnology, Curr Opin Biotech 11:610-616 (2000).
Siemering et al., Mutations that suppress the thermosensitivity of green fluorescent protein, Current Biology 6:1653-1663 (1996).
Silva-Cunha et al., W/O/W multiple emulsions of insulin containing a protease inhibitor and an absorption enhancer: biological activity after oral administration to normal and diabetic rats, Int J Pharm 169:33-44 (1998).
Sims et al., Immunopolymerase chain reaction using real-time polymerase chain reaction for detection, Anal. Biochem. 281(2):230-2 (2000).
Slappendel et al., Normal cations and abnormal membrane lipids in the red blood cells of dogs with familial stomatocytosis hypertrophic gastritis, Blood 84:904-909 (1994).
Slob et al., Structural identifiability of PBPK models: practical consequences for modeling strategies and study designs, Crit Rev Toxicol. 27(3):261-72 (1997).
Smith et al., The synthesis of oligonucleotides containing an aliphatic amino group at the 5{ terminus: synthesis of fluorescent DNA primers for use in DNA sequence analysis, Nucl. Acid Res. 13:2399-2412 (1985).
Smith G.P., Filamentous fusion phage: novel expression vectors that display cloned antigens on the virion surface, Science 228(4705): 1315-7(1985).
Smith et al., Fluorescence detection in automated DNA sequence analysis, Nature 321:674-679 (1986).
Smith et al., Direct mechanical measurements of the elasticity of single DNA molecules by using magnetic beads, Science 258(5085):1122-1126 (1992).
Smith et al., Phage display, Chemical Reviews 97(2), 391-410 (1997).
Smyth et al., Markers of apoptosis: methods for elucidating the mechanism of apoptotic cell death from the nervous system, Biotechniques 32:648-665 (2000).
Sohn, et al, Capacitance cytometry: Measuring biological cells one by one, PNAS 97(20):10687-10690 (2000).
Somasundaram and Ramalingam, Gain studies of Rhodamine 6G dye doped polymer laser, J Photochem Photobiol 125(1-3):93-98 (1999).
Song, H. and Ismagilov, R.F., Millisecond kinetics on a microluidic chip using nanoliters of reagents, J Am Chem Soc. 125: 14613-14619 (2003).
Song et al., A microfluidic system for controlling reaction netWO rks in time, Angew. Chem. Int. Ed. 42(7):768-772 (2003).
Song et al., Experimental Test of Scaling of Mixing by Chaotic Advection in Droplets Moving Through Microfluidic Channels, App Phy Lett 83(22):4664-4666 (2003).
Soni and Meller, Progress toward ultrafast DNA sequencing using solid-state nanopores, Clin Chem 53:1996-2001 (2007).
Soumillion et al., Selection of B-lactomase on filamentous bacteriophage by catalytic activity, J Mol Biol, 237:415-22 (1994).
Soumillion et al., Novel concepts for the selection of catalytic activity. Curr Opin Biotechnol 12:387-394 (2001).
Sproat et al., The synthesis of protected 5'-mercapto-2',5'-dideoxyribonucleoside-3'-0-phosphorainidites, uses of 5'-mercapto-oligodeoxyribonucleotides, Nucleic Acids Res 15:4837-4848 (1987).
Stauber, et a., Rapid generation of monoclonal antibody-secreting hybridomas against African horse sickness virus by in vitro immunization and the fusion/cloning technique, J. Immunol. Meth 161(2):157-168 (1993).
Stemmer, W.P., DNA shuffling by random fragmentation and reassembly: in vitro recombination for molecular evolution. PNAS 91(22):10747-51(1994).
Stemmer, W.P., Rapid evolution of a protein in vitro by DNA shuffling, Nature 370(6488):389-91 (1994).
Stober et al., Controlled growth of monodisperse silica spheres in the micron size range, J Colloid and Interface Sci 26(1):62-69 (1968).
Stofko, H.R. et al., A single step purification for recombinant proteins. Characterization of microtube associated protein (MAP2) fragment which associates with the type II cAMP-dependent protein kinase, Febs Lett 302: 274-278 (1992).
Strizhkov et al., PCR amplification on a microarray of gel-immobilized oligonucleotides: Detection of bacterial toxin- and drug-resistant genes and their mutations, BioTechniques 29(4):844-857 (2000).
Stroock et al., Chaotic mixer for microchannels, Science 295(5555):647-651 (2002).
Studer et al., Fluorous Synthesis: A Fluorous-Phase Strategy for Improving Separation Efficiency in Organic Synthesis, Science 275: 823-826 (1997).
Sugiura et al., Effect of Channel Structure on MicroChannel Emuisification, Langmuir 18:5708-5712 (2002).
Sugiura et al., Interfacial tension driven monodispersed droplet formation from mtcrofabricated channel array Langmuir, 17: 5562-5566 (2001).
Sundberg et al., Spatially-Addressable Immobilisation of Macromolecules on Solid Supports, J. Am. Chem. Soc, 117:12050-12057 (1995).
Suzuki et al., Random mutagenesis of *Thermus aquaticus* DNA polmerase I: concordance of immutable sites in vivo with the crystal structure, PNAS USA, 93:96701-9675 (1996).
Szostak, J.W., In vitro selection of functional nucleic acids. Ann. Rev. Biochem. 68, 611-647 (1999).
Takayama et al., Patterning Cells and Their Environments Using Multiple Laminar Fluid Flows in Capillary NetWO rks, PNAS 96:5545-5548 (1999).
Takeuchi et al., An Axisymmetric Flow-Focusing Microfluidic Device, Adv. Mater 17(8):1067-1072 (2005).
Tan, Y.C., Monodisperse Droplet Emulsions in Co-Flow Microfluidic Channels, Micro TAS, Lake Tahoe (2003).
Tan, Y.C., Microfluidic Liposome Generation from Monodisperse Droplet Emulsion—Towards the Realization of Artificial Cells, Summer Bioengineering Conference, Florida (2003).
Tan et al., Controlled Fission of Droplet Emulsions in Bifurcating Microfluidic Channels, Transducers Boston (2003).
Tan et al., Design of microluidic channel geometries for the control of droplet volume, chemical concentration, and sorting, Lab Chip, 4(4): 292-298 (2004).

(56) References Cited

OTHER PUBLICATIONS

Tan et al., Monodispersed micro?uidic droplet generation by shear focusing micro?uidic device, Sensors and Actuators 114:350-356 (2006).
Tanaka et al., Ethanol Production from Starch by a Coimmobilized Mixed Culture System of *Aspergillus awamori* and *Zymomonas mobilis*, Biotechnol Bioeng XXVII:1761-1768 (1986).
Tang et al., A multi-color fast-switching microfluidic droplet dye laser, Lab Chip 9:2767-2771 (2009).
Taniguchi et al., Chemical Reactions in Microdroplets by Electrostatic Manipulation of Droplets in Liquid Media, Lab on a Chip 2:19-23 (2002).
Tawfik et al., catELISA: a facile general route to catalytic antibodies, PNAS 90(2):373-7 (1993).
Tawfik, D.S. et al., 1,8-diabycyclo[5.4.0]undecane mediated transesterification of p-nitrophenyl phosphonates—a novel route to phosphono esters, Synthesis-Stuttgart, 10: 968-972 (1993).
Tawfik et al., Efficient and selective p-nitrophenyl-ester=hydrolyzing antibodies elicited by a p-nitrobenzyl phosphonate hapten, Eur J Biochem, 244:619-26 (1997).
Tawfik et al., Man-made cell-like compartments for molecular evolution, Nature Biotechnology, 7(16):652-56 (1998).
Taylor et al., Characterization of chemisorbed monolayers by surface potential measurments, J. Phys. D. Appl. Phys. 24:1443 (1991).
Tchagang et al., Early detection of ovarian cancer using group biomarkers, Mol Cancer Ther 7:27-37 (2008).
Tencza et al., Development of a Fluorescence Polarization-Based Diagnostic Assay for Equine Infectious Anemia Virus, J Clinical Microbiol 38(5):1854-185 (2000).
Terray, et al, Fabrication of linear colloidal structures for microfluidic applications, Applied Phys Lett 81(9):1555-1557 (2002).
Terray et al., Microluidic Control Using Colloidal Devices,Science, 296(5574):1841-1844 (2002).
Tewhey et al., Microdroplet-based PCR amplification for large scale targeted sequencing, Nat Biotechnol 27(11):1025-1031 (2009).
Thompson, L.F., Introduction to Lithography, ACS Symposium Series 219:1-13, (1983).
Thorsen et al., Dynamic pattern formation in a vesicle-generating microfluidic device, Phys Rev Lett 86(18):4163-4166 (2001).
Thorsen et al., Microfluidic Large-Scale Integration, Science 298:580-584 (2002).
Tice et al., Formation of droplets and mixing in multiphase microfluidics at low values of the reynolds and the capillary numbers, Langmuir 19:9127-9133 (2003).
Tice et al., Effects of viscosity on droplet formation and mixing in microfluidic channels, Analytica Chimica Acta 507:73-77 (2004).
Titomanlio et al., Capillary experiments of flow induced crystallization of HOPE{, AlChe Journal, 1990, v36, No. 1, pp. 13-18.
Tleugabulova et al., Evaluating formation and growth mechanisms of silica particles using fluorescence anisotropy decay analysis, Langmuir 20(14):5924-5932 (2004).
Tokatlidis et al., Nascent chains: folding and chaperone intraction during elongation on ribosomes, Philos Trans R Soc Lond B Biol Sci, 348:89-95 (1995).
Tokeshi et al., Continuous-Flow Chemical Processing on a Microchip by Combining Microunit Operations and a Multiphase Flow NetWO rk, Anal Chem 74(7):1565-1571 (2002).
Tokumitsu, H. et al., Preparation of gadopentetic acid-loaded chitosan microparticles for gadolinium neutron-capture therapy of cancer by a novel emulsion-droplet coalescence technique, Chem and Pharm Bull 47(6):838-842 (1999).
Tramontano, A., Catalytic antibodies, Science 234(4783):1566-70 (1986).
Trindade, T., Nanocrystalline semiconductors: synthesis, properties, and perspectives, Chem. Mat. 13:3843-3858 (2001).
Tripet, B. et al., Engineering a de novo-designed coiled-coil heterodimerization domain off the rapid detection, purification and characterization of recombinantly expressed peptides and proteins, Protein Engng., 9:1029-42 (1996).
Tuerk, C. and Gold, L., Systematic Evolution of Ligands by Exponentid Enrichment: RNA Ligands to Bacteriophage T4 DNA Polymerase, Science, 249:505-10 (1990).
Umbanhowar et al., Monodisperse Emulsion Generation via Drop Break Off in a Coflowing Stream, Langmuir 16(2):347-351 (2000).
Unger et al., Monolithic microfabricated valves and pumps by multylayer soft lithography, Science 288(5463):113-116 (2000).
Utada, A. et al., Monodisperse double emulsions generated from a microcapillary device, Science, 308:537-541 (2005).
Vainshtein et al., Peptide rescue of an N-terminal truncation of the stoffel fragment of Taq DNA polymerase, Protein Science, 5:1785-92 (1996).
Van Bockstaele et al., Prognostic markers in chronic lymphocytic leukemia: a comprehensive review, Blood Rev 23(1):25-47 (2009).
Van Dilla et al., The fluorescent cell photometer: a new method for the rapid measurement of biological cells stained with fluorescent dyes, Annual Report of the Los Alamos Scientific Laboratory of the University of California (Los Alamos, NM), Biological and Medical Research Groupp (H-4) of the Health Division, Compiled by D. G. Ott, pp. 100-105, distributed Jan. 23, 1968.
Van Dilla et al., Cell Microfluorometry: A Method for Rapid Fluorescence Measurement, Science 163(3872):1213-1214 (1969).
Vanhooke et al., Three-dimensional structure of the zinc-containing phosphotrieesterase with the bound substrate analog diethy 4-methylbenzylphosphonate, Biochemistry 35:6020-6025 (1996).
Varga, J.M. et al., Mechanism of allergic cross-reactions-I. Multispecific binding of ligands to a mouse monoclonal anti-DNP IgE antibody. Mol Immunol 28(6), 641-54 (1991).
Vary, A homogeneous nucleic acid hybridization assay based on strand displacement, Nucl Acids Res 15(17):6883-6897 (1987).
Venkateswaran et al., Production of Anti-Fibroblast Growth Factor Receptor Monoclonal Antibodies by In Vitro Immunization, Hybirdoma, 11(6):729-739 (1992).
Venter et al., The sequence of the human genome, Science 291(5507):1304-51 (2001).
Vogelstein et al., Digital PCR, PNAS 96(16):9236-9241 (1999).
Voss, E.W., Kinetic measurements of molecular interactions by spectrofluorometry, J Mol Recognit, 6:51-58 (1993).
Wahler, D. et al., Novel methods for biocatalyst screening. Curr Opin Chem Biol, 5: 152-158 (2001).
Walde, P. et al., Structure and activity of trypsin in reverse micelles, Eur J Biochem, 173(2):401-9 (1988).
Walde, P. et al., Spectroscopic and kinetic studies of lipases solubilized in reverse micelles, Biochemistry, 32(15):4029-34 (1993).
Walker et al., Strand displacement amplification—an isothermal, in vitro DNA amplification technique, Nucleic Acid Res, 20(7):1691-6 (1992).
Walker et al., Isothermal in vitro amplification of DNA by a restriction enzyme/DNA polymerase system, PNAS 89(1):392-6 (1992).
Wang, A.M. et al., Quantitation of mRNA by the polymerase chain reaction. Proc natl Acad Sci USA 86(24), 9717-21 (1989).
Wang, G.T. et al., Design and synthesis of new fluorogenic HIV protease substrates based on resonance energy transfer, Tetrahedron Lett., 31:6493 (1990).
Wang et al., Preparation of Titania Particles Utilizing the Insoluble Phase Interface in a MicroChannel Reactor, Chemical Communications 14:1462-1463 (2002).
Wang et al., DEP actuated nanoliter droplet dispensing using feedback control, Lab on a Chip 9:901-909 (2008).
Warburton, B., Microcapsules for Multiple Emulsions, Encapsulation and Controlled Release, Spec Publ R Soc Chem, 35-51 (1993).
Weil. et al., Selective and accurate initiation of transcription at the Ad2 major late promotor in a soluble system dependent on purified RNA polymerase II and DNA, Cell, 18(2):469-84 (1979).
Wetmur et al., Molecular haplotyping by linking emulsion PCR: analysis of paraoxonase 1 haplotypes and phenotypes, Nucleic Acids Res 33(8):2615-2619 (2005).
Wick et al., Enzyme-containing liposomes can endogenously produce membrane-constituting lipids, Chem Biol 3(4):277-85 (1996).
Widersten and Mannervik, Glutathione Transferases with Novel Active Sites Isolated by Phage Display from a Library of Random Mutants, J Mol Biol 250(2):115-22 (1995).

(56) References Cited

OTHER PUBLICATIONS

Wiggins et al., Foundations of chaotic mixing, Philos Transact A Math Phys Eng Sci 362(1818):937-70 (2004).
Williams et al., Methotrexate, a high-affinity pseudosubstrate of dihydrofolate reductase, Biochemistry, 18(12):2567-73 (1979).
Williams et al., Amplification of complex gene libraries by emulsion PCR, Nature Methods 3(7):545-550 (2006).
Wilson, D.S. and Szostak, J.W., In vitro selection of functional nucleic acids, Ann. Rev. Biochem. 68: 611-647 (1999).
Winter et al., Making antibodies by phage display technology, Annu Rev Immunol 12:433-55 (1994).
Wittrup, K.D., Protein engineering by cell-surface display. Curr Opin Biotechnology, 12: 395-399 (2001).
Wolff et al., Integrating advanced functionality in a microfabricated high-throughput fluorescent-activated cell sorter, Lab Chip, 3(1): 22-27 (2003).
Wronski et al., Two-color, fluorescence-based microplate assay for apoptosis detection. Biotechniques, 32:666-668 (2002).
Wu et al., The ligation amplification reaction (LAR)-amplification of specific DNA sequences using sequential rounds of template-dependent ligation, Genomics 4(4):560-9 (1989).
Wyatt et al., Synthesis and purification of large amounts of RNA oligonucleotides, Biotechniques 11(6):764-9 (1991).
Xia and Whitesides, Soft Lithography, Angew. Chem. Int. Ed. 37:550-575 (1998).
Xia and Whitesides, Soft Lithography, Ann. Rev. Mat. Sci. 28:153-184 (1998).
Xu, S. et al., Generation of monodisperse particles by using microfluidics: control over size, shape, and composition, Angew. Chem. Int. Ed. 44:724-728 (2005).
Yamagishi, J. et al., Mutational analysis of structure-activity relationships in human tumor necrosis factor-alpha, Protein Eng, 3:713-9 (1990).
Yamaguchi et al., Insulin-loaded biodegradable PLGA microcapsules: initial burst release controlled by hydrophilic additives, Journal of Controlled Release, 81(3): 235-249 (2002).
Komatsu et al., Roles of cytochromes P450 1A2, 2A6, and 2C8 in 5-fluorouracil formation rom tegafur, an anticancer prodrug, in human liver microsomes. Drug Met. Disp., 28:1457-1463 (2001).
Yershov et al., DNA analysis and diagnostics on oligonucleotide microchips, PNAS 93(10):4913-4918 (1996).
Yonezawa et al., DNA display for in vitro selection of diverse peptide libraries, Nucleic Acids Research, 31(19): e118 (2203).
Yu et al., Specific inhibition of PCR by Non-Extendable Oligonucleotides Using a 5' to 3' Exonuclease-Defcient DNA Polymerase, Biotechniques 23(4):714-6, 718-20 (1997).
Yu et al. Responsive biomimetic hydrogel valve for microfluidics. Appl. Phys. Lett 78:2589-2591 (2001).
Yu et al., Quantum dot and silica nanoparticle doped polymer optical fibers, Optics Express 15(16):9989-9994 (2007).
Zaccolo, M. et al., An approach to random mutagenesis of DNA using mixtures of triphosphate derivatives of nucleoside analogues. J Mol Biol 255(4):589-603 (1996).
Zakrzewski, S.F., Preparation of tritiated dihydrofolic acid of high specific activity, Methods Enzymol, 539 (1980).
Zaug and Cech, The *Tetrahymena* intervening sequence ribonucleic acid enzyme is a phosphotransferase and an acid phosphatase, Biochemistry 25(16):4478-82 (1986).
Zaug et al., The *Tetrahymena* ribozyme acts like an RNA restriction endonuclease, Nature 324(6096):429-33 (1986).
Zaug and Cech, The intervening sequence RNA of *Tetrahymena* is an enzyme, Science 231(4737):470-5 (1986).
Zhang, Z.Y., Substrate specificity of the protein tyrosine phosphatases, PNAS 90: 4446-4450 (1993).
Zhang et al., A Simple Statistical Parameter for Use in Evaluation and Validation of High Throughput Screening Assays, Journal of Biomolecular Screening, 4(2): 67-73 (1999).
Zhao, H. et al., Molecular evolution by staggered extension process (StEP) in vitro recombination. Nat Biotechnol 16(3):258-61 (1998).
Zhao, B. et al., Control and Applications of Immiscible Liquids in Microchannels, J. Am. Chem. Soc, vol. 124:5284-5285 (2002).
Zheng et al., Screening of Protein Crystallization Conditions on a Microfluidic Chip Using Nanoliter-Size Droplets, J Am Chem Soc 125(37):11170-11171 (2003).
Zheng et al., Formation of Droplets of Alternating Composition in Microfluidic Channels and Applications to Indexing of Concentrations in Droplet-Based /Assays, Anal. Chem., 2004, v. 76, pp. 4977-4982.
Zheng et al., A Droplet-Based, Composite PDMS/Glass Capillary Microfluidic System for Evaluating Protein Crystallization Conditions by Microbatch and Vapor-Diffusion Methods with On-Chip X-Ray Diffraction, Angew. Chem., pp. 1-4, 2004.
Zheng et al., A Microiuidic Approach for Screening Submicroliter Volumes against Multiple Reagents by Using Performed Arrays of Nanoliter Plugs in a Three-Phase Liquid/Liquid/Gas Flow, Angew. Chem. Int. Ed., 44(17): 2520-2523 (2005).
Zimmermann et al., Dielectric Breakdown of Cell Membranes, Biophys J 14(11):881-889 (1974).
Zimmermann et al., Microscale Production of Hybridomas by Hypo-Osmolar Electrofusion, Hum. Antibod. Hybridomas, 3(1): 14-18 (1992).
Zubay, G., In vitro synthesis of protein in microbial systems, Annu Rev Genet, 7: 267-87 (1973).
Zubay, G., The isolation and properties of CAP, the catabolite gene activator, Methods Enzymol, 65: 856-77 (1980).
Zuckermann, R. et al., Efficient Methods for Attachment of Thiol-Specific Probes to the 3{-end of Synthetic Oligodeoxyribonucleotides, Nucleic Acids Res. 15:5305-5321 (1987).
ISR and Written Opinion in PCT/EP2010/065188, Jan. 12, 2011.
ISR and Written Opinion in PCT/US01/18400 (Jan. 28, 2005).
ISR and Written Opinion in PCT/US11/24615.
ISR and Written Opinion in PCT/US2004/010903 (Dec. 20, 2004).
ISR and Written Opinion in PCT/US2006/021286.
ISR and Written Opinion in PCT/US2007/002063 (Nov. 15, 2007).
ISR and Written Opinion in PCT/US2009/050931 (Nov. 26, 2009).
Extended European Search Report for EP 10181911.8 mailed Jun. 1, 2011.
Extended European Search Report for EP 10184514.7 mailed Dec. 20, 2010.
International Preliminary Report on Patentability mailed Sep. 20, 2007, for PCT/US2006/007772.
Japanese Office Action for JP 2006-509830 mailed Jun. 1, 2011.
Office Action for U.S. Appl. No. 11/246,911 mailed Feb. 8, 2011.
Advisory Action for U.S. Appl. No. 11/360,845, mailed Jun. 14, 2010.
Office Action for U.S. Appl. No. 11/360,845 mailed Aug. 4, 2010.
Office Action for U.S. Appl. No. 11/360,845 mailed Apr. 26, 2011.
Advisory Action for U.S. Appl. No. 11/698,298 mailed May 20, 2011.
Office Action for U.S. Appl. No. 11/698,298, mailed Jun. 29, 2011.
Chiang, C.M. et al., Expression and purification of general transcription factors by FLAG epitope-tagging and peptide elution, Pept Res, 6: 62-64 (1993).
Courrier et al., Reverse water-in-fluorocarbon emulsions and microemulsions obtained with a fluorinated surfactant, Colloids and Surfaces A: Physicochem. Eng. Aspects 244:141-148 (2004).
Garstecki, etal., Formation of monodisperse bubbles in a microfiuidic fiow-focusing device, Appl Phys Lett 85(13):2649-2651 (2004).
Lee et al., Circulating fiows inside a drop under time-periodic non-uniform electric fields, Phys Fuilds 12(8):1899-1910 (2000).
Mackenzie, IABS Symposium on Reduction of Animal Usage in the Development and Control of Biological Products, London, UK, 1985.
Mueth et al., Origin of stratification in creaming emulsions, Physical Review Letters 77(3):578-581 (1996).
Mulder et al., Characterization of tWO human monoclonal antibodies reactive with HLA-B12 and HLA-B60, respectively, raised by in vitro secondary immunization of peripheral blood lymphocytes, Hum. Immunol 36(3):186-192 (1993).
Nakano et al., High speed polymerase chain reaction in constant flow, Biosci Biotech and Biochem, 58:349-52 (1994).

(56) References Cited

OTHER PUBLICATIONS

Stone et al., Engineering flows in small devices: Microfluidics toward a lab-on-a-chip, Ann. Rev. Fluid Mech. 36:381-441 (2004).

Sung et al. Chip-based microfluidic devices coupled with electrospray ionization-mass spectrometry, Electrophoresis 26:1783-1791 (2005).

Tabatabai and Faghri, A New Two-Phase Flow Map and Transition Boundary Accounting for Surface Tension Effects in Horizontal Miniature and Micro Tubes, J Heat Transfer 123:958-968 (2001).

Tabatabai et al, Economic feasability study of polyelectrolyte-enhanced ultrafiltration (PEUF) for water softening, J Membrane Science 100(3):193-207 (1995).

Tabatabai et al., Reducing Surfactant Adsorption on Carbonate Reservoirs, SPE Resenroir Engineering 8(2):117-122 (1993).

Tabatabai, Water Softening Using polyelectrolyte-enhanced ultrafiltration, Separation Science Technology 30(2):211-224 (1995).

Taly et al., Droplets as Microreactors for High-Throughput Biology, Chembiochem 8(3):263-272 (2007).

Taylor, The formation of emulsions in definable field of flow, Proc R Soc London A 146(858):501-523 (1934).

Theberge et al., Microdroplets in Microfluidics: An Evolving Platform for Discoveries in Chemistry and Biology, Angew. Chem. Int. Ed 49(34):5846-5868 (2010).

Walde, P. et al., Oparin{s reactions revisited: enzymatic synthesis of poly(adenylic acid) in micelles and self-reproducing vesicles. J Am Chem Soc, 116: 7541-7547 (1994).

Wasserman et al., Structure and reactivity of allyl-siloxane monolayers formed by reaction of allcyltrichlorosilanes on silicon substrates, Langmuir 5:1074-1087 (1989).

Werle et al., Convenient single-step, one tube purification of PCR products for direct sequencing, Nucl Acids Res 22(20):4354-4355 (1994).

Yelamos, J. et al., Targeting of non-Ig sequences in place of the V segment by somatic hypermutation. Nature 376(6537):225-9 (1995).

Sakamoto, 2005, Rapid and simple quantification of bacterial cells by using a microfluidic device, Appl Env Microb.

\* cited by examiner

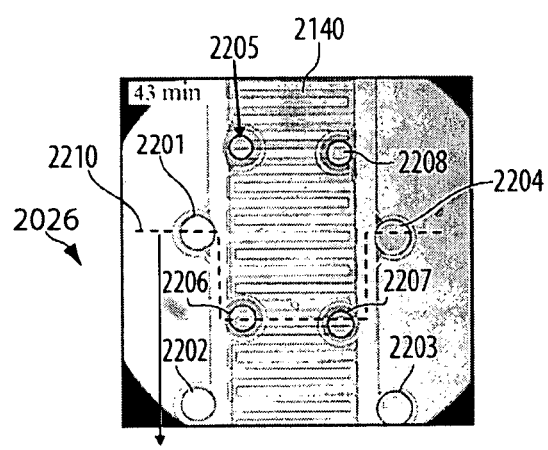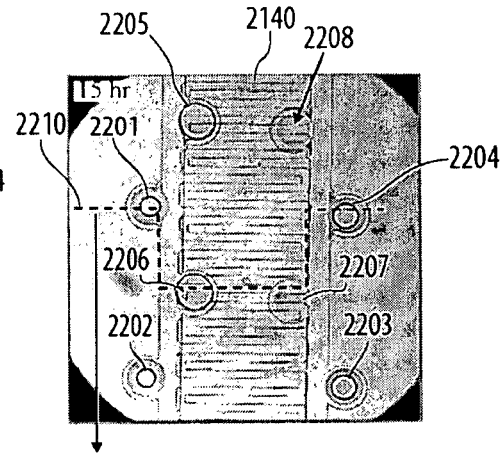
Fig. 13A    Fig. 13C
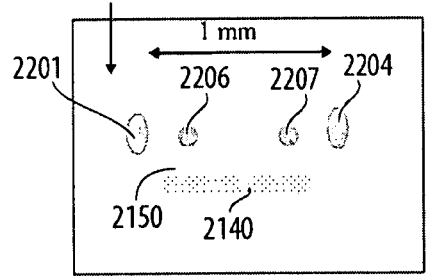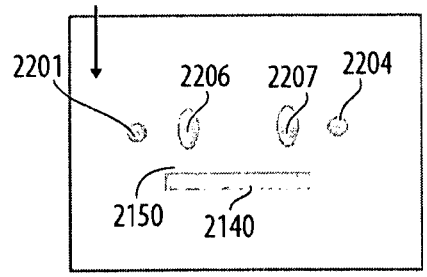
Fig. 13B    Fig. 13D

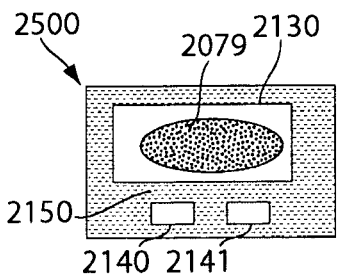
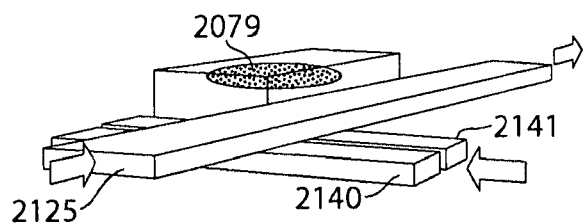
Fig. 18A    Fig. 18B
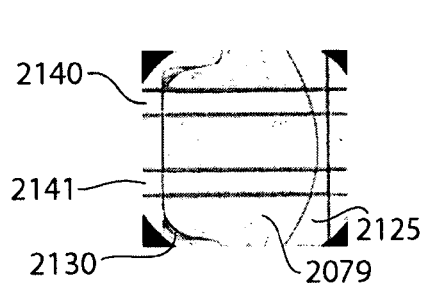
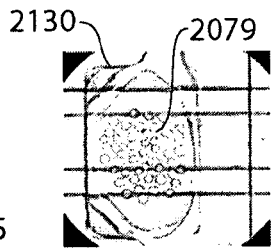
Fig. 18C    Fig. 18D
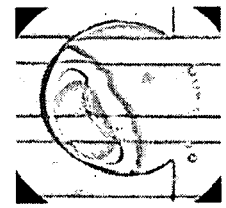
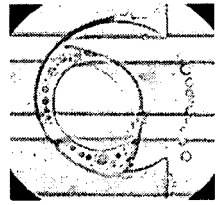
Fig. 18E    Fig. 18F
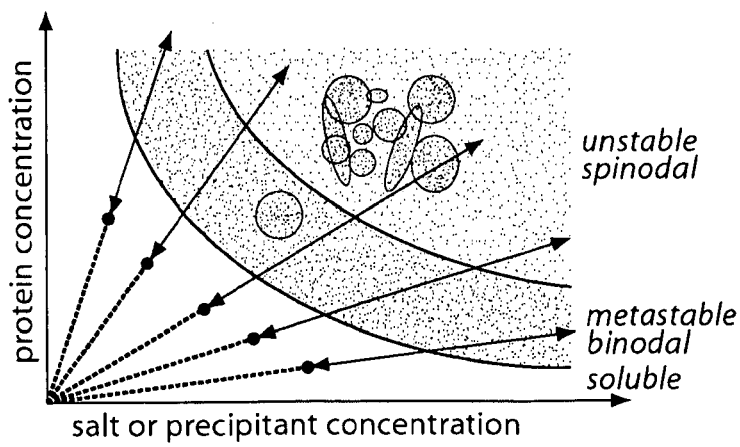
Fig. 18G

US 8,772,046 B2

MANIPULATION OF FLUIDS AND REACTIONS IN MICROFLUIDIC SYSTEMS

RELATED APPLICATIONS

This application is a U.S. National Stage Filing under 35 U.S.C. §371 of PCT/US2008/001544, filed Feb. 6, 2008, which claims priority to U.S. Provisional Patent Application No. 60/899,849, filed Feb. 6, 2007.

FIELD OF INVENTION

The present invention relates generally to microfluidic structures, and more specifically, to microfluidic structures and methods including microreactors for manipulating fluids and reactions.

BACKGROUND

Microfluidic systems typically involve control of fluid flow through one or more microchannels. One class of systems includes microfluidic "chips" that include very small fluid channels and small reaction/analysis chambers. These systems can be used for analyzing very small amounts of samples and reagents and can control liquid and gas samples on a small scale. Microfluidic chips have found use in both research and production, and are currently used for applications such as genetic analysis, chemical diagnostics, drug screening, and environmental monitoring. Although these systems may allow manipulation of small volumes of fluids, additional methods that allow further control and flexibility are needed.

SUMMARY OF THE INVENTION

Microfluidic structures including microreactors for manipulating fluids and reactions and methods associated therewith are provided.

In one aspect of the invention, a method is provided. The method comprises providing a microfluidic network comprising a first region and a microfluidic channel in fluid communication with the first region, flowing a first fluid in the microfluidic channel, flowing a first droplet comprising a second fluid in the microfluidic channel, wherein the first fluid and the second fluid are immiscible, positioning the first droplet at the first region, and maintaining the first droplet at the first region while the first fluid is flowing in the microfluidic channel, wherein positioning and/or maintaining the first droplet at the first region does not require the use of a surfactant in the first or second fluids.

In some instances in connection with the methods described herein, the first and/or second fluids does not comprise a surfactant. The method may further comprise flowing a second droplet comprising a third fluid in the microfluidic channel, wherein the third fluid and the first fluid are immiscible, and positioning the second droplet at a second region in fluid communication with the microfluidic channel. In some instances, the third fluid does not comprise a surfactant. In other instances, the first and second droplets do not come into physical contact with each other during the positioning and/or maintaining steps.

In some embodiments in connection with the methods described herein, positioning and/or maintaining the first droplet at the first region is independent of flow rate of the first fluid in the microfluidic channel.

In some embodiments in connection with the methods described herein, the first region is closer in distance to a first inlet of the microfluidic network for introducing the first fluid into the microfluidic channel than the second region.

In some embodiments in connection with the methods described herein, the first droplet is positioned at the first region before the second droplet is positioned in the second region.

In some embodiments in connection with the methods described herein, the method further comprises removing the first droplet from the first region and then removing the second droplet from the second region.

In some embodiments in connection with the methods described herein, the method comprises flowing a fluid comprising a surfactant in the microfluidic channel.

In some embodiments in connection with the methods described herein, the method comprises coating the first and/or second droplets with a surfactant.

In some embodiments in connection with the methods described herein, the method comprises dewetting the first and/or second droplets from a surface of the microfluidic channel.

In some embodiments in connection with the methods described herein, the first and second droplets are removed from the first and second regions, respectively, by reversing a direction of flow in the microfluidic channel.

In some embodiments in connection with the methods described herein, positioning of the first droplet at the first region affects a direction of flow of a second droplet in the microfluidic network compared to when the first droplet is not positioned at the first region.

In some embodiments in connection with the methods described herein, the first droplet is positioned at the first region while the first fluid is flowing in the microfluidic channel.

In some embodiments in connection with the methods described herein, the microfluidic channel comprises an upstream portion, a downstream portion, and first and second fluid paths, at least one fluid path branching from the upstream portion and reconnecting at the downstream portion.

In some embodiments in connection with the methods described herein, the first and second fluid paths have different resistances to flow.

In some embodiments in connection with the methods described herein, the first region is positioned within the first fluid path. In some cases, the first fluid path has less resistance to flow compared to the second fluid path prior to positioning of a first droplet at the first region, and the first fluid path has greater resistance to flow after positioning of the first droplet at the first region.

In some embodiments in connection with the methods described herein, the method comprises positioning several droplets at regions of the microfluidic network, wherein the droplets are positioned in the regions in the order the droplets are introduced into the microfluidic network.

In some embodiments in connection with the methods described herein, the method comprises removing several droplets positioned at regions of the microfluidic network, wherein the droplets are removed in the order the droplets were introduced into the microfluidic network.

In some embodiments in connection with the methods described herein, the method comprises removing several droplets positioned at regions of the microfluidic network, wherein the droplets are removed in the reverse order the droplets were introduced into the microfluidic network.

In another aspect of the invention, a method is provided. The method comprises providing a microfluidic network comprising at least a first inlet to a microfluidic channel, a first and a second region for positioning a first and a second droplet, respectively, the first and second regions in fluid communication with the microfluidic channel, wherein the first region is closer in distance to the first inlet than the second region, flowing a first fluid in the microfluidic channel, flowing a first droplet, defined by a fluid immiscible with the first fluid, in the microfluidic channel, positioning the first droplet at the first region, flowing a second droplet, defined by a fluid immiscible with the first fluid, in the microfluidic channel past the first region without the second droplet physically contacting the first droplet, and positioning the second droplet at the second region.

In one aspect of the invention, a method is provided. The method comprises positioning a first droplet defined by a first fluid, and a first component within the first droplet, in a first region of a microfluidic network, forming a first precipitate of the first component in the first droplet while the first droplet is positioned in the first region, dissolving a portion of the first precipitate of the first compound within the first droplet while the first droplet is positioned in the first region, and re-growing the first precipitate of the first component in the first droplet.

In another aspect of the invention, a method is provided. The method comprises positioning a droplet defined by a first fluid, and a first component within the droplet, in a first region of a microfluidic network, the droplet being surrounded by a second fluid immiscible with the first fluid, positioning a third fluid in a reservoir positioned adjacent to the first region, the reservoir being separated from the region by a semi-permeable barrier, changing a concentration of the first component within the first fluid of the droplet, and allowing a concentration-dependent chemical process involving the first component to occur within the droplet.

In another aspect of the invention, a method is provided. The method comprises positioning a droplet defined by a first fluid, and a first component within the droplet, in a first region of a microfluidic network, the droplet being surrounded by a second fluid immiscible with the first fluid, flowing a third fluid in a microfluidic channel in fluid communication with the first region and causing a portion of the second fluid to be removed from the first region, changing the volume of the droplet and thereby changing a concentration of the first component within the droplet, and allowing a concentration-dependent chemical process involving the first component to occur within the droplet.

In another aspect of the invention, a device is provided. The device comprises a fluidic network comprising a first region and a first microfluidic channel allowing fluidic access to the first region, the first region constructed and arranged to allow a concentration-dependent chemical process to occur within said first region, wherein the first region and the first microfluidic channel are defined by voids within a first material, a reservoir adjacent to the first region and a second microfluidic channel allowing fluidic access to the reservoir, the reservoir defined at least in part by a second material that can be the same or different than the first material, a semi-permeable barrier positioned between the reservoir and the first region, wherein the barrier allows passage of a first set of low molecular weight species, but inhibits passage of a second set of large molecular weight species between the first region and the reservoir, the barrier not constructed and arranged to be operatively opened and closed to permit and inhibit, respectively, fluid flow in the first region or the reservoir, wherein the device is constructed and arranged to allow fluid to flow adjacent to a first side of the barrier without the need for fluid to flow through the barrier, and wherein the barrier comprises the first material, the second material, or a combination of the first and second materials.

In another aspect of the invention, a method is provided. The method comprises providing a fluidic network comprising a first region, a microfluidic channel allowing fluidic access to the first region, a reservoir adjacent to the first region, and a semi-permeable barrier positioned between the first region and the reservoir, wherein the first region is constructed and arranged to allow a concentration-dependent chemical process to occur within the first region, and wherein the barrier allows passage of a first set of low molecular weight species, but inhibits passage of a second set of large molecular weight species between the first region and the reservoir, providing a droplet defined by a first fluid in the first region, providing a second fluid in the reservoir, causing a component to pass across the barrier, thereby causing a change in a concentration of the first component in the first region, and allowing a concentration-dependent chemical process involving the first component to occur within the first region.

In another aspect of the invention, a method is provided. The method comprises providing a fluidic network comprising a first region and a first microfluidic channel allowing fluidic access to the first region, the first region constructed and arranged to allow a concentration-dependent chemical process to occur within said first region, wherein the first region and the microfluidic channel are defined by voids within a first material, positioning a first fluid containing a first component in the first region, positioning a second fluid in a reservoir via a second microfluidic channel allowing fluidic access to the reservoir, the reservoir and the second microfluidic channel being defined by voids in a second material, and the reservoir being separated from the first region by a semi-permeable barrier, wherein the barrier comprises the first and/or second materials, changing a concentration of the first component in the first region, and allowing a concentration-dependent chemical process involving the first component to occur within the first region.

In another aspect of the invention, a method is provided. The method comprises positioning a first droplet defined by a first fluid, and a first component within the droplet, in a first region of a microfluidic network, positioning a second droplet defined by a second fluid, and a second component within the droplet, in a second region of the microfluidic network, wherein the first and second droplets are in fluid communication with each other, forming a first precipitate of the first component in the first droplet while the first droplet is positioned in the first region, forming a second precipitate of the second component in the second droplet while the second droplet is positioned in the second region, simultaneously dissolving a portion of the first precipitate and a portion of the second precipitate within the first and second droplets, respectively, and re-growing the first precipitate in the first droplet and re-growing the second precipitate in the second droplet, while the first and second droplets are positioned in the first and second regions, respectively.

In another aspect of the invention, a method is provided. The method comprises providing a microfluidic network comprising a first region and a microfluidic channel in fluid communication with the first region, the first region having at least one dimension larger than a dimension of the microfluidic channel, flowing a first fluid in the microfluidic channel, flowing a first droplet comprising a second fluid in the microfluidic channel, wherein the first fluid and the second fluid are immiscible, and while the first fluid is flowing in the microfluidic channel, positioning the first droplet in the first region, the first droplet having a lower surface free energy when positioned in the first region than when positioned in the microfluidic channel.

In another aspect of the invention, a method is provided. The method comprises providing a microfluidic network comprising a first region and a microfluidic channel in fluid communication with the first region, flowing a first fluid in the microfluidic channel, flowing a first droplet comprising a second fluid in the microfluidic channel, wherein the first fluid and the second fluid are immiscible, while the first fluid is flowing in the microfluidic channel, positioning the first droplet in the first region, and maintaining the first droplet in the first region while the first fluid is flowing in the microfluidic channel.

In another aspect of the invention, a method is provided. The method comprises providing a microfluidic network comprising at least a first inlet to a microfluidic channel, a first and a second region for positioning a first and a second droplet, respectively, the first and second regions in fluid communication with the microfluidic channel, wherein the first region is closer in distance to the first inlet than the second region, flowing a first fluid in the microfluidic channel, flowing a first droplet, defined by a fluid immiscible with the first fluid, in the microfluidic channel, while the first fluid is flowing in the microfluidic channel, positioning the first droplet in the first region, flowing a second droplet, defined by a fluid immiscible with the first fluid, in the microfluidic channel, while the first fluid is flowing in the microfluidic channel, positioning the second droplet in the second region, and maintaining the first droplet in the first region and the second droplet in the second region, respectively, while the first fluid is flowing in the microfluidic channel.

In another aspect of the invention, a method is provided. The method comprises providing a microfluidic network comprising at least a first inlet to a microfluidic channel, and a first and a second region for positioning a first and a second droplet, respectively, the first and second regions in fluid communication with the microfluidic channel, flowing a first fluid at a first flow rate in the microfluidic channel, flowing a first droplet, defined by a fluid immiscible with the first fluid, in the microfluidic channel, flowing a second droplet, defined by a fluid immiscible with the first fluid, in the microfluidic channel, flowing the first fluid at a second flow rate in the microfluidic channel, wherein the second flow rate is slower than the first flow rate, and while the first fluid is flowing at the second flow rate, positioning the first droplet in the first region and positioning the second droplet in the second region.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures:

FIGS. 13A-13D show examples of changing the sizes of droplets in a microreactor region of a device, according to another embodiment of the invention.

FIGS. 18A-18G show the use of another microfluidic device for manipulating fluids and reactions, according to another embodiment of the invention.

DETAILED DESCRIPTION

The present invention relates to microfluidic structures and methods for manipulating fluids and reactions. Such structures and methods may involve positioning fluid samples, e.g., in the form of droplets, in a carrier fluid (e.g., an oil, which may be immiscible with the fluid sample) in predetermined regions in a microfluidic network. In some embodiments, positioning of the droplets can take place in the order in which they are introduced into the microfluidic network (e.g., sequentially) without significant physical contact between the droplets. Because of the little or no contact between the droplets, coalescence between the droplets can be avoided. Accordingly, in such embodiments, surfactants are not required in either the fluid sample or the carrier fluid to prevent coalescence of the droplets. Positioning of droplets without the use of surfactants is desirable in certain cases where surfactants may negatively interfere with the contents in the fluid sample (e.g., proteins). Structures and methods described herein also enable droplets to be removed sequentially from the predetermined regions to a different region of the fluidic network where they can be further processed.

Once the droplets are positioned at the predetermined regions, they can be stored and/or may undergo manipulation (e.g., diffusion, evaporation, dilution, and precipitation). In some instances, many (e.g., 1000) droplets can be manipulated, sometimes simultaneously. Manipulation of fluid samples can be useful for a variety of applications, including testing for reaction conditions, e.g., in crystallization, and chemical and/or biological assays.

Microfluidic chips described herein may include a microfluidic network having a region for forming droplets of sample in a carrier fluid (e.g., an oil), and one or more microreactor regions (e.g., microwells, reservoirs, or portions of a microfluidic channel) in which the droplets can be positioned and reaction conditions within the droplet can be varied. Droplets may be positioned sequentially in regions of the microfluidic network so that upon manipulating and/or performing a chemical and/or biological process within each the droplets, the droplets can be identified at a later time, for example, to determine the particular conditions within the droplets that lead to a favorable outcome (e.g., optimal conditions for forming a product, for crystal growth, etc.).

Figure 1A:
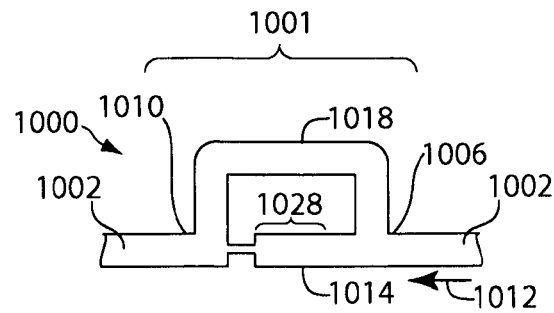
FIGS. 1A-1E show schematically a microfluidic network for positioning a droplet in a region of the network according to one embodiment of the invention.
Figure 11A:
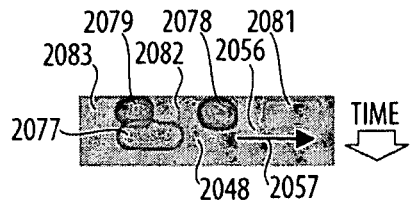
FIGS. 11A-11F show the positioning of droplets within microwells of a microfluidic device, according to another embodiment of the invention.
Figures 1, 11A:
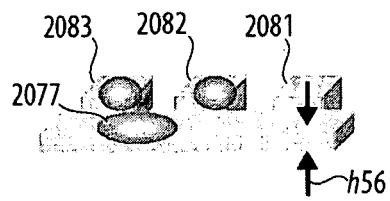
Figure 11B:
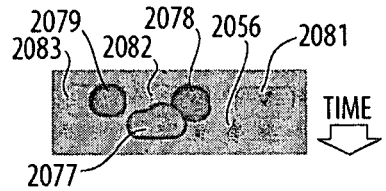
Figures 1, 11B:
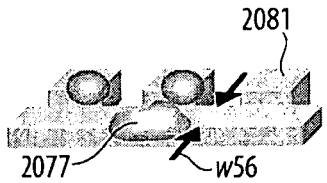
Figure 11C:
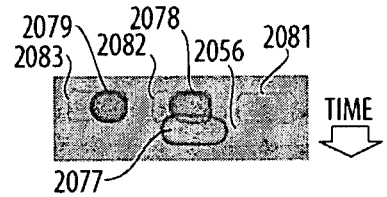
Figure 11D:
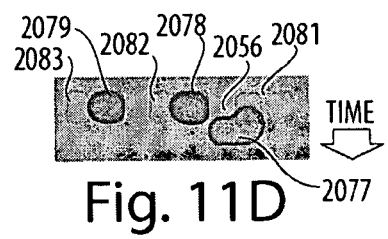
Figure 11E:
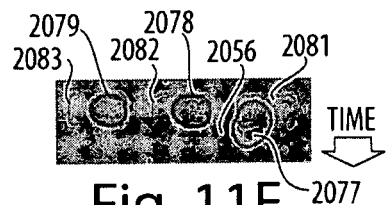
Figures 1, 11E:
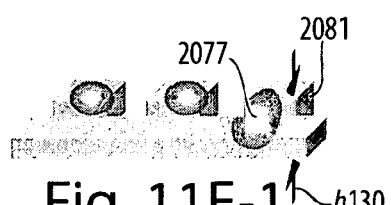

FIG. 1 shows a method for positioning a droplet in a region of a microfluidic network according to one embodiment of the invention. As shown in illustrative embodiment of FIG. 1A, microfluidic network 1000 comprises section 1001 including microfluidic channel 1002 having an upstream portion 1006, a downstream portion 1010 (as fluid flows in the direction of arrow 1012), and fluid paths 1014 and 1018. Fluid paths 1014 and 1018 are connected, with fluid path 1018 branching off from the upstream portion and reconnecting at the downstream portion. Fluid paths 1014 and 1018 may serve as alternative paths for fluid flow. In some cases, resistance to fluid flow may differ between fluid paths 1014 and 1018. For example, fluid path 1014 may have less resistance to fluid flowing in the direction of arrow 1012 prior to positioning of a droplet in this section of the microfluidic network. As shown in this illustrative embodiment, fluid path 1014 has a lower resistance to fluid flow than fluid path 1018 due to the relatively longer channel length of fluid path 1018. It should be understood, however, that the microfluidic network may have other designs and/or configurations for imparting different relative resistances to fluid flow, and such designs and configurations can be determined by those of ordinary skill in the art. For instance, in some embodiments, the length, width, height, and/or shape of the fluid path can be designed to cause one fluid path to have a resistance to fluid flow different from another fluid path. In other embodiments, at least a portion of a fluid path may include an obstruction such as a valve (which may change resistance dynamically), a semi-permeable plug (e.g., a hydrogel), a membrane, or another structure that can impart and/or change resistance to fluid flow through that portion.

Figure 1B:
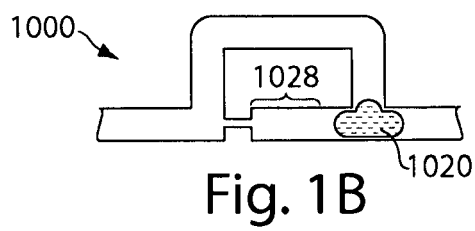
Figure 1C:
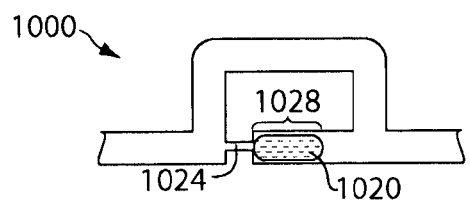

As shown in FIGS. 1B and 1C, droplet 1020 flows in the direction of 1012, e.g., by being carried by a carrier fluid flowing in the same direction. Upon passing the junction between flow paths 1014 and 1018 at upstream portion 1006, the droplet flows in fluid path 1014 due to its lower resistance to flow in that fluid path relative to fluid path 1018. However, as fluid path 1014 includes a fluid constriction, e.g., in the form of a narrow fluid path portion 1024, droplet 1020 cannot flow further down the microfluidic network. Accordingly, droplet 1020 is positioned within a region 1028 (e.g., a "microwell") of the microfluidic network. In some embodiments, droplet 1020 can be maintained at the region even though carrier fluid continues to flow in the microfluidic network (e.g., in the direction of arrow 1012).

Although FIG. 1 shows region 1028 having a cross-sectional area approximately the same as the cross-sectional area of microfluidic channel 1002, it should be understood that region 1028 can have any suitable cross-sectional area, dimensions, shape, etc. which may be suitable for containing, holding, and/or positioning a droplet.

Figure 1D:
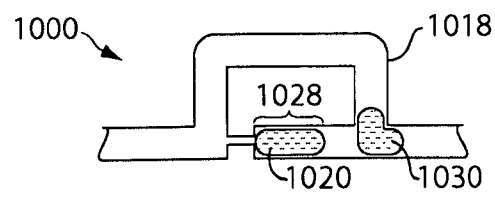
Figure 1E:
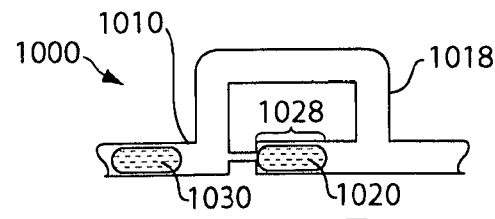

As shown in the embodiment illustrated in FIG. 1D, the positioning of droplet 1020 at region 1028 causes fluid path 1014 to be plugged such that no or minimal fluid flows past narrow fluid path portion 1024. This plugging of fluid path 1014 causes a higher resistance to fluid flow in that path compared to that of fluid path 1018. As a result, when a second droplet 1030 flows in the direction of arrow 1012, the second droplet bypasses flow path 1014 and enters flow path 1018, which now has a lower resistance than that of fluid path 1014 (FIG. 1D). Accordingly, second droplet 1030 can bypass first droplet 1020 and can now be positioned in a second region within microfluidic network 1000.

It should be understood that when droplet 1020 is positioned at region 1028, the droplet may plug all or a portion of fluid path 1014 and/or narrow fluid path portion 1024. For instance, in some cases, the droplet plugs all of such fluid paths such that none of the fluid flowing in microfluidic channel 1002 passes through narrow fluid path portion 1024. In other embodiments, the droplet may plug only a portion of such fluid paths such that some fluid passes through narrow fluid path portion 1024 even though the droplet is positioned at region 1028. The amount of fluid flowing past the droplet may depend on factors such as the dimensions of fluid path portions 1014 and/or 1024, the size of the droplets, the flow rate, etc. As long as the droplet causes fluid path 1014 to have a higher relative resistance to fluid flow than fluid path 1018, a second droplet can bypass fluid path 1014 and enter fluid path 1018.

As described above, fluid paths 1014 and 1018 may have different resistances fluid flow depending on whether or not a droplet is positioned at region 1028. In the absence of a droplet positioned at region 1028, fluid path 1014 may be configured to have a lower resistance to fluid flow than fluid path 1018. For example, greater than 50%, greater than 60%, greater than 70%, greater than 80%, or greater than 90% of the fluid flowing in channel 1002 at upstream portion 1006 may flow in fluid path 1014 compared to fluid path 1018. However, when the droplet is positioned and maintained in region 1028, fluid path 1014 may be relatively more restrictive to fluid flow. For example, less than 50%, less than 40%, less than 30%, less than 20%, or less than 10% of the fluid flowing in channel 1002 at upstream portion 1006 may flow in fluid path 1014 compared to that of 1018. In some cases, 100% of the fluid flowing in direction 1012 in microfluidic channel 1002 flows in fluid path 1018 upon positioning of a droplet in region 1028.

As illustrated in the exemplary embodiment of FIG. 1, the positioning of droplet 1020 (e.g., a first droplet) and the subsequent bypass of droplet 1030 (e.g., a second droplet) does not require contact between the first and second droplets. In certain embodiments, the second droplet does not physically contact the first droplet after positioning of the first droplet in region 1028. In other embodiments, the second droplet can come into physical contact with the first droplet as it bypasses the first droplet, however, due to such minimal contact between the two droplets, the droplets do not coalesce. Accordingly, the positioning of the droplets in the microfluidic network can take place without the use of surfactants. In other words, surfactants in either a fluid flowing in channel 1002 (e.g., a carrier fluid) or within the droplets is not required in order to stabilize the droplets and/or prevent the droplets from coalescing with one another during positioning or carrying the droplet in the microfluidic channel, and/or during maintaining the droplets within a predetermined region within the microfluidic network. However, in instances where coalescence is desired (e.g., to allow a reaction between reagents contained in two droplets), the microfluidic network and methods for operating the network can be configured to allow such physical contact and/or coalescence between droplets.

In some embodiments, methods for positioning a droplet in a microfluidic network include the steps of providing a microfluidic network comprising a first region (e.g., region 1028 of FIG. 1A) and a microfluidic channel in fluid communication with the first region, flowing a first fluid (e.g., a carrier fluid) in the microfluidic channel, and flowing a first droplet comprising a second fluid (e.g., a fluid sample) in the microfluidic channel, wherein the first fluid and the second fluid are immiscible. The first droplet may be positioned in the first region and maintained in the first region while the first fluid is flowing in the microfluidic channel. In such embodiments, positioning and/or maintaining the first droplet in the first region does not require the use of a surfactant in the first or second fluids.

In some embodiments, a chemical and/or biological process can be carried out in droplet 1020 of FIG. 1 while the droplet is positioned in region 1028. Additionally or alternatively, the droplet may be manipulated. For example, a fluid sample in the droplet may undergo a process such as diffusion, evaporation, dilution, and/or precipitation. Such methods of manipulation are described in more detail below. The droplet may be manipulation by, for example, changing the concentration of the fluid flowing in channel 1002 after the droplet has been positioned at region 1028. In other embodiments, region 1028 is in fluid communication with another fluidic channel, flow path, reservoir, or other structure, e.g., via a semi permeable membrane that may be positioned adjacent the region (e.g., underneath or above region 1028), and manipulation of the droplet can occur via such passages.

Figure 2A:
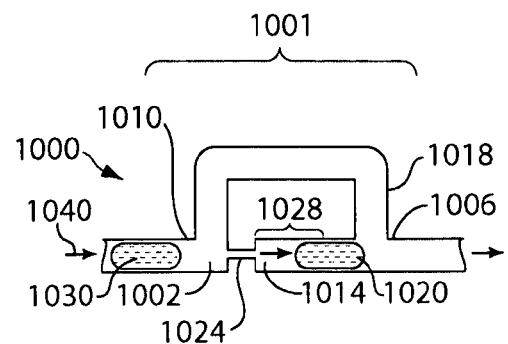
FIGS. 2A-2C show schematically removal of a droplet from a region of the network according to another embodiment of the invention.
Figure 2B:
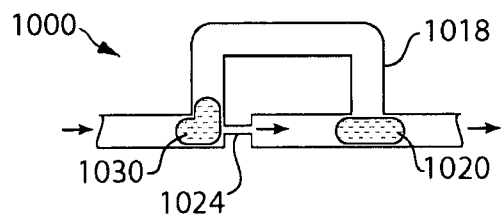
Figure 2C:
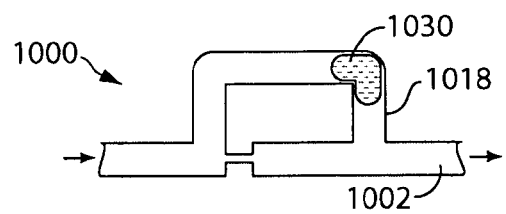

In some embodiments of the invention, droplets that have been positioned at regions of a microfluidic network can be removed or extracted from the regions to a different location in the fluidic network, where they can be optionally processed, manipulated, and/or collected. As shown in the illustrative embodiments of FIGS. 2A-2C, removing droplet 1020 from region 1028 of section 1001 of microfluidic network 1000 can take place by reversing the flow of the carrier fluid in the network such that the carrier fluid now flows in the direction of arrow 1040 (instead of in the direction of arrow 1012 of FIGS. 1A-1E).

In such embodiments, upstream portion 1006 and downstream portion 1010 of FIGS. 1A-1E now become reversed such that portion 1010 is now an upstream portion and portion 1006 is now a downstream portion. The flow of a carrier fluid in the direction of arrow 1040 in microfluidic channel 1002 causes a portion of the fluid to flow through narrow fluid path portion 1024 into region 1028 where droplet 1020 is positioned. This fluid flow causes the droplet to flow in the direction of arrow 1040. As shown in the embodiment illustrated in FIG. 2B, droplet 1030, which may have been positioned at a different region of the microfluidic network, can be removed from that region and may also flow in the direction of arrow 1040. As droplet 1030 encounters narrow fluid path portion 1024, the droplet cannot flow through this narrow opening due to its high resistance to flow. As a result, the droplet bypasses the narrow fluid path portion and flows into fluid path 1018 until it reaches microfluidic channel 1002 at downstream portion 1006. Thus, by reversing the flow and the pressure gradient in the microfluidic network, droplets 1020 and 1030 can be removed sequentially from the regions of the microfluidic network where they previously resided. That is, droplet 1020, which was positioned first before droplet 1030, can be removed from its region and can enter a different region of the microfluidic network before that of droplet 1020.

In some embodiments, sequential positioning of droplets can be performed such that a first droplet is positioned in a first region before a second droplet is positioned in a second region (and, optionally, before third, fourth, fifth droplets, etc. are positioned in their respective regions). As described above, sequential removal of the droplets can be performed such that the first droplet is removed from a region and/or positioned at a different location on the microfluidic network before the second droplet (and, optionally, before third, fourth, fifth droplets, etc. are removed from their respective regions). In other embodiments, removal of the droplets can be performed such that the second droplet is removed and/or positioned at a different location on the microfluidic network before the first droplet.

In some cases, several (e.g., greater than 2, greater than 5, greater than 10, greater than 50, greater than 100, greater than 200, greater than 500, or greater than 1000) droplets can be positioned at regions of the microfluidic network, wherein the droplets are positioned in the regions in the order the droplets are introduced into the microfluidic network. In some cases, removing several droplets positioned at regions of the microfluidic network comprises removing the droplets in the order the droplets were introduced into the microfluidic network (or in the order the droplets were positioned into the regions of the microfluidic network). In other cases, removing several droplets positioned at regions of the microfluidic network comprises removing the droplets in the reverse order the droplets were introduced into the microfluidic network (or in the reverse order the droplets were positioned into the regions of the microfluidic network). Other methods of positioning and removal of droplets are also possible.

The sequential (or predetermined/known order of) removal of droplets from regions of a microfluidic network can allow control over the identification and location of each droplet within the network. This can also allow determination of the contents inside each of the droplets from the time they are formed and/or introduced into the microfluidic network, to the time the droplets are manipulated and/or extracted from the microfluidic network.

Figure 3:
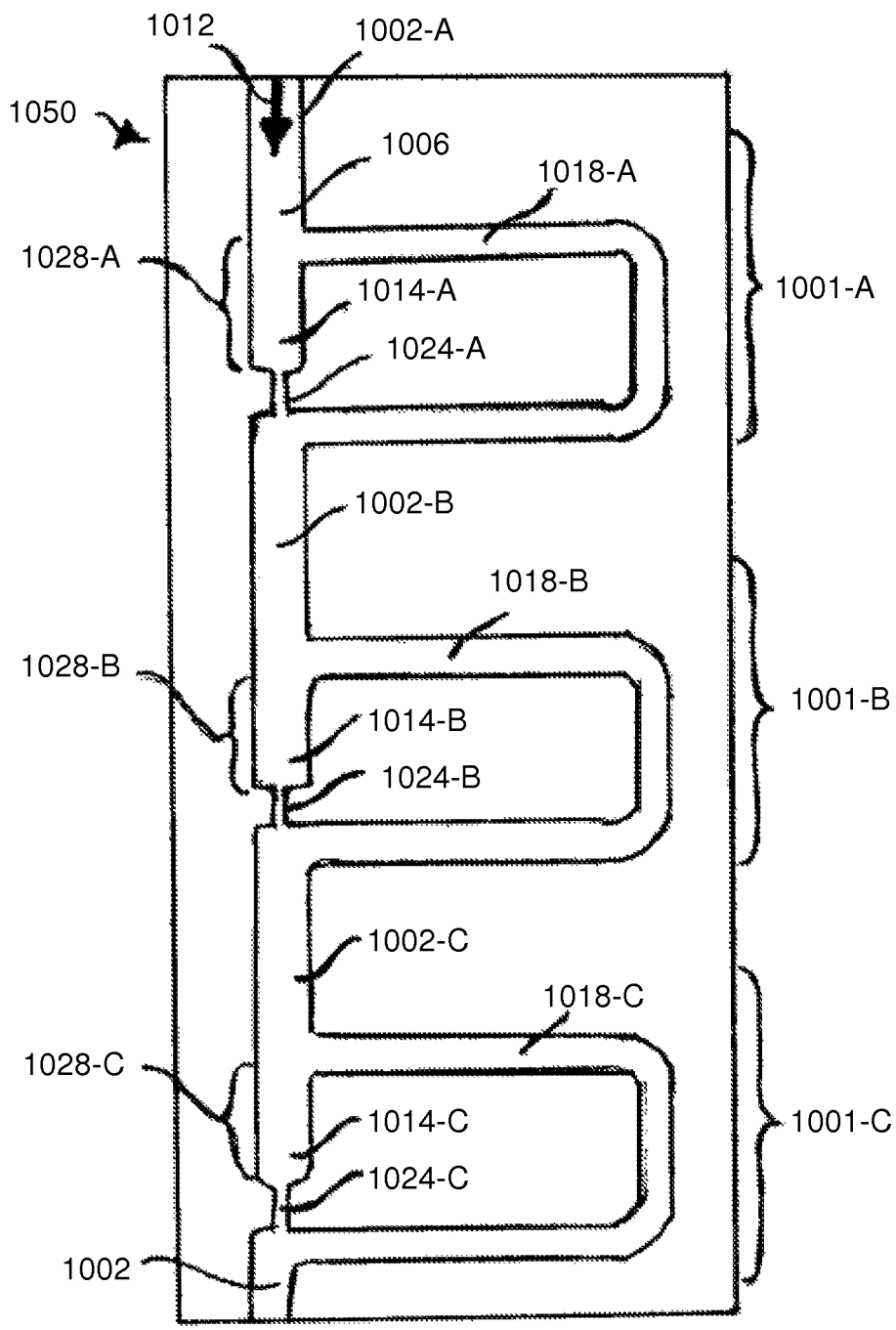
FIG. 3 is a photograph showing multiple sections of a microfluidic network for positioning droplets according to another embodiment of the invention.

FIG. 3 is a photograph of multiple sections 1001-A, 1001-B, and 1001-C of microfluidic network 1050 according to one embodiment of the invention. A carrier fluid may flow in microfluidic channel 1002-A in the direction of arrow 1012 from an inlet positioned upstream from portion 1006. The carrier fluid may partition at the junction where fluid paths 1014-A and 1018-A branch off from microfluidic channel 1002. The proportion of fluid that flows in each of the fluid paths can be determined at least in part by the relative resistance to fluid flow in the paths, as described above. In the embodiment shown in FIG. 3, sections 1001-A, 1001-B, and 1001-C are positioned in series. In other embodiments, however, such sections may be positioned in parallel and/or in both series and parallel. Other configurations are also possible.

A microfluidic network may have any suitable number of microfluidic sections 1001. For instance, the microfluidic network may have greater than or equal to 5, greater than or equal to 10, greater than or equal to 30, greater than or equal to 70, greater than or equal to 100, greater than or equal to 200, greater than or equal to 500, or greater than or equal to 1000 such sections.

In additional, although certain embodiments herein show that sections 1001 can allow positioning of a single droplet in each of the sections, in other embodiments, the sections can be designed such that greater than one droplet (e.g., greater than or equal to 2, greater than or equal to 5, or greater than or equal to 10 droplets) can be positioned at each section.

Furthermore, although only two fluid flow paths 1014 and 1018 are shown branching off from channel 1002, in other embodiments, more than two (e.g., greater than or equal to 3, greater than or equal to 5, or greater than or equal to 10) fluid paths may branch off from channel 1002. Each branching fluid path may optionally comprise one or more regions (e.g., microwells) for positioning and/or maintaining droplets.

Figure 4:
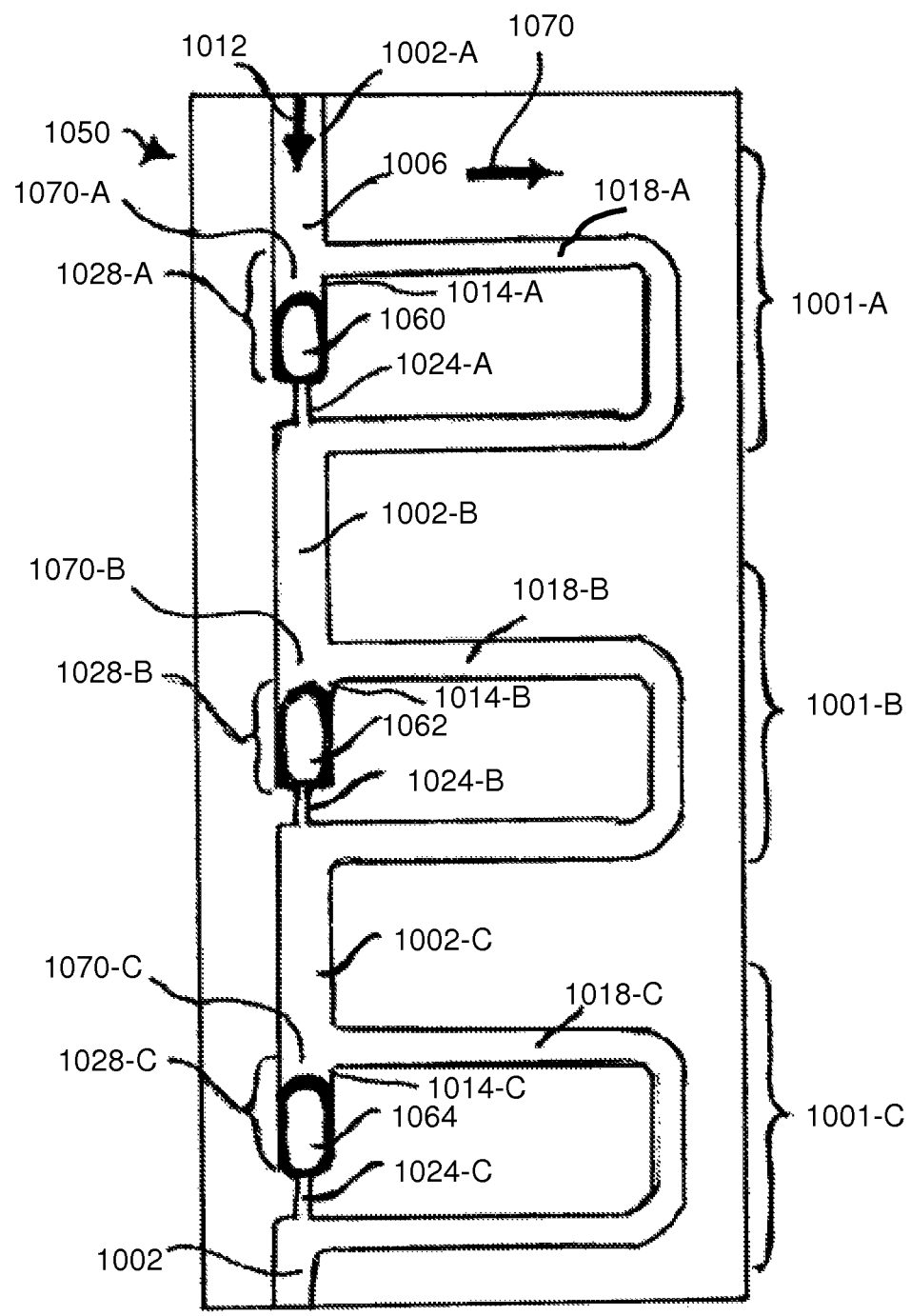
FIG. 4 is a photograph showing multiple droplets positioned in multiple regions of a microfluidic network according to another embodiment of the invention.

FIG. 4 shows the positioning of droplets 1060, 1062, and 1064 at positions 1028-A, 1028-B, and 1028-C, respectively, in microfluidic network 1050 according to one embodiment of the invention. As shown in this illustrative embodiment, carrier fluid flows in the direction of arrow 1012 and carries droplet 1060 through channel 1002-A and into fluidic path 1014-A due to the lower resistance to fluid flow in that fluid path compared to that of fluid path 1018-A. That is, prior to the positioning of droplet 1060 in region 1028-A, more than 50% of the fluid flowing in microfluidic channel 1002-A flows through fluid path 1014-A compared to fluid path 1018-A.

Once droplet 1060 is positioned at region 1028-A, it impedes fluid flow through narrow fluid path portion 1024-A such that the resistance to fluid flow in fluid paths 1014-A and 1018-A are altered. This causes resistance to fluid flow to be higher in portion 1014-A and as a result, a greater amount of fluid flows in the direction of 1070 through fluid path portion 1018-A. Accordingly, a second droplet 1062 flowing through microfluidic channel 1002-A and passing upstream portion 1006 now bypasses fluid path portion 1014-A and flows through portion 1018-A. The second droplet, after bypassing region 1028-A, now enters microfluidic channel portion 1002-B. If there is a lower resistance to fluid flow in fluid path portion 1014-B (e.g., a droplet has not already been positioned in region 1028-B), the droplet can be positioned at this region. Next, a third droplet 1064 can flow through microfluidic channel portion 1002-A in the direction of arrow 1012 and first bypasses region 1028-A due to droplet 1060 already positioned at that region. The droplet can then flow into fluid path portion 1018-A and 1002-B. Since droplet 1062 has already been positioned at region 1028-B, third droplet 1064 bypasses this region and takes the fluid path of least resistance (fluid path portion 1018-B). Upon entering an empty region such as 1028-C, the third droplet can now position itself at that region due to a lower resistance to fluid flow in fluid path 1014-C compared to that of fluid path portion 1018-C (e.g., prior to any other droplet being positioned at region 1028-C).

Accordingly, a method for positioning droplets in regions of a microfluidic network may include providing a microfluidic network comprising at least a first inlet to a microfluidic channel (e.g., positioned upstream of portion 1006 of FIG. 4), a first region (e.g., region 1028-A) and a second region (e.g., region 1028-B) for positioning a first and a second droplet, respectively, the first and second regions in fluid communication with the microfluidic channel, wherein the first region is closer in distance to the first inlet than the second region. The method can include flowing a first fluid (e.g., a carrier fluid) in the microfluidic channel, flowing a first droplet (e.g., a first fluid sample), defined by a fluid immiscible with the first fluid, in the microfluidic channel, and positioning the first droplet in the first region. The method can also include flowing a second droplet (e.g., a second fluid sample), defined by a fluid immiscible with the first fluid, in the microfluidic channel past the first region without the second droplet physically contacting the first droplet. The second droplet may be positioned at the second region. In some instances, the first and/or second droplets are maintained at their respective regions while fluid continues to flow in the microfluidic channel.

It should be understood that other components may be integrated with fluidic networks described herein in some embodiments of the invention. For example, in some instances, resistances to fluid flow can be changed dynamically such that the direction of fluid flow (and, therefore, positioning of droplets) can be controlled by the user. In one such embodiment, valves may be positioned at one or more of positions 1070-A, 1070-B, and 1070-C of FIG. 4. For example, a valve at position 1070-B can cause restriction of fluid flow through fluid path portion 1014-B, e.g., prior to a droplet being positioned at region 1028-B. This can cause a droplet flowing through microfluidic channel portion 1002-B to bypass region 1028-B even though a droplet is not positioned at that region. Thus, the droplet flowing through portion 1002-B will flow through fluid path 1018-B and onto the next available region, where the fluid resistance of that region may or may not be controlled by a similar valve. In some instances, after a droplet bypasses region 1028-B due to a closed valve at position 1070-B (or any other component that can change the relative resistances to fluid flow between fluid paths 1014-B and 1018-B), the valve at position 1070-B can now be reopened to change the relative resistances to fluid flow such that a next droplet can now enter into region 1028-B and be positioned at that region. Such a system can allow droplets to be positioned at any desired region of a microfluidic network.

As described herein, in some embodiments droplets do not require stabilization (e.g., the use of surfactants or other stabilizing agents) in order to be positioned at predetermined regions within microfluidic networks described herein. This is because in some embodiments, the droplets do not significantly physically contact one another during bypass of one droplet to another. Due to the little or no physical contact between the droplets, the droplets do not have a chance to coalesce with one another. Thus, surfactants or other stabilizing agents are not required to stabilize the droplets from coalescence in such embodiments. In some embodiments, the absence of surfactants or other stabilizing agents causes the droplets to wet a surface of the microfluidic network. Even though wetting may occur, the droplets can still be positioned at predetermined regions within the microfluidic network due to, for example, a positive pressure that causes fluid flow to carry these droplets into these regions. As discussed above, the use of droplets and/or a carrier fluid that does not contain a surfactant is advantageous in some embodiments where surfactants may negatively interfere with contents inside the droplets. For example, the droplets may contain proteins, and surfactants are known to denature certain proteins to some extent. However, after manipulation of the droplet and/or carrying out a process such as a chemical and/or biological reaction inside the droplet, surfactants may no longer negatively affect the contents inside the droplet. Accordingly, in such cases, a surfactant or other stabilizing agent can be applied to the droplets. In some embodiments, such application of a stabilizing agent to a droplet after manipulation of the droplet and/or carrying out a process inside the droplet can facilitate mobilization of the droplet out of the region in which the droplet is positioned.

It should be understood, however, than in some embodiments, a droplet and/or a carrier fluid may contain a surfactant or other stabilizing agent that stabilizes a droplet prior to positioning of the droplet at a region in the microfluidic network. In such embodiments, the stabilization may not negatively interfere with contents (e.g., reagents) inside the droplet. Of course, such embodiments will depend on a variety of factors such as the type of stabilizing agent used, the contents inside the droplet, the application, etc.

Figure 5A:
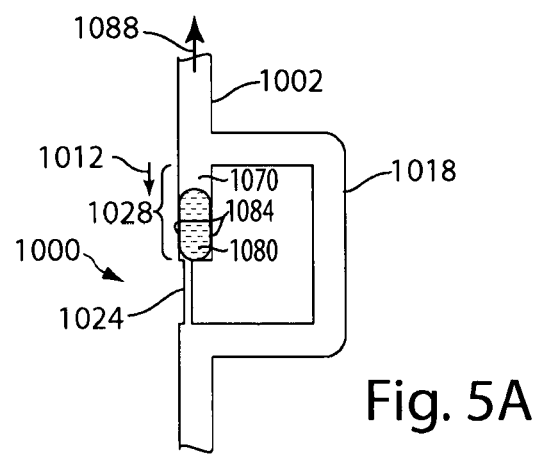
FIGS. 5A-5C show manipulation of a droplet positioned in a region of a microfluidic network by changing the surface tension of the droplet according to another embodiment of the invention.
Figure 5B:
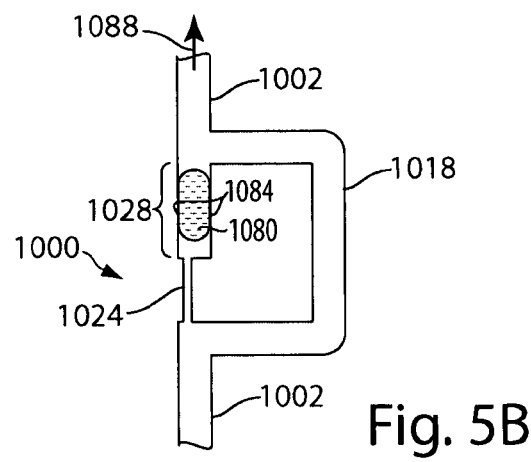
Figure 5C:
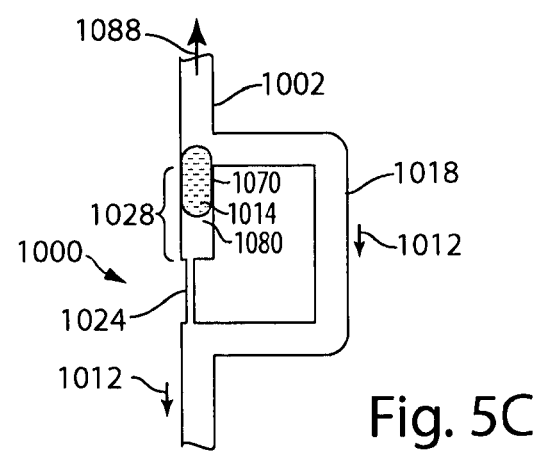

FIGS. 5A-5C show schematically the treatment of a droplet positioned at a predetermined region within a microfluidic network with a stabilizing agent according to one embodiment of the invention. As described above, droplet 1080 can be positioned at region 1028 by flowing a carrier fluid and the droplet in the direction of arrow 1012. After the droplet has been positioned, the droplet may wet a surface of the channel, such as surface portions 1084. In some embodiments, this can cause the droplet to be immobilized at this region, even when a carrier fluid is flowed in the opposite direction (e.g., in the direction of arrow 1088) in attempt to remove the droplet from this region. In such embodiments, a fluid comprising a stabilizing agent (e.g., a surfactant) can be flowed in the direction of arrow 1088 through microfluidic channel 1002. A portion of this fluid can flow through narrow path portion 1024 to reach droplet 1080 at region 1028. This fluid containing the stabilizing agent can cause the droplet to be coated with the stabilizing agent, which can result in the droplet de-wetting from the channel at surface portions 1084. In such cases, the surface tension of the droplet has been reduced. Thus, the droplet may be "depinned" from one or more surfaces of the channel. If desired, after introduction of a fluid containing a stabilizing agent to the droplet, the fluid flow may be stopped for a certain amount of time to allow the stabilizing agent to coat the droplet. In other embodiments, however, flow in channel 1002 is not stopped after the stabilizing agent has been introduced. In yet other embodiments, after a droplet has been de-wetted from a surface of the microfluidic network, fluid flowing in the microfluidic network may be replaced by a second fluid (which may or may not contain a stabilizing agent). As shown in the embodiment illustrated in FIG. 5C, droplet 1080 can be removed/extracted from region 1028 in the direction of arrow 1088. One of ordinary skill in the art can determine appropriate conditions for de-wetting a droplet from a surface of the microfluidic network which may depend on conditions such as the concentration of the stabilizing agent in the fluid, the flow rate, the degree of wetting of the droplet, the contents of the droplet, the material composition of the fluidic network, as well as other factors.

Figure 6:
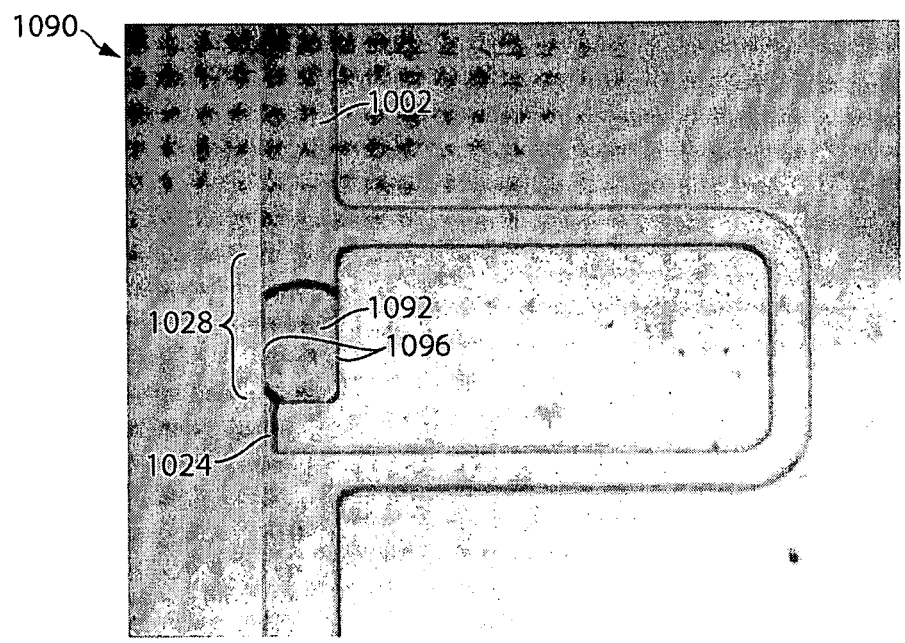
FIG. 6 is a photograph of a droplet wetting a surface of the microfluidic network according to another embodiment of the invention.
Figure 7:
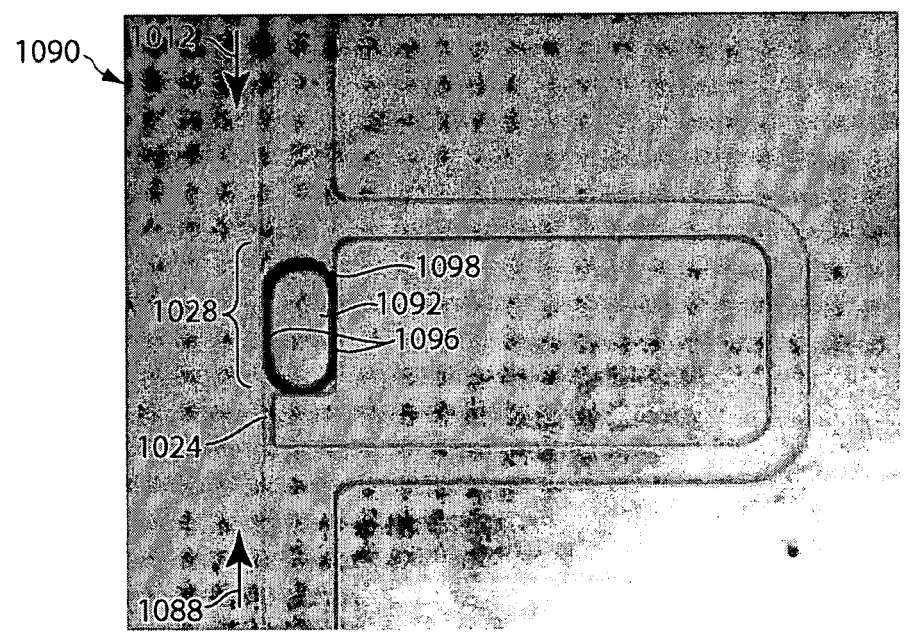
FIG. 7 shows de-wetting of the droplet from a surface of the microfluidic network after being treated with a stabilizing agent according to another embodiment of the invention.

FIG. 6 is a photograph showing droplet 1092 that has wetted surface portions 1096 of microfluidic network 1090 at region 1028. As shown in FIG. 7, after flowing a fluid containing a surfactant in the direction of arrow 1088, a portion of which flows through a narrow path portion 1024, droplet 1092 de-wets surface portions 1096 and is now stabilized with the stabilizing agent. The stabilization is evident by meniscus 1098 that forms around droplet 1092, as the droplet now takes on a lower energy state configuration compared to that shown in FIG. 6.

It should be understood that a fluid containing a stabilizing agent can be introduced into microfluidic network 1090 in any suitable manner. For example, in some embodiments, the stabilizing agent may be introduced by a fluid flowing in the direction of arrow 1012. In other embodiments, region 1028 may be in fluidic communication with another portion of the device branching from region 1028. For instance, above or below region 1028 may be a reservoir, a channel, or other component that can be used to introduce a stabilizing agent or other entity to a droplet in that region.

As shown in FIGS. 2 and 5, droplets that are released from a region of a microfluidic network can be caused to flow in a direction opposite that which was used to position the droplet in the region. In other embodiments, however, after a droplet has been removed from region in which it was positioned, the droplet may be caused to flow in the same direction as that which was used to position the droplet. For example, in one embodiment, droplet 1080 of FIG. 5C can be released from position 1028 and can be caused to flow in the direction of 1088 until the droplet resides at a downstream portion of channel 1002 (e.g., at the top of microfluidic network 1000 as shown in FIG. 5C). Then, a valve or other component that may be positioned at position 1070 can be at least partially closed to cause a higher resistance to fluid flow in fluid flow path 1014 compared to that of 1018. Since fluid flow path 1018 now has a lower resistance to fluid flow, flow of the carrier fluid can now be reversed such that it flows in the direction of arrow 1012, in which case the droplet can bypass fluid flow path 1014 and enter fluid flow path 1018.

As described above, methods for storing and/or extracting droplets in a microfluidic network are provided herein. In some embodiments, the droplets may be stored and/or extracted in sequential order. For example, the droplets may be extracted in the order they are stored or positioned in predetermined regions in the microfluidic network. Advantageously, in some embodiments, such methods do not require the use of surfactants or other stabilizing agents, since the droplets may not come into substantial physical contact with one another in a manner that causes coalescence. This is advantageous in certain cases as surfactants may interfere with contents such as proteins inside the droplet, as is known to those of ordinary skill in the art.

In some embodiments, the microfluidic networks shown in FIGS. 1-7 can be combined with one or more of the features shown in FIGS. 8-18 below. For instance, regions 1028 of FIG. 1A for positioning a droplet can replace microwells 2130 of FIGS. 8 and 14 and/or microwells or regions in other embodiments shown in FIGS. 8-18. Thus, the microfluidic networks of FIGS. 1-7 may be a part of the microfluidic chips described in connection with FIGS. 8-18 and may be connected to any suitable component shown in these figures.

As described above, microfluidic chips described herein may include a region for forming droplets of sample in a carrier fluid (e.g., an oil), and one or more microreactor regions (also called "predetermined regions" or "regions" herein) in which the droplets can be positioned and reaction conditions within the droplet can be varied. For instance, one such system includes microreactor regions containing several (e.g., 1000) microwells or other structures that are fluidically connected to a microchannel, or formed as a part of the microchannel. A reservoir (i.e., in the form of a chamber or a channel) for containing a gas or a liquid can be situated underneath a microwell, separating the microwell by a semi-permeable barrier (e.g., a dialysis membrane). In some cases, the semi-permeable barrier enables chemical communication of certain components between the reservoir and the microwell; for instance, the semi-permeable barrier may allow water, but not proteins, to pass across it. Using the barrier, a condition in the reservoir, such as concentration or ionic strength, can be changed (e.g., by replacing the fluid in the reservoir), thus causing the indirect change in a condition of a droplet positioned inside the microwell. This format allows control and the testing of many reaction conditions simultaneously. Microfluidic chips and methods of the invention can be used in a variety of settings. One such setting, described in more detail below, involves the use of a microfluidic chip for crystallizing proteins within aqueous droplets of fluid. Advantageously, crystallization conditions can be controlled such that nucleation and growth of crystals can be decoupled, performed reversibly, and controlled independently of each other, thereby enabling the formation of defect-free crystals.

Figure 8A:
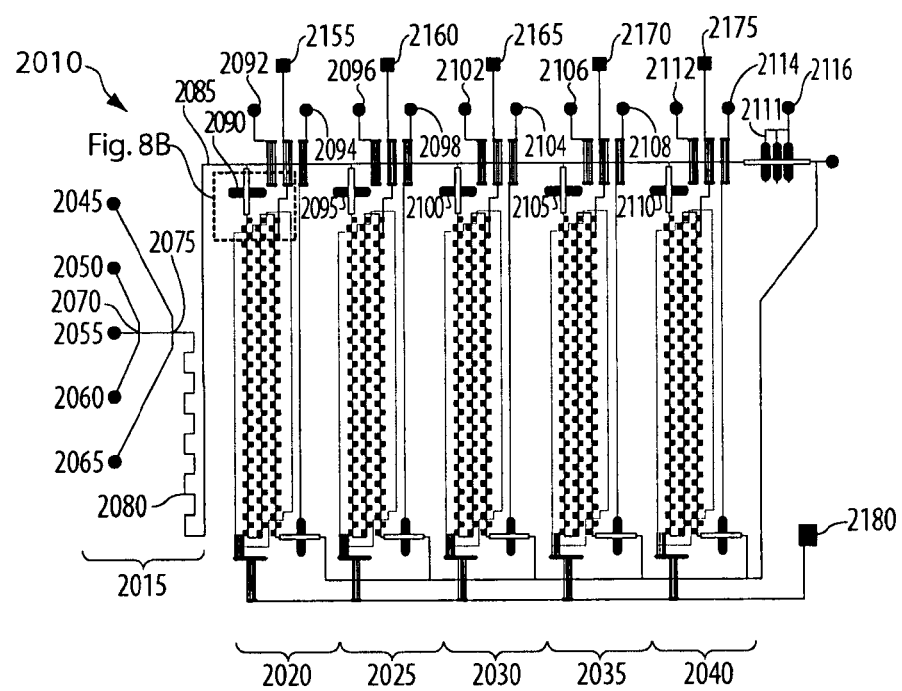
FIGS. 8A-8D show schematically a microfluidic device for manipulating fluids and reactions, according to another embodiment of the invention.
Figure 8B:
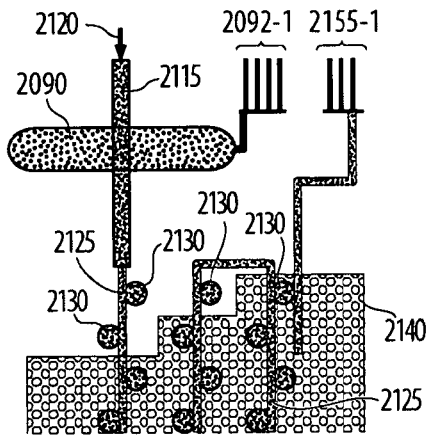
Figure 8C:
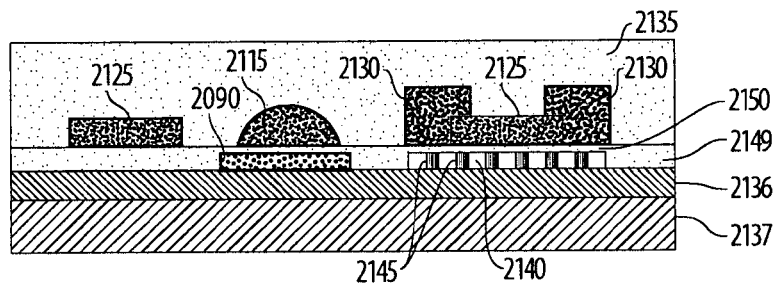

FIGS. 8A-8C illustrate a microfluidic chip 2010 according to one embodiment of the invention. As shown in FIG. 8A, microfluidic chip 2010 contains a droplet formation region 2015 connected fluidically to several microreactor regions 2020, 2025, 2030, 2035, and 2040. The droplet formation region can include several inlets 2045, 2050, 2055, 2060, and 2065, which may be used for introducing different fluids into the chip. For instance, inlets 2050, 2055, and 2060 may each contain different aqueous solutions necessary for protein crystallization. The rate of introduction of each of the solutions into inlets 2050, 2055, and 2060 can be varied so that the chemical composition of each of the droplets is different, as discussed in more detail below. Inlets 2045 and 2065 may contain a carrier fluid, such as an oil immiscible with the fluids in inlets 2050, 2055, and 2060. Fluids in inlets 2050, 2055, and 2060 can flow (i.e., laminarly) and merge at intersection 2070. When this combined fluid reaches intersection 2075, droplets of aqueous solution can be formed in the carrier fluid. Droplet formation region 2015 also includes a mixing region 2080, where fluids within each droplet can mix, e.g., by diffusion or by the generation of chaotic flows.

Droplets formed from region 2015 can enter one, or more, of microreactor regions 2020, 2025, 2030, 2035, or 2040 via channel 2085. The particular microreactor region in which the droplets enter can be controlled by valves 2090, 2095, 2100, 2105, 2110, and/or 2111, which can be activated by valve controls 2092, 2094, 2096, 2098, 2102, 2104, 2106, 2108, 2112, 2114, and/or 2116. For example, for droplets to enter microreactor region 2020, valve 2090 can be opened by activating valve controls 2092 and 2094, while valves 2095, 2100, 2105, 2110, and 2111 are closed. This may allow the droplets to flow into channel 2115 in the direction of arrow 2120, and then into channel 2125 and to several microwells 2130 (FIGS. 8B and 8C). As discussed in more detail below, each droplet can be positioned in a microwell, i.e., by the use of surface tension forces. Any of a number of valves and/or pumps, including peristaltic valves and/or pumps, suitable for use in a fluidic network such as that described herein can be selected by those of ordinary skill in the art including, but not limited to, those described in U.S. Pat. No. 6,767,194, "Valves and Pumps for Microfluidic Systems and Methods for Making Microfluidic Systems", and U.S. Pat. No. 6,793,753, "Method of Making a Microfabricated Elastomeric Valve," which are incorporated herein by reference.

As shown in FIG. 8C, microwells 2130 (as well as channels 2115 and 2125, and other components) can be defined by voids within structure 2135, which can be made of a polymer such as poly(dimethylsiloxane) (PDMS). Structure 2135 can be supported by optional support layers 2136 and/or 2137 which can be fully or partially polymeric or made of another substance including ceramic, silicon, or other material selected for structural rigidity suitable for the intended purpose of the particular device. As illustrated in this embodiment, reservoir 2140 and posts 2145 are positioned below microwells 2130 as part of layer 2149, and separate the microwells by a semi-permeable barrier 2150. In the embodiment illustrated in FIG. 8C, semi-permeable barrier is formed in layer 2149. In some instances, semi-permeable barrier 2150 allows certain low molecular weight components (e.g., water, vapor, gases, and low molecular weight organic solvents such as dioxane and iso-propanol) to pass across it, while preventing larger molecular weight components (e.g., salts, proteins, and hydrocarbon-based polymers) and/or certain fluorinated components (e.g., fluorocarbon-based polymers) from passing between microwells 2130 and reservoir 2140. By controlling the substances entering reservoir inlet 2155 (i.e., for microreactor region 2020), a condition (e.g., concentration, ionic strength, or type of fluid) in the reservoir can be changed. This can result in the change of a condition in microwells 2130 indirectly by a process such as diffusion and/or by flow of components past barrier 2150, as discussed below. Because there may be several (e.g., 1000) microwells on a chip, many reaction conditions can be tested simultaneously. Once a reaction has occurred in a droplet, the droplet can be transported, e.g., out of the device or to another portion of the device, for instance, via outlet 2180.

Figure 8D:
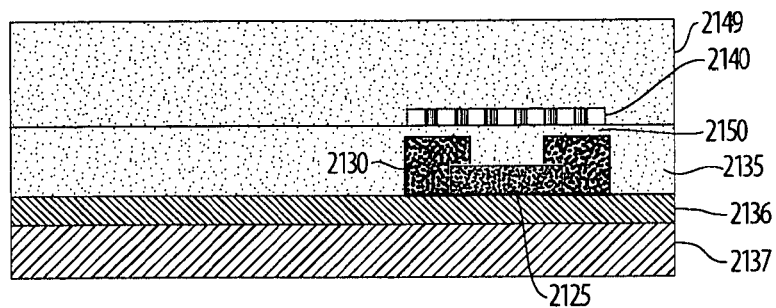

FIG. 8D shows an alternative configuration for the fabrication of device 2010. As illustrated in this figure, layer 2149 comprising reservoir 2140 is positioned above structure 2135 comprising microwells 2130 and channel 2125. In this embodiment, semi-permeable barrier 2150 is formed as part of structure 2135 i.e., by spin coating.

In the embodiment illustrated in FIG. 8D the membrane is fabricated as part of the layer containing the microwells, while as shown in FIG. 8C, the semi-permeable membrane is fabricated as part of the reservoir layer. In each case the layer containing the membrane can be thin (e.g., less than about 20 microns thick) and can be fabricated via spin coating, while the other layer(s) can be thick (e.g., greater than about 1 mm) and may be fabricated by casting a fluid. In other embodiments, however, semi-permeable barrier can be formed independently of layers 2149 and/or structure 2135, as described in more detail below.

It is to be understood that the structural arrangement illustrated in the figures and described herein is but one example, and that other structural arrangement can be selected. For example, a microfluidic network can be created by casting or spin coating a material, such as a polymer, from a mold such that the material defines a substrate having a surface into which are formed channels, and over which a layer of material is placed to define enclosed channels such as microfluidic channels. In another arrangement a material can be cast, spin-coated, or otherwise formed including a series of voids extending throughout one dimension (e.g., the thickness) of the material and additional material layers are positioned on both sides of the first material, partially or fully enclosing the voids to define channels or other fluidic network structures. The particular fabrication method and structural arrangement is not critical to many embodiments of the invention. In other cases, a particular structural arrangement or set of structural arrangements can define one or more aspects of the invention, as described herein.

Figure 9:
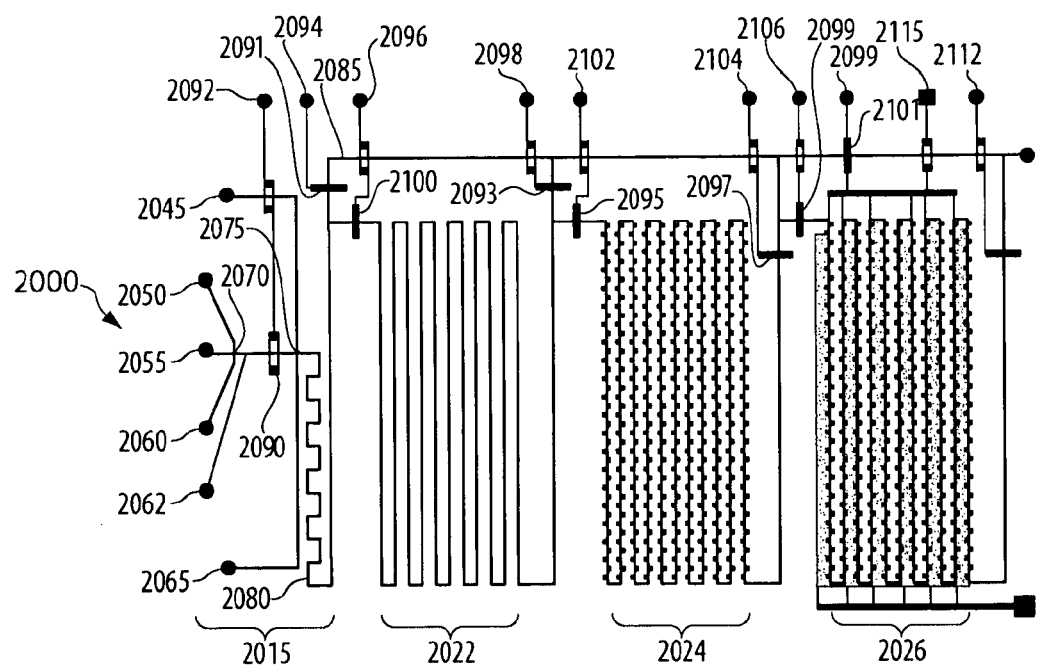
FIG. 9 shows schematically another microfluidic device for manipulating fluids and reactions, according to another embodiment of the invention.

FIG. 9 shows another exemplary design of a microfluidic chip, device 2000, which includes droplet formation region 2015, buffer region 2022, microwell region 2024, and microreactor region 2026. Buffer region 2022 can be used, for example, to allow a droplet formed in the droplet region to equilibrate with a carrier fluid. The buffer region is connected to microwell region 2024, which can be used for storing droplets. Microwell region 2024 is connected to microreactor region 2026, which contains microwells and reservoir channels positioned beneath the microwells, i.e., for changing a condition within droplets that are stored in the microwells. Droplets formed at intersection 2075 can enter regions 2022, 2024, or 2026, depending on the actuation of a series of valves. For instance, a droplet can enter buffer region 2022 by opening valve 2090 and 2100, while closing valve 2091. A droplet can enter microwell region 2024 directly by opening valves 2090, 2091, 2093, and 2095 while closing valves 2097, 2099, 2100, and 2101.

Figure 10A:
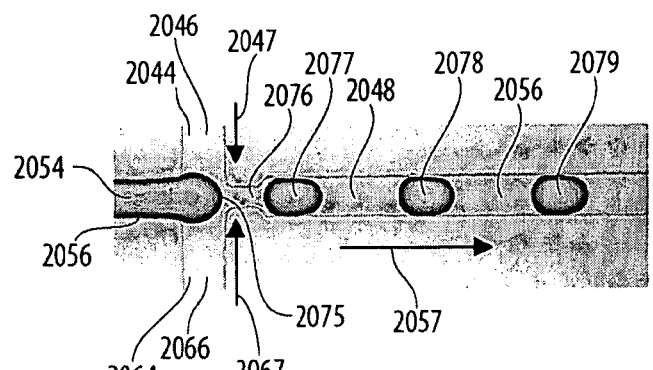
FIG. 10A is a photograph showing the formation of droplets, according to another embodiment of the invention.

The formation of droplets at intersection 2075 of device 2000 is shown in FIG. 10A. As shown in this diagram, fluid 2054 flows in channel 2056 in the direction of arrow 2057. Fluid 2054 may be, for example, an aqueous solution containing a mixture of components from inlets 2050, 2055, 2060, and 2062 (FIG. 9). Fluid 2044 flows in channel 2046 in the direction of arrow 2047, and fluid 2064 flows in channel 2066 in the direction of arrow 2067. In this particular embodiment, fluids 2044 and 2064 have the same chemical composition and serve as a carrier fluid 2048, which is immiscible with fluid 2054. In other embodiments, however, fluids 2044 and 2064 can have different chemical compositions and/or miscibilities relative to each other and to fluid 2054. At intersection 2075, droplets 2077, 2078, and 2079 are formed by hydrodynamic focusing after passing through nozzle 2076. These droplets are carried (or flowed) in channel 2056 in the direction of arrow 2057.

Droplets of varying sizes and volumes may be generated within the microfluidic system. These sizes and volumes can vary depending on factors such as fluid viscosities, infusion rates, and nozzle size/configuration. In some cases, it may be desirable for each droplet to have the same volume so that different conditions (e.g., concentrations) can be tested between different droplets, while the initial volumes of the droplets are constant. In other cases, it may be suitable to generate different volumes of droplets for use in an assay. Droplets may be chosen to have different volumes depending on the particular application. For example, droplets can have volumes of less than 1 µL, less than 0.1 µL, less than 10 nL, less than 1 nL, less than 0.1 nL, or less than 10 pL. It may be suitable to have small droplets (e.g., 10 pL or less), for instance, when testing many (e.g., 1000) droplets for different reaction conditions so that the total volume of sample consumed is low. On the other hand, large (e.g., 10 nL-1 µL) droplets may be suitable, for instance, when a reaction condition is known and the objective is to generate large amounts of product within the droplets.

The rate of droplet formation can be varied by changing the flow rates of the aqueous and/or oil solutions (or other combination of immiscible fluids defining carrier fluid and droplet, which behave similarly to oil and water, and which can be selected by those of ordinary skill in the art). Any suitable flow rate for producing droplets can be used; for example, flow rates of less than 100 nL/s, less than 10 nL/s, or less than 1 nL/s. In one embodiment, droplets having volumes between 0.1 to 1.0 nL can be formed while flow rates are set at 100 nL/s. Under these conditions, droplets can be produced at a frequency of 100 droplets/s. In another embodiment, the flow rates of two aqueous solutions can be varied, while the flow rate of the oil solution is held constant, as discussed in more detail below.

FIG. 11 shows one example of a method for positioning droplets within regions of a microfluidic channel. In the embodiment illustrated in FIG. 11A, carrier fluid 2048 flows in channel 2056 in the direction of arrow 2057 while droplets 2078 and 2079 are positioned in microwells 2082 and 2083, respectively. Droplet 2077 is carried in fluid 2048 also in the direction of arrow 2057. Droplet 2077 passes and may physically contact droplet 2079, but does not coalesce with droplet 2079 since the surfaces of the droplets may include a surfactant that prevents coalescence. As shown in FIG. 11B, when droplet 2077 is adjacent to microwell 2082, droplet 2077 tries to enter into this microwell. Since droplet 2078 has already occupied microwell 2082, however, droplet 2077 cannot fit and does not enter into this microwell. Meanwhile, the pressure of the carrier fluid pushes droplet 2077 forward in the direction of arrow 2057. When droplet 2077 passes an empty microwell, e.g., microwell 2081, droplet 2077 can enter and be positioned in this microwell (FIGS. 11D-11F). In a similar manner, the next droplet behind (i.e., to the left of) droplet 2077 can fill the next available microwell to the right of microwell 2081 (not shown). The passing of one droplet over another that has already been positioned into a microwell is referred to as the "leapfrog" method. In the leapfrog method, the most upstream microwell can contain the first droplet formed and the most downstream microwell can contain the last droplet formed.

Because droplets are carried past each other (e.g., as in FIGS. 11A-11C), and/or for other reasons involving various embodiments of the invention, a surfactant may be added to the droplet to stabilize the droplets against coalescence. Any suitable surfactant such as a detergent for stabilizing droplets can be used, including anionic, non-ionic, or cationic surfactants. In one embodiment, a suitable detergent is the non-ionic surfactant Span 80, which does not denature proteins yet stabilizes the droplets. Criteria for choosing other suitable surfactants are discussed in more detail below.

Different types of carrier fluids can be used to carry droplets in a device. Carrier fluids can be hydrophilic (i.e., aqueous) or hydrophobic (i.e., an oil), and may be chosen depending on the type of droplet being formed (i.e., aqueous or oil-based) and the type of process occurring in the droplet (i.e., crystallization or a chemical reaction). In some cases, a carrier fluid may comprise a fluorocarbon. In some embodiments, the carrier fluid is immiscible with the fluid in the droplet. In other embodiments, the carrier fluid is slightly miscible with the fluid in the droplet. Sometimes, a hydrophobic carrier fluid, which is immiscible with the aqueous fluid defining the droplet, is slightly water soluble. For example, oils such as PDMS and poly(trifluoropropylmethylsiloxane) are slightly water soluble. These carrier fluids may be suitable when fluid communication between the droplet and another fluid (i.e., a fluid in the reservoir) is desired. Diffusion of water from a droplet, through the carrier fluid, and into a reservoir containing air is one example of such a case.

Figure 11F:
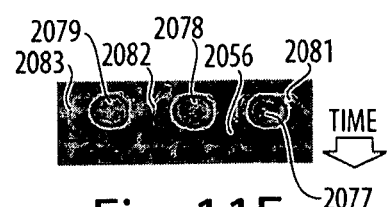
Figures 1, 11F:
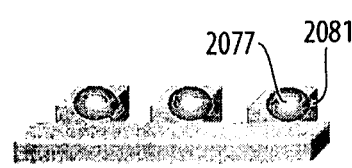

A droplet can enter into an empty microwell by a variety of methods. In the embodiment shown in FIG. 11A, droplet 2077 is surrounded by an oil and is forced to flow through channel 2056, which has a large width ($w_{56}$), but small height ($h_{56}$). Because of its confinement, droplet 2077 has an elongated shape while positioned in channel 2056, as the top, bottom, and side surfaces of the droplet take on the shape of the channel. This elongated shape imparts a high surface energy on the droplet (i.e., at the oil/water interface) compared to the same droplet having a spherical shape (i.e., of the same volume). When droplet 2077 passes an empty microwell 2081, which has a larger cross-sectional dimension (e.g., height, $h_{130}$) than that of channel 2056, droplet 2077 favors the microwell since the dimensions of the microwell allow the droplet to form a more spherical shape (as shown in FIG. 11F), thereby lowering its surface energy. In other words, when droplet 2077 is adjacent to empty microwell 2081, the gradient between the height of the channel and the height in the microwell produces a gradient in the surface area of the droplet, and therefore a gradient in the interfacial energy of the droplet, which generates a force on the droplet driving it out of the confining channel and into the microwell. Using this method, droplets can be positioned serially in the next available microwell (e.g., an empty microwell) while the carrier fluid is flowing. In other embodiments, methods such as patterned surface energy, electrowetting, and dielectrophoresis can drive droplets into precise locations in microfluidic systems.

In another embodiment, a method for positioning droplets into regions (e.g., microwells) of a microfluidic network comprises flowing a plurality (e.g., at least 2, at least 10, at least 50, at least 100, at least 500, or at least 1,000) of droplets in a carrier fluid in a microfluidic channel at a first flow rate. The first flow rate may be fast, for instance, for forming many droplets quickly and/or for filling the microfluidic network quickly with many droplets. At a fast flow rate, the droplets may not position into the regions. When the carrier fluid is flowed at a second flow rate slower than the first flow rate, however, each droplet may position into a region closest to the droplet and remain in the region. This method of filling microwells is referred to as the "fast flow/slow flow" method. Using this method, the droplets can be positioned in the order that the droplets are flowed into the channel, although in some instances, not every region may be filled (i.e., a first and a second droplet that are positioned in their respective regions may be separated by an empty region). Since this method does not require droplets to pass over filled regions (e.g., microwells containing droplets), as is the case as shown in FIG. 11, the droplets may not require surfactants when this method of positioning is implemented.

Figure 12A:
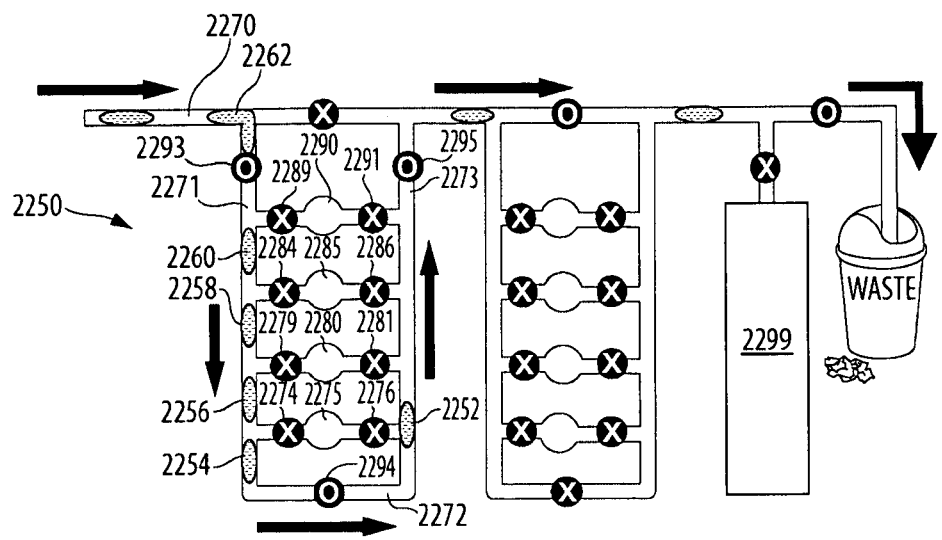
FIGS. 12A-12B show the positioning of droplets within microwells of a microfluidic device using valves to open and close the entrance and exits of microwells, according to another embodiment of the invention.
Figure 12B:
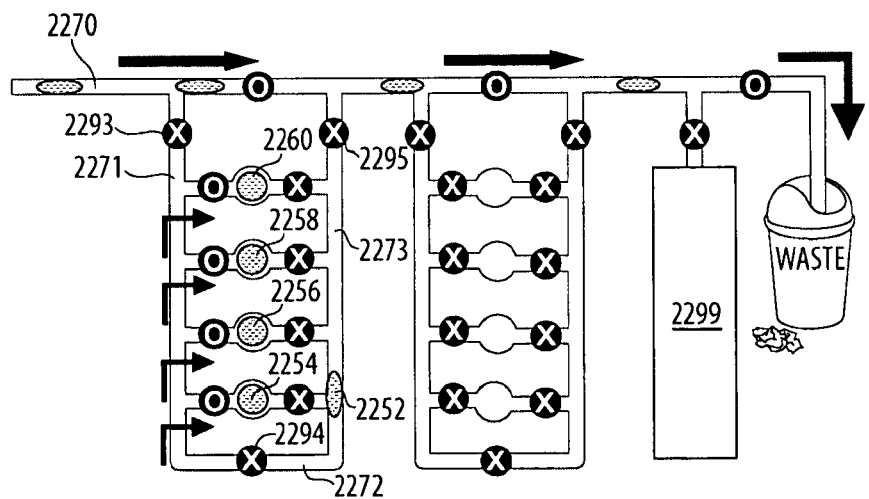

Another method for filling microwells in the order that the droplets are formed is by using valves at entrances and exits of the microwells, as shown in FIG. 12. In this illustrative embodiment, droplets 2252, 2254, 2256, 2258, 2260, and 2262 are flowed into device 2250 comprising channels 2270, 2271, 2272, and 2273, and microwells 2275, 2280, 2285, and 2290. Each microwell can have an entrance valve (e.g., valves 2274, 2279, 2284, and 2289) and an exit valve (e.g., valves 2276, 2281, 2286, and 2291) in either opened or closed positions. For illustrative purposes, opened valves are marked as "o" and closed valves are marked as "x" in FIG. 12. The droplets can flow in channels 2270, 2271, 2272, and 2273, i.e., when valves 2293, 2294, and 2295 are in the open position (FIG. 12A). Once the channels are filled, the flow in channels 2271, 2272, and 2273 can be stopped (i.e., by closing valves 2293, 2294, and 2295) and the entrance valves to the microwells can be opened (FIG. 12B). The droplets can position into the nearest microwell by surface tension or by other forces, as discussed below. If a concentration-dependent chemical process (e.g., crystallization) has occurred in a microwell, both the entrance and exit valves of that particular microwell can be opened while optionally keeping the other valves closed, and a product of the concentration-dependent chemical process (e.g., a crystal) can be flushed into vessel 2299, such as an x-ray capillary or a NMR tube, for further analysis.

Microwells may have any suitable size, volume, shape, and/or configuration, i.e., for positioning a droplet depending on the application. For example, microwells may have a cross-sectional dimension of less than about 250 µm, less than about 100 µm, or less than about 50 µm. In some embodiments, microwells can have a volume of less than 10 µL, less than 1 µL, less than 0.1 µL, less than 10 nL, less than 1 nL, less than 0.1 nL, or less than 10 pL. Microwells may have a large volume (e.g., 0.1-10 µL) for storing large droplets, or small volumes (e.g., 10 pL or less) for storing small droplets.

In the embodiment illustrated in FIG. 11, microwells 2081, 2082, and 2083 have the same dimensions. However, in certain other embodiments, the microwells can have different dimensions relative to one another, e.g., for holding droplets of different sizes. For instance, a microfluidic chip can comprise both large and small microwells, where large droplets may favor the large microwells and small droplets may favor the small microwells. By varying the size of the microwells and/or the size of the droplets on a chip, positioning of the droplets not only depends on whether or not the microwell is empty, but also on whether or not the sizes of the microwell and the droplet match. The positioning of different droplets of different sizes may be useful for varying reaction conditions within an assay.

In another embodiment, microwells 2081, 2082, and 2083 have different shapes. For example, one microwell may be square, another may be rectangular, and another may have a pyramidal shape. Different shapes of microwells may allow droplets to have different surface energies while positioned in the microwell, and can cause a droplet to favor one shape over another. Different shapes of microwells can also be used in combination with droplets of different size, such that droplets of certain sizes favor particular shapes of microwells.

Sometimes, a droplet can be released from a microwell, e.g., after a reaction has occurred inside of a droplet. Different sizes, shapes, and/or configurations of microwells may influence the ability of a droplet to be released from the microwell.

In some cases, the size of the microwell is approximately the same size as the droplet, as shown in FIG. 11. For instance, the volume of the microwell can be less than approximately twice the volume of the droplet. This is particularly useful for positioning a single droplet within a single microwell. In other cases, however, more than one droplet can be positioned in a microwell. Having more than one droplet in a microwell can be useful for applications that require the merging of two droplets into one larger droplet, and for applications that include allowing a component to pass (e.g., diffuse) from one droplet to another adjacent droplet.

Although many embodiments illustrated herein show the positioning of droplets in microwells, in some cases, microwells are not required for positioning droplets. For instance, in some cases, a droplet is positioned in a region in fluid communication with the channel, the region having a different affinity for the droplet than does another part of the channel. The region may be positioned on a wall of the channel. In one embodiment, the region can protrude from a surface (e.g., a side) of the channel. In another embodiment, the region can have at least one dimension (e.g., a width or height) larger than a dimension of the channel. A droplet that is carried in the channel may be positioned into the region by the lowering of the surface energy of the droplet when positioned in the region, relative to the surface energy of the droplet prior to being positioned in the region.

In another embodiment, positioning of a droplet does not require the use of differences in dimension between the region and the channel. A region may have a patterned surface (e.g., a hydrophobic or hydrophilic patch, a surface patterned with a specific chemical moiety, or a magnetic patch) that favors the positioning and/or containing of a droplet. Different methods of positioning, e.g., based on hydrophobic/hydrophilic interactions, magnetic interactions, or electrical interactions such as dielectrophoresis, electrophoresis, and optical trapping, as well as chemical interactions (e.g., covalent interactions, hydrogen-bonding, van der Waals interactions, and adsorption) between the droplet and the first region are possible. In some cases, the region may be positioned in, or adjacent to, the channel, for example.

In some instances, a condition within a droplet can be controlled after the droplet has been formed. For example, FIG. 13 shows an example of a microreactor region 2026 of device 2000 (FIG. 9). The microreactor region can be used to control a condition in a droplet indirectly, e.g., by changing a condition in a reservoir adjacent to a microwell rather than by changing a condition in the microwell directly. Region 2026 includes a series of microwells used to position droplets 2201-2208, the microwells and droplets being separated from reservoir 2140 by semi-permeable barrier 2150. In this particular example, all droplets contain a saline solution and are surrounded by an immiscible oil. As shown in the figure, some droplets (droplets 2201-2204) are positioned in microwells that are farther away from the reservoir than others (droplets 2205-2208). As such, a change in a condition in reservoir 2140 has a greater immediate effect on droplets 2205-2208 than on droplets 2201-2204. Droplets 2201-2208 initially have the same volume in microreactor region 2026 (not shown).

FIGS. 13A (top view) and 13B (side view of droplets 2201, 2204, 2206, 2207) show an effect that can result from circulating air in the reservoir. Air in the reservoir, in certain amounts and in connection with conditions that can be selected by those of ordinary skill in the art based upon this disclosure (e.g. amount, flow rate, temperature, etc. taken in conjunction with the makeup of the droplets) can cause droplets 2205-2208 to decrease in volume more than that of droplets 2201-2204, since droplets 2205-2208 are positioned closer to the reservoir than droplets 2201-2204. Through the process of permeation, fluids in the droplets can move across the semi-permeable barrier, causing the volume of the droplets to decrease. As shown in FIGS. 13C (top view) and 13D (side view of droplets 2201, 2204, 2206, 2207), under appropriate conditions flowing water in the reservoir instead of air reverses this process. Small droplets 2205-2208 of FIGS. 13A and 13B can swell, as illustrated in FIGS. 13C and 13D because, for instance, the droplets may contain a saline solution or otherwise have an appropriate difference in osmotic potential compared to the surrounding environment. This difference in osmotic potential can cause water to diffuse from the reservoir, across the semi-permeable barrier, through the oil, and into the droplets. Droplets farther away from the reservoir (droplets 2201-2204) may initially remain small, since it takes a longer time for water to diffuse across a longer distance (e.g., diffusion time scales with the square of the distance). At equilibrium, the chemical potentials of the fluid in the reservoir and the fluid in the droplets generally will be equal.

As shown in FIG. 13, reservoir 2140 is in the form of a microfluidic channel. In other embodiments, however, the reservoir can take on different forms, shapes, and/or configurations, so long as it can be used to store a fluid. For instance, as shown in FIG. 8C, reservoir 2140 is in the form of a chamber, and a series of microfluidic channels 2155-1 allow fluidic access to the chamber (i.e., to introduce different fluids into the reservoir). Sometimes, reservoirs can have components such as posts 2145, which may give structured support to the reservoir.

A fluidic chip can include several reservoirs that are controlled independently (or dependently) of each other. For instance, a device can include greater than 1, great than 5, greater than 10, greater than 100, greater than 1,000, or greater than 10,000 reservoirs. A large number (e.g., 100 or more) of reservoirs may be suitable for a chip in which reservoirs and microwells are paired such that a single reservoir is used to control conditions in a single microwell. A small number (e.g., 10 or less) of reservoirs may be suitable when it is favorable for many microwells to experience the same changes in conditions relative to one another. This type of system can be used, for example, for increasing the size of many droplets (i.e., diluting components within the droplets) simultaneously.

Reservoir 2140 typically has at least one cross-sectional dimension in the micron-range. For instance, the reservoir may have a length, width, or height of less than 500 µm, less than 250 µm, less than 100 µm, less than 50 µm, less than 10 µm, or less than 1 µm. The volume of the reservoir can also vary; for example, it may have a volume of less than 50 µL, less than 10 µL, less than 1 µl, less than 100 nL, less than 10 nL, less than 1 nL, less than 100 pL, or less than 10 pL. In one particular embodiment, a reservoir can have dimensions of 10 mm by 3 mm by 50 µm and a volume of less than 20 µL.

A large reservoir (e.g., a reservoir having a large cross-sectional dimension and/or a large volume) may be useful when the reservoir is used to control the conditions in several (e.g., 100) microwells, and/or for storing a large amount of fluid. A large amount of fluid in the reservoir can be useful, for example, when droplets are stored for a long time (i.e., since, in some embodiments, material from the droplet may permeate into surrounding areas or structures over time). A small reservoir (e.g., a reservoir having a small cross-sectional dimension and/or a small volume) may be suitable when a single reservoir is used to control conditions in a single microwell and/or for cases where a droplet is stored for shorter periods of time.

Semi-permeable barrier 2150 is another factor that controls the rate of equilibration or the rate of passage of a component between the reservoir and the microwells. In other words, the semi-permeable barrier controls the degree of chemical communication between two sides of the barrier. Examples of semi-permeable barriers include dialysis membranes, PDMS membranes, polycarbonate films, meshes, porous layers of packed particles, and the like. Properties of the barrier that may affect the rate of passage of a component across the barrier include: the material in which the barrier is fabricated, thickness, porosity, surface area, charge, and hydrophobicity/hydrophilicity of the barrier.

The barrier may be fabricated in any suitable material and/or in any suitable configuration in order to permit one set of components and inhibit another set of components from crossing the barrier. In one embodiment, the semi-permeable barrier comprises the material from which the reservoir is formed, i.e., as part of layer 2149 as shown in FIG. 8C, and can be formed in the same process in which the reservoir is formed (i.e., the reservoir and the barrier can be formed in a single process in which a precursor fluid is spin-coated or solution-cast onto a mold and subsequently hardened to form both the barrier and reservoir in a single step, or, alternatively, another process in which the barrier and reservoir are formed from the same material, optionally simultaneously). In another embodiment, the semi-permeable barrier comprises the same material as the structure of the device, i.e., as part of structure 2135 as shown in FIG. 8D, and can be formed in conjunction with the structure 2135 as described above in connection with the semi-permeable barrier and reservoir, optionally. For instance, all, or a portion of, the barrier can be formed in the same material as the structure layer and/or reservoir layer. In some cases, the barrier can be fabricated in a mixture of materials, one of the materials being the same material as the structure layer and/or reservoir layer. Fabricating the barrier in the same material as the structure layer and/or reservoir layer offers certain advantages such as easy integration of the barrier into the device. In other embodiments, the semi-permeable barrier is fabricated as a layer independent of the structure layer and reservoir layer. The semi-permeable barrier can be made in the same or a different material than the other layers of the device.

In some cases, the barrier is fabricated in a polymer (e.g., a siloxane, polycarbonate, cellulose, etc.) that allows passage of a first set of low molecular weight components, but inhibits the passage of a second set of large molecular weight components across the barrier. For instance, a first set of low molecular weight components may include water, gases (e.g., air, oxygen, and nitrogen), water vapor (e.g., saturated or unsaturated), and low molecular weight organic solvents (e.g., hexadecane), and the second set of large molecular weight components may include proteins, polymers, amphiphiles, and/or others species. Those of ordinary skill in the art can readily select a suitable material for the barrier based upon e.g., its porosity, its rigidity, its inertness to (i.e., freedom from degradation by) a fluid to be passed through it, and/or its robustness at a temperature at which a particular device is to be used.

The semi-permeable barrier may have any suitable thickness for allowing one set of components to pass across the barrier while inhibiting another set of components. For example, a semi-permeable barrier may have a thickness of less than 10 mm, less than 1 mm, less than 500 µm, less than 100 µm, less than 50 µm, or less than 20 µm, or less than 1 µm. A thick barrier (e.g., 10 mm) may be useful for allowing slow passage of a component between the reservoir and the microwell. A thin barrier (e.g., less than 20 µm thick) can be used when it is desirable for a component to be passed quickly across the barrier.

For size exclusive semi-permeable barriers (i.e., including dialysis membranes), the pores of the barriers can have different shapes and/or sizes. In one embodiment, the sizes of the pores of the barrier are based on the inherent properties of the barrier, such as the degree of cross-linking of the material in which the barrier is fabricated. In another embodiment, the pores of the barrier are machine-fabricated in a film of a material. Semi-permeable barriers may have pores sizes of less than 100 µm, less than 10 µm, less than 1 µm, less than 100 nm, less than 10 nm, or less than 1 nm, and may be chosen depending on the component to be excluded from crossing the barrier.

A semi-permeable barrier may exclude one or more components from passing across it by methods other than size-exclusion, for example, by methods based on charge, van der Waals interactions, hydrophilic or hydrophobic interactions, magnetic interactions, and the like. For instance, the barrier may inhibit magnetic particles but allow non-magnetic particles to pass across it (or vice versa).

Different methods of passing a component across the semi-permeable barrier can be used. For instance, in one embodiment, the component may diffuse across the barrier if there is a difference in concentration of the component between the microwell and the reservoir. In another embodiment, if the component is water, water can pass across the barrier by osmosis. In yet another embodiment, the component can evaporate across the barrier; for instance, a fluid in the microwell can evaporate across the barrier if a gas is positioned in the reservoir. In some cases, the component can cross the barrier by bulk or mass flow in response to a pressure gradient in the microwell or the reservoir. In other cases, the component can cross the barrier by methods such as facilitated diffusion or by active transport. A combination of modes of transport can also be applied. Typically, however, the barrier is not constructed and arranged to be operatively opened and closed to permit and inhibit fluid flow in the reservoir, microwell, or microchannel. For instance, in one embodiment, the barrier does not act as a valve that can operatively open and close to allow and block, respectively, fluidic access to the reservoir, microwell, or microchannel.

In some cases, the barrier is positioned in a device such that fluid can flow adjacent to a first side of the barrier without the need for the fluid to flow through the barrier. For instance, in one embodiment, a barrier is positioned between a reservoir and a microwell; the reservoir has an inlet and an outlet that allow fluidic access to it, and the microwell is fluidically connected to a microchannel having an inlet and an outlet, which allow fluidic access to the microwell. Fluid can flow in the reservoir without necessarily passing across the barrier (i.e., into the microchannel and/or microwell), and the same or a different fluid can flow in the microchannel and/or microwell without necessarily passing across the barrier (i.e., into the reservoir).

FIG. 14 shows that device 2010 can be used to grow, and control the growth of, a precipitate such as crystal inside a microwell of the device. In this particular embodiment, droplet 2079 is aqueous and contains a mixture of components, e.g., a protein, a salt, and a buffer solution, for generating a crystal. The components are introduced into the device via inlets 2050, 2055, and/or 2060. An immiscible oil introduced into inlets 2045 and 2065 serves as carrier fluid 2048. As shown schematically in FIG. 14B, droplet 2079 is surrounded by carrier fluid 2048 in microwell 2130. Semi-permeable barrier 2150 separates the microwell from reservoir 2140, which can contain posts 2145.

Figure 14A:
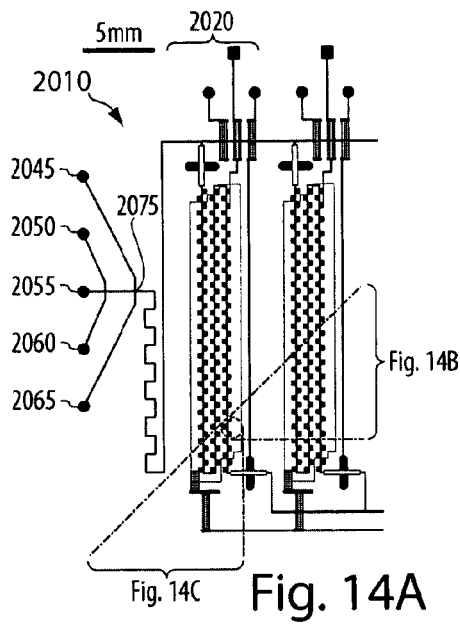
FIGS. 14A-14G illustrate the processes of nucleation and growth of crystals inside a microwell of a device, according to another embodiment of the invention.
Figure 14B:
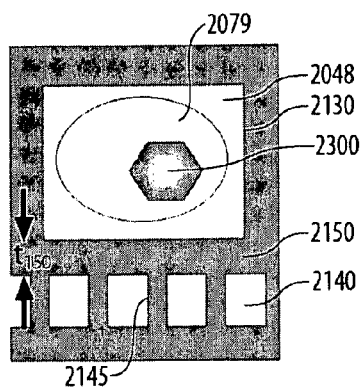
Figure 14C:
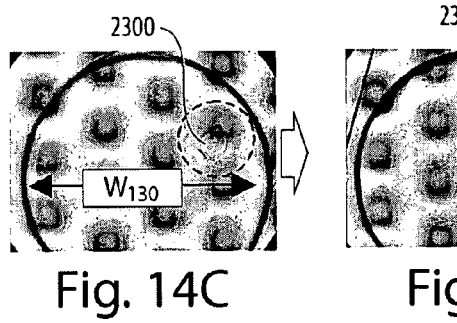

Protein in droplet 2079 can be nucleated to form crystal 2300 by concentrating the protein solution within the droplet (FIG. 14C). If the protein solution is concentrated to a certain degree, the solution becomes supersaturated and suitable for crystal growth. In one embodiment, the protein solution is concentrated by flowing air in reservoir 2150, which causes water in the droplet to evaporate across the semi-permeable barrier while the protein remains in the droplet. In another embodiment, a high ionic strength buffer (i.e., a buffer having higher ionic strength than the ionic strength of the fluid defining the to droplet) is flowed in the reservoir. The imbalance of chemical potential between the two solutions causes water to diffuse from the droplet to reservoir. Other methods for concentrating the solution within the droplet can also be used.

Other methods for nucleating a crystal can also be applied. For instance, two droplets, each of which contain a component necessary for protein crystallization, can be positioned in a single microwell. The two droplets can be fused together into a single droplet, i.e., by changing the concentration of surfactant in the droplets, thereby causing the components of the two droplets to mix. In some cases, these conditions may be suffice to cause nucleation.

Figure 14D:
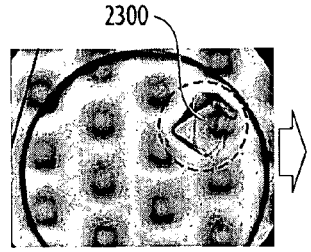

As shown in FIGS. 14C and 14D, once crystal 2300 is nucleated in a droplet, the crystal grows spontaneously within a short period of time (e.g., 10 seconds) since the crystal is surrounded by a supersaturated solution (as discussed in more detail below). In some cases, this rapid growth of the crystal leads to poor-quality crystals, since defects do not have time to anneal out of the crystal. One solution to this problem is to change the conditions of the sample during the crystallization process. Ideal crystal growing conditions occur when the sample is temporarily brought into deep supersaturation where the nucleation rate is high enough to be tolerable. In the ideal scenario, after a crystal has nucleated, the supersaturation of the solution would be decreased, e.g., by lowering the protein or salt concentrations or by raising temperature, in order to suppress further crystal nucleation and to establish conditions where slow, defect free crystal growth occurs. Device 2010 can allow this process to occur by decreasing the size of a crystal after it has nucleated and grown, and then re-growing the crystal slowly under moderately supersaturated conditions. Thus, the processes of nucleation and growth can be performed reversibly, and can occur independently of each other, in embodiments such as device 2010.

Figure 14E:
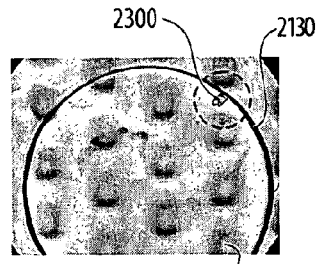

To decrease the size of the crystal (i.e., so that the crystal can be re-grown to become defect-free), reservoir 2140 can be filled with a buffer of lower salt concentration than that of the protein solution in the droplet. This causes water to flow in the opposite direction, i.e., from the reservoir to the protein solution, which dilutes the protein and the precipitant (e.g., by increasing the volume of the droplet), suppresses further nucleation, and slows down growth (FIG. 14E). To re-grow the crystal under slower and more moderately supersaturated conditions, the fluid in the reservoir can be replaced by a solution having a higher salt concentration such that fluid diffuses slowly out of the droplet, thereby causing the protein in the droplet to concentrate.

If the dialysis step of decreasing the size of the crystal proceeds long enough that the crystal dissolves completely, this system (e.g., device 2010) can advantageously allow the processes of nucleation and growth to be reversed, i.e., by changing the fluids in the reservoir. In addition, if small volumes of the droplets (e.g., ~nL) are used in this system, the device allows faster equilibration times between the droplet and the reservoir than for microliter-sized droplets, which are used in conventional vapor diffusion-based crystallization techniques (e.g., hanging or sitting drop techniques).

Figure 14F:
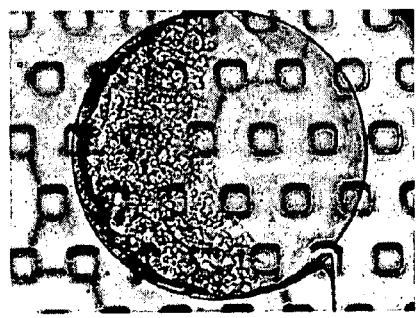
Figure 14G:
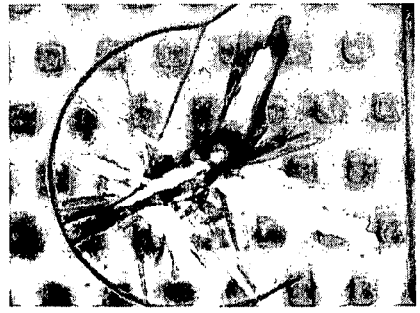

In some cases, concentrating the protein solution within the droplet causes the nucleation of precipitate (FIG. 14F). The precipitate may comprise largely non-crystalline material, largely crystalline material, or a combination of both non-crystalline and crystalline material, depending on the growth conditions applied. Device 2010 can be used to dilute the protein solution in the droplet, which can cause some, or all, of the precipitate to dissolve. Sometimes, the precipitate is dissolved until a small portion of the precipitate remains. For instance, dissolving may cause the smaller portions of the precipitate to dissolve, allowing one or a few of the largest portions to remain; these remaining portions can be used as seeds for growing crystals. After a seed has been formed, the concentration of protein in the droplet can be increased slowly (e.g., by allowing water to diffuse slowly out of the droplet). This process can allow the formation of large crystals within the droplet (FIG. 14G).

As shown in FIGS. 14A-14G, processes such as nucleation, growth, and dissolution of a crystal can all occur within a droplet while the droplet is positioned in the same microwell. In other embodiments, however, different processes can occur in different parts or regions of the fluidic network. For instance, nucleation and dissolution of a crystal can take place in a small (e.g., 10 pL) droplet in a small microwell, and then the droplet containing the crystal can be transported to a larger microwell for re-growth of the crystal in a larger (e.g., 1 nL) droplet. This process may allow small amounts of reagent to be consumed for the testing of reaction conditions and larger amounts of reagent to be used when reaction conditions are known. In some cases, this process decreases the overall amount of reagent consumed, as discussed in more detail below.

Device 2010 of FIG. 15 can be used to form many droplets of different composition, and to precisely control the rate and duration of supersaturation of the protein solution within each droplet. The rate of introduction of protein, salt, and buffer solutions into inlets 2050, 2055, and 2060 can be varied so that the solutions can be combinatorially mixed with each other to produce several (e.g., 1000) droplets having different chemical compositions. In one embodiment, each droplet has the same volume (e.g., 2 nL), and each droplet can contain, for instance, 1 nL of protein solution and 1 nL of the other solutes. The rate of introducing the protein solution can be held constant, while the rates of introducing the salt and buffer solutions can vary. For example, injection of the salt solution can ramp up linearly in time (e.g., from 0 to 10 nL/s), while injection of the buffer solution ramps down linearly in time (e.g., from 10 to 0 nL/s). In another embodiment, the rate of introducing a protein can vary while one of the other solutes is held constant. In yet another embodiment, all solutions introduced into the device can be varied, i.e., in order to make droplets of varying sizes. Advantageously, this setup can allow many different conditions for protein crystallization to be tested simultaneously.

Figure 15A:
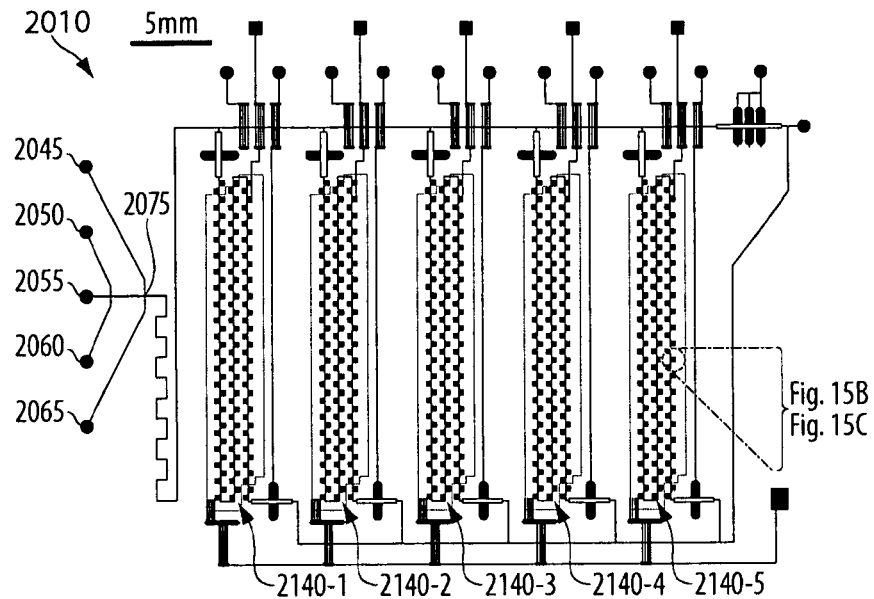
FIGS. 15A-15C show the increase and decrease of the size of a crystal inside a microwell of a device, according to another embodiment of the invention.
Figure 15B:
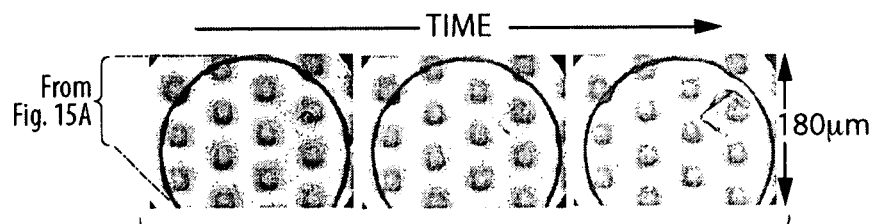
Figure 15C:
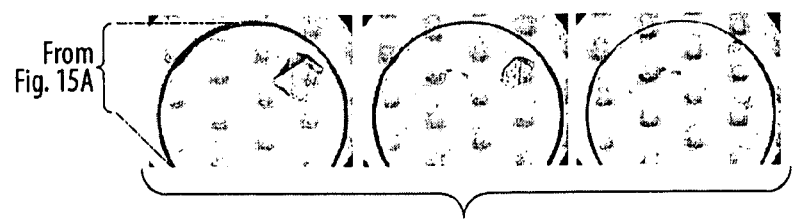

In addition to varying the concentration of solutes within each droplet, the environmental factors influencing crystallization can be changed. For instance, device 2010 includes five independent reservoirs 2140-1, 2140-2, 2140-3, 2140-4, and 2140-5 that can contain solutions of different chemical potential. These reservoirs can be used to vary the degree of supersaturation of the protein solution within the droplets. Thus, the nucleation rate of the first crystal produced and the growth rate of the crystal can be controlled precisely within each droplet. Examples of controlling the sizes of crystals are shown in FIGS. 15B and 15C, and in Example 3.

Figure 16A:
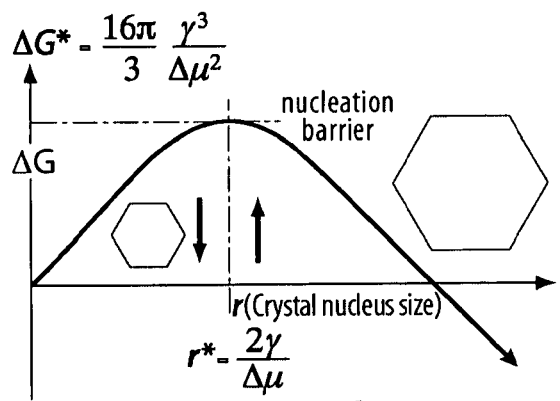
FIG. 16A is a plot showing the relationship between free energy and crystal nucleus size, according to another embodiment of the invention.
Figure 16B:
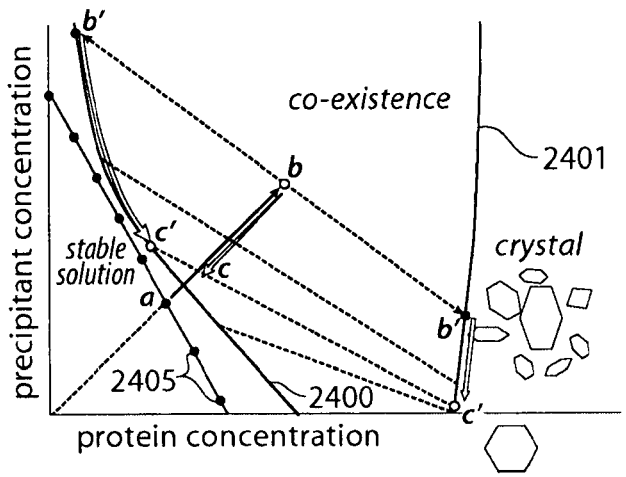
FIG. 16B is a phase diagram showing the relationship between precipitation concentration and protein concentration, according to another embodiment of the invention.

FIG. 16B is a phase diagram illustrating the use of a reservoir to change a condition in a droplet (i.e., by reversible dialysis). At low protein concentrations, a protein solution is thermodynamically stable (i.e., in the stable solution phase). An increase in concentration of a precipitant, such as salt or poly(ethylene) glycol (PEG), drives the protein into a region of the phase diagram where the solution is metastable and protein crystals are stable (i.e., in the co-existence phase). In this region, there is a free energy barrier to nucleating protein crystals and the nucleation rate can be extremely slow (FIG. 16A). At higher concentrations, the nucleation barrier is suppressed and homogeneous nucleation occurs rapidly (i.e., in the crystal phase). As mentioned above, at high supersaturation, crystal growth is rapid and defects may not have time to anneal out of the crystal, leading to poor quality crystals. Thus, production of protein crystals requires two conditions that work against each other. On one hand, high supersaturation is needed for nucleating crystals, but on the other hand, low supersaturation is necessary for crystal growth to proceed slowly enough for defects to anneal away. Changing sample conditions during the crystallization process is one method for solving this problem. Ideal crystal growing conditions occur when the sample is temporarily brought into deep supersaturation where the nucleation rate is high enough to be tolerable. In the ideal scenario, after a few crystals have nucleated, the supersaturation of the solution would be decreased by either lowering the protein or salt concentrations, or by raising temperature in order to suppress further crystal nucleation and to establish conditions where slow, defect free crystal growth occurs. In other words, independent control of nucleation and growth is desired.

Figure 17:
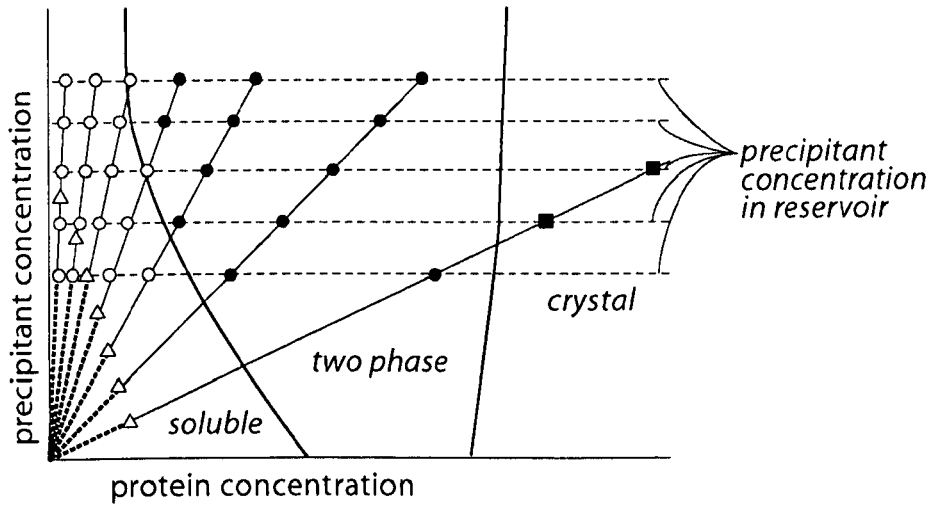
FIG. 17 is another phase diagram showing the relationship between precipitation concentration and protein concentration, according to another embodiment of the invention.

As shown in FIG. 16B, a microfluidic device (e.g., device 2010) of the present invention can be used to independently control nucleation and growth of a crystal. In FIG. 16B, lines 2400 and 2401 separate the liquid-crystal phase boundary. Dashed tie-lines connect co-existing concentrations, with crystals high in protein and low in precipitant (e.g., polyethylene glycol (PEG)). For clarity, the composition trajectory for one initial condition is shown here, while FIG. 17 shows trajectories for multiple initial and final conditions. Reversible microdialysis can be shown in three steps. Step 1: Initial concentrations of solutions in the droplets are stable solutions (circles 2405—points a). Step 2: Dialysis against high salt or air (e.g., in the reservoir) removes water from the droplet, concentrating the protein and precipitant within the droplet (path a→b). At point b, the solution is metastable and if crystals nucleate, then phase separation occurs along tie-lines (b→b'), producing small crystals that grow rapidly. Step 3: Dialysis against low salt water dilutes the protein and precipitant within the droplets, which lowers $\Delta\mu$ and increases $\Delta G^*$ and $r^*$. This suppresses further nucleation, causes the small crystals to dissolve adiabatically along the equilibrium phase boundary (b'→c'), and slows the growth of the remaining large crystals. If there was no nucleation at point b, then the metastable solution would evolve from b→c. Step 4: If necessary, crystalline defects can be annealed away by alternately growing and shrinking individual crystals b'⇌c', which is accomplished by appropriately varying the reservoir conditions.

The size of a crystal that has been formed in a droplet can vary (i.e., using device 2010 of FIG. 15). For example, a crystal may have a linear dimension of less than 500 μm, less than 250 μm, less than 100 μm, less than 50 μm, less than 25 μm, less than 10 μm, or less than 1 μm. Some of these crystals can be used for X-ray diffraction and for structure determination. For instance, consider the crystals formed in 1 nL droplets. If the concentration of the protein solution introduced into the device is 10 mg/mL=10 μg/μL, then 1 μL of protein solution only contains 10 μg of protein. In the device, 1 μL of protein solution can produce 1,000 droplets of different composition, for example, each droplet containing 1 nL of protein solution and 1 nL of other solutes, as described above. The linear dimension of a 1 nL drop is 100 μm and if the crystal is 50% protein, then the crystal will have a volume 50 times smaller than the protein solution, or 20 pL. The linear dimension of a cubic crystal of 20 pL volume is roughly 25 μm, and X-ray diffraction and structure determination from such small crystals is possible.

In another embodiment, a device having two sections can be used to form crystals. The first section can be used to screen for crystallization conditions, for instance, using very small droplet volumes (e.g., 50 pL), which may be too small for producing protein crystals for X-ray diffraction and for structure determination. Once favorable conditions have been screened and identified, the protein stock solution can be diverted to a second section designed to make droplets of larger size (e.g., 1 nL) for producing crystals suitable for diffraction. Using such a device, screening, e.g., 1000 conditions at 50 pL per screen, consumes only 0.5 μg of protein. Scaling up a subset of 50 conditions to 1 nL (e.g., the most favorable conditions for crystallization) consumes another 0.5 μg of protein. Thus, it can be possible to screen 1000 conditions for protein crystallization using a total of 1 μg of protein.

In some cases, it is desirable to remove the proteins formed within the microwells of the device, for instance, to load them into vessels such as x-ray capillaries for performing x-ray diffraction, as shown in FIG. 12. In one embodiment, a microfluidic device comprises microwells that are connected to an exhaust channel and a valve that controls the passage of components from the microwell to the exhaust channel. Using the multiplexed valves, it is possible to control n valves with 2 $\log_2$ n pressure lines used to operate the valves. Droplets can first be loaded into individual microwells using surface tension forces as describe above. Then, individual microwells can be addressed in arbitrary order (e.g., as in a random access memory (RAM) device) and crystals can be delivered into x-ray capillaries. Many (e.g., 100) crystals, each isolated from the next by a plug of immiscible fluid (e.g., water-insoluble oil), can be loaded into a single capillary for diffraction analysis.

As the number of crystallization trials grows, it may be advantageous to automate the detection of crystals. In one embodiment, commercial image processing programs that are interfaced to optical microscopes equipped with stepping motor stages are employed. This software can identify and score "hits" (e.g., droplets and conditions favorable for protein crystallization). This subset of all the crystallization trials can be scanned and select crystals can be transferred to the x-ray capillary.

In another embodiment, a microfluidic device has a temperature control unit. Such a device may be fabricated in PDMS bonded to glass, or to indium tin oxide (ITO) coated glass, i.e., to improve thermal conductivity. Two thermoelectric devices can be mounted on opposite sides of the glass to create a temperature gradient. Thermoelectric devices can supply enough heat to warm or cool a microfluidic device at rates of several degrees per minute over a large temperature range. Alternatively, thermoelectric devices can maintain a stable gradient across the device. For example, device 2010 shown in FIG. 15A can have a thermoelectric device set at 40° C. on the left end (i.e., near reservoir 2140-1) and at 4° C. on the right end (i.e., near reservoir 2140-5). This arrangement can enable each of the reservoirs in between the left and right ends to reside at different temperatures. Temperature can be used as a thermodynamic variable, in analogy to concentration in FIG. 16B, to help decouple nucleation and growth.

In some cases, surfactants are required to prevent coalescence of droplets. For instance, in one embodiment, several droplets can be positioned adjacent to each other in a channel without the use of microwells, i.e., the droplets can line themselves in different arrangements along the length of the channel. In this embodiment, as well as embodiments that involve the passing of droplets beside other droplets (FIG. 11), a surfactant is required to stabilize the droplets. For each type of oil (i.e., used as a carrier fluid), there exists an optimal surfactant (i.e., an optimum oil/surfactant pair). For example, for a device that is fabricated in PDMS, the ideal pair includes a surfactant that stabilizes an aqueous droplet and does not denature the protein, and an oil that is both insoluble in PDMS, and has a water solubility similar to PDMS. Hydrocarbon-based oils such as hexadecane and dichloromethane can be poor choices, since these solvents swell and distort the PDMS device after several hours. The best candidates may be fluorocarbons and fluorosurfactants to stabilize the aqueous solution because of the low solubility of both PDMS and proteins in fluorinated compounds. The use of a hydrocarbon surfactant to stabilize protein droplets could interfere with membrane protein crystallization of protein-detergent complexes, although it is also possible that surfactants used in the protein-detergent complex also stabilizes the oil/water droplets. In one embodiment, hexadecane is used to create aqueous droplets with a gentle non-ionic detergent (e.g., Span-80) to stabilize the droplets. After the droplets are stored in the microwells, the hexadecane and Span-80 can be flushed out and replaced with fluorocarbon or paraffin oil. This process can allow the hexadecane to reside in the PDMS for a few minutes, which is too short of a time to damage the PDMS device.

In another embodiment, the droplet-stabilizing surfactant can be eliminated by having a device in which there are no microwells, and where the protein droplets are separated in a microchannel by plugs of an oil. For a device that is fabricated in a polymer such as PDMS, an oil separating the protein droplets may dissolve into the bulk of the polymer device over time. This can cause the droplets to coalesce because the droplets are not stabilized by a surfactant. In some cases (e.g., if an oil that is insoluble in the polymer cannot be found and/or if coalescence of droplets is not desired), the microfluidic structure containing the protein channels can be made from glass, and the barriers and valves can be made in a polymer (e.g., PDMS). Because the volume of the barrier is less than the volume of oil, only a small fraction of the oil can dissolve into the barrier, causing the aqueous droplets to remain isolated.

The device described above (i.e., without microwells, and where the protein droplets are separated in a microchannel by plugs of oil) may be used to control the nucleation and growth of crystals similar to that of device 2010. For instance, a semi-permeable barrier can separate the microchannel from a reservoir, and fluids such as air, vapor, water, and saline can be flowed in the reservoir to induce diffusion of water across the barrier. Therefore, swelling and shrinking of the droplet, and the formation and growth of crystals within the droplet, can be controlled.

FIG. 18 shows another example of a device that can be used to enable a concentration-dependent chemical process (e.g., crystallization) to occur. Device 2500 includes a microwell 2130 fluidically connected to microchannel 2125. Beneath the microwell are reservoirs 2140 and 2141 (e.g., in the form of microchannels, which may be connected or independent), separated by semi-permeable barrier 2150. Droplet 2079 (e.g., an aqueous droplet) may be positioned in the microwell, surrounded by an immiscible fluid (e.g., an oil), as shown in FIG. 18C. In some cases, dialysis processes similar to ones described above can be implemented. For example, fluids can be transported across the semi-permeable barrier by various methods (e.g., diffusion or evaporation) to change the concentration and/or volume of the fluid in the droplet.

In other cases, a vapor diffusion process can occur in device 2500. For instance, a portion of the oil that is used as a carrier fluid in microchannel 2125 can be blown out of the channel with a fluid such as a gas (e.g., dry air or water saturated air) by flowing the gas into an inlet of the channel. This process can be performed while the droplet remains in the microwell (FIG. 18D). Depending on the chemical potential of the gas in the channel, the droplets containing protein can concentrate or dilute. For example, if air is flowed into microchannel 2125, water from the droplet can exchange (e.g., by evaporation) out of the droplet and into the air stream. This causes the droplet to shrink in volume (FIG. 18E). To dilute the protein in the droplet and/or to increase the volume of the droplet, a stream of saturated water vapor can be flowed into microchannel 2125 (FIG. 18F).

In another embodiment, concentration-dependent chemical processes can occur in a device without the use of droplets. For instance, a first fluid can be positioned in a region of the fluidic network (e.g., in a microwell) and a second fluid can be positioned in a reservoir, the region and the reservoir separated by a semi-permeable barrier. The introduction of different fluids into the reservoir can cause a change in the concentration of components within the first region, i.e., by diffusion of certain components across the semi-permeable barrier.

To overcome the "'world to chip' interface problem" of introducing a protein solution into a microfluidic device without wasting portions of the protein solution, e.g., in connections or during the initial purging of air from the microfluidic device, devices of the present invention can be fabricated with an on-chip injection-loop system. For example, buffer region 2022 of FIG. 9 with its neighboring valves (e.g., valves 2093 and 2100) can function as an injection-loop if it is located upstream from the nozzle (i.e., upstream of intersection 2075). A volume (e.g., 1 µL) of protein solution can first be dead-end loaded into a long channel (e.g., having dimensions 100 mm×0.1 mm×0.1 mm) and then isolated with valves. Next, the device can be primed and purged of air. Once droplets are being produced steadily, the injection-loop can be connected fluidically to the flow upstream from the nozzle by the actuation of valves.

In some embodiments, regions of a fluidic network such as microchannels and microwells are defined by voids in the structure. A structure can be fabricated of any material suitable for forming a fluidic network. Non-limiting examples of materials include polymers (e.g., polystyrene, polycarbonate, PDMS), glass, and silicon. Those of ordinary skill in the art can readily select a suitable material based upon e.g., its rigidity, its inertness to (i.e., freedom from degradation by) a fluid to be passed through it, its robustness at a temperature at which a particular device is to be used, its hydrophobicity/hydrophilicity, and/or its transparency/opacity to light (i.e., in the ultraviolet and visible regions).

In some instances, a device is comprised of a combination of two or more materials, such as the ones listed above. For instance, the channels of the device may be formed in a first material (e.g., PDMS), and a substrate can be formed in a second material (e.g., glass). In one particular example as shown in FIG. 8, structure 2135, which contains voids in the form of channels and microwells, can be made in PDMS, support layer 2136 can be made in PDMS, and support layer 2137 may be formed in glass.

Most fluid channels in components of the invention have maximum cross-sectional dimensions less than 2 mm, and in some cases, less than 1 mm. In one set of embodiments, all fluid channels containing embodiments of the invention are microfluidic or have a largest cross sectional dimension of no more than 2 mm or 1 mm. In another embodiment, the fluid channels may be formed in part by a single component (e.g., an etched substrate or molded unit). Of course, larger channels, tubes, chambers, reservoirs, etc. can be used to store fluids in bulk and to deliver fluids to components of the invention. In one set of embodiments, the maximum cross-sectional dimension of the channel(s) containing embodiments of the invention are less than 500 microns, less than 200 microns, less than 100 microns, less than 50 microns, or less than 25 microns. In some cases the dimensions of the channel may be chosen such that fluid is able to freely flow through the article or substrate. The dimensions of the channel may also be chosen, for example, to allow a certain volumetric or linear flowrate of fluid in the channel. Of course, the number of channels and the shape of the channels can be varied by any method known to those of ordinary skill in the art. In some cases, more than one channel or capillary may be used. For example, two or more channels may be used, where they are positioned inside each other, positioned adjacent to each other, positioned to intersect with each other, etc.

A "channel," as used herein, means a feature on or in an article (substrate) that at least partially directs the flow of a fluid. The channel can have any cross-sectional shape (circular, oval, triangular, irregular, square or rectangular, or the like) and can be covered or uncovered. In embodiments where it is completely covered, at least one portion of the channel can have a cross-section that is completely enclosed, or the entire channel may be completely enclosed along its entire length with the exception of its inlet(s) and outlet(s). A channel may also have an aspect ratio (length to average cross sectional dimension) of at least 2:1, more typically at least 3:1, 5:1, or 10:1 or more. An open channel generally will include characteristics that facilitate control over fluid transport, e.g., structural characteristics (an elongated indentation) and/or physical or chemical characteristics (hydrophobicity vs. hydrophilicity) or other characteristics that can exert a force (e.g., a containing force) on a fluid. The fluid within the channel may partially or completely fill the channel. In some cases where an open channel is used, the fluid may be held within the channel, for example, using surface tension (i.e., a concave or convex meniscus).

The channels of the device may be hydrophilic or hydrophobic in order to minimize the surface free energy at the interface between a material that flows within the channel and the walls of the channel. For instance, if the formation of aqueous droplets in an oil is desired, the walls of the channel can be made hydrophobic. If the formation of oil droplets in an aqueous fluid is desired, the walls of the channels can be made hydrophilic.

In some cases, the device is fabricated using rapid prototyping and soft lithography. For example, a high resolution laser printer may be used to generate a mask from a CAD file that represents the channels that make up the fluidic network. The mask may be a transparency that may be contacted with a photoresist, for example, SU-8 photoresist (MicroChem), to produce a negative master of the photoresist on a silicon wafer. A positive replica of PDMS may be made by molding the PDMS against the master, a technique known to those skilled in the art. To complete the fluidic network, a flat substrate, e.g., a glass slide, silicon wafer, or a polystyrene surface, may be placed against the PDMS surface and plasma bonded together, or may be fixed to the PDMS using an adhesive. To allow for the introduction and receiving of fluids to and from the network, holes (for example 1 millimeter in diameter) may be formed in the PDMS by using an appropriately sized needle. To allow the fluidic network to communicate with a fluid source, tubing, for example of polyethylene, may be sealed in communication with the holes to form a fluidic connection. To prevent leakage, the connection may be sealed with a sealant or adhesive such as epoxy glue.

In order to optimize a device of the present invention, it may be helpful to quantify the diffusion constant and solubility of certain fluids through the semi-permeable barrier, if these quantities are not already known. For instance, if the barrier is fabricated in PDMS, the flux of water through the barrier can be quantified by measuring transport rates of water as a function of barrier thickness. Microfluidic devices can be built to have a well-defined planar geometries for which analytical solutions to the diffusion equation are easily calculated. For example, a microfluidic device can be fabricated having a 2 mm by 2 mm square barrier separating a water-filled chamber from a chamber through which dry air flows. The flux can be measured by placing colloids in the water and measuring the velocity of the colloids as a function of time. Analysis of the transient and steady-state flux allows determination of the diffusion constant and solubility of water in PDMS. Similar devices can be used to measure the solubility of oil in PDMS. In order to optimize the reversible dialysis process, the flux of water into and out of the protein solutions in the droplets can be determined (e.g., as a function of droplet volume, ionic strength of the fluids in the reservoir and/or droplet, type of carrier oil, and/or thickness of the barrier) using video optical microscopy by measuring the volume of the droplets as a function of time after changing the solution in the reservoir.

The present invention is not limited by the types of proteins that can be crystallized. Examples of types of proteins include bacterially-expressed recombinant membrane channel proteins, G protein-coupled receptors heterologously expressed in a mammalian cell culture systems, membrane-bound ATPase, and membrane proteins.

Microfluidic methods have been used to screen conditions for protein crystallization, but until now this method has been applied mainly to easily handled water-soluble proteins. A current challenge in structural biology is the crystallization and structure determination of integral membrane proteins. These are water-insoluble proteins that reside in the cell membrane and control the flows of molecules into and out of the cell. They are primary molecular players in such central biological phenomena as the generation of electrical impulses in the nervous system, "cell signaling," i.e., the ability of cells to sense and respond to changes in environment, and the maintenance of organismal homeostasis parameters such as water and electrolyte balance, blood pressure, and cytoplasmic ATP levels. Despite their vast importance in maintaining cell function and viability, membrane proteins (which make up roughly 30% of proteins coded in the human genome) are under-represented in the structural database (which contains $>10^4$ water-soluble proteins and $<10^2$ membrane proteins). The reason for this scarcity is because it has been difficult to express membrane proteins in quantities large enough to permit crystallization trials, and even when such quantities are available, crystallization itself is not straight-forward.

Devices of the present invention may be used to exploit recent advances in membrane protein expression and crystallization strategies. For instance, some expression systems for prokaryotic homologues of neurobiologically important eukaryotic membrane proteins have been developed, and in a few cases these have been crystallized and structures determined by x-ray crystallography. In these cases, however, the rate-limiting step, is not the production of milligram-quantities of protein, but the screening of crystallization conditions. Membrane proteins must be crystallized from detergent solutions, and the choice and concentration of detergent have been found to be crucial additional parameters in finding conditions to form well-diffracting crystals. For this reason, a typical initial screen for a membrane protein requires systematic variation of 100-200 conditions. Sparse-matrix screens simply don't work because they are too sparse. Moreover, two additional constraints make the crystallization of membrane proteins more demanding than that of water-soluble proteins. First, the amounts of protein obtained in a typical membrane protein preparation, even in the best of cases, are much smaller than what is typically encountered in conventional water-soluble proteins (i.e., 1-10 mg rather than 50-500 mg). Second, membrane proteins are usually unstable in detergent and must be used in crystallization trials within hours of purification; they cannot be accumulated and stored. These constraints run directly against the requirement for large, systematic crystal screens.

Devices of the present invention may be used to overcome the constraints mentioned above for crystallizing membrane proteins. For example, device 2010, which can be used to perform reversible dialysis, may overcome the three limitations of membrane protein crystallization: the small amount of protein available, the short time available to handle the pure protein, and the very large number of conditions that must be tested to find suitable initial conditions for crystallization.

One of the challenges of crystallography is for the growth of extremely ordered and in some cases, large, crystals. Ordered and large crystals are suitable for ultra-high resolution data and for neutron diffraction data, respectively. These two methods are expected to provide the locations of protons, arguably the most important ions in enzymology, which are not accessible by conventional crystallography. So far, these applications have relied on serendipitous crystal formation rather than on controlled formation of crystals. Routine access of such ordered and/or large would make structural enzymology and its applications, e.g., drug design, more powerful than it is today. Certain embodiments of the current invention, with their ability to reversibly vary supersaturation, can be used to grow single crystals to large sizes, and the diffraction quality of these crystals can be characterized.

Although devices and methods of the present invention have been mainly described for crystallization, devices and methods of the invention may also be used for other types of concentration-dependent chemical processes. Non-limiting examples of such processes include chemical reactions, enzymatic reactions, immuno-based reactions (e.g., antigen-antibody), and cell-based reactions.

The following examples are intended to illustrate certain embodiments of the present invention, but are not to be construed as limiting and do not exemplify the full scope of the invention.

Example 1

This example illustrates a procedure for fabricating a microfluidic structure used in certain embodiments of the invention. In one embodiment, a microfluidic structure comprising a series of microfluidic channels and microwells was made by applying a standard molding article against an appropriate master. For example, microchannels were made in PDMS by casting PDMS prepolymer (Sylgard 184, Dow Corning) onto a patterned photoresist surface relief (a master) generated by photolithography. The pattern of photoresist comprised the channels and microwells having the desired dimensions. After curing for 2 h at 65° C. in an oven, the polymer was removed from the master to give a free-standing PDMS mold with microchannels and microwells embossed on its surface. Inlets and/or outlets were cut out through the thickness of the PDMS slab using a modified borer.

A semi-permeable membrane (15 microns thick) formed in PDMS and comprising a reservoir and valve, as illustrated in FIG. 8C, was fabricated via spin coating PDMS prepolymer onto a master generated by photolithography. The master comprised a pattern of photoresist comprising the reservoir and valve having the desired dimensions. The membrane layer was cured for 1 h at 65° C. in an oven.

Next, the PDMS mold and PDMS membrane layer were sealed together by placing both pieces in a plasma oxidation chamber and oxidizing them for 1 minute. The PDMS mold was then placed onto the membrane layer with the surface relief in contact with the membrane layer. A irreversible seal formed as a result of the formation of bridging siloxane bonds (Si—O—Si) between the two substrates, caused by a condensation reaction between silanol (SiOH) groups that are present at both surfaces after plasma oxidation. After sealing, the membrane layer (with the attached PDMS mold) was removed from the master. The resulting structure was then placed against a support layer of PDMS. This example illustrates that a microfluidic structure comprising microchannels, microwells, reservoirs, and valves can be fabricated using simple lithographic procedures according to one embodiment of the invention.

Example 2

Figure 10B:
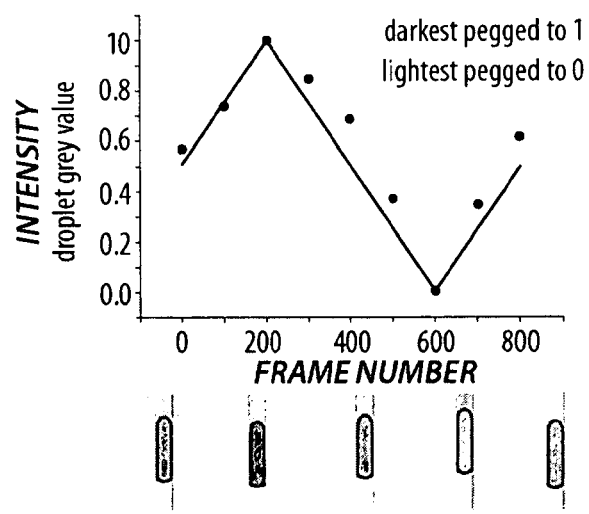
FIG. 10B shows a plot illustrating the combinatorial mixing of solutes in different droplets, according to another embodiment of the invention.

FIG. 10B shows the use of colloids to test combinatorial mixing of solutes and to visualize fluid flow using a microfluidic structure as generally illustrated in FIG. 9, which was made by the procedures generally described in Example 1. The colloid particles, 1 μm in size with a size variation of 2.3%, were made by Interfacial Dynamic Corporation. The concentration of the colloids was about 1%. The colloid suspension and buffer solution were flowed into inlets 2050 and 2060, respectively, using syringes connected to a syringe pump made by Harvard Apparatus, PHD2000 Programmable. The colloids were mixed with buffer by linearly varying the flow rates of the colloid suspension and buffer solution; for instance, the flow rate of the colloidal suspension was linearly and repeatedly varied from 80 μl/hr to 20 μl/hr while the flow rate of the buffer solution was linearly and repeatedly varied from 20 μl/hr to 80 μl/hr. This was performed so that the total flow rate of the aqueous suspension was kept constant at 100 μl/hr, and so that the drop size remained constant. The transmitted light intensity through the droplets was proportional to the colloid concentration. The transmitted light intensity was measured by estimating the gray scale of droplets shown in pictures taken by a high speed camera, Phantom V5. The pictures were taken at a rate of 10,000 frames per second. The gray scale estimation was performed using Image-J software. This experiment shows that combinatorial mixing of solutes can be used to generate many (e.g., 1000) different reaction conditions, each droplet being unique to a particular condition.

Example 3

This example shows the control of droplet size within microwells of a device. Experiments were performed using a microfluidic structure as generally illustrated in FIG. 13, which was made according to the procedures generally described in Example 1. All microwells were 200 μm wide and 30 μm in height, and the initial diameter of the droplets while the droplets were stored in the microwells was about 200 μm. Aqueous droplets comprised a 1M, NaCl solution. The droplets flowed in a moving carrier phase of PFD (perfluorodecalin, 97%, Sigma-Aldrich). All fluids were injected into device 2026 using syringe pumps (Harvard Apparatus, PHD2000 Programmable).

Device 2026 of FIG. 13 contained two sets of microwells for holding aqueous droplets. One set of microwells contained droplets of protein solution (droplets 2205-2208) that were separated from the reservoir by a 15 μm thick PDMS membrane that was permeable to water, but not to salt, PEG, or protein. Droplets in these microwells changed their volumes rapidly in contrast to droplets in microwells that were located 100 μm away from the reservoir (e.g., droplets 2201-2204). In FIG. 13, the process of fluid exchange between the reservoir and the microwells was diffusive, and diffusion time scales with the square of the distance. Thus, the time to diffuse 100 μm was 44 times longer than the time to diffuse 15 μm.

Initially, all the droplets in FIG. 13A were of the same size and volume. Dry air was circulated in the reservoir channel under a pressure of 15 psi, which caused the initially large droplets sitting above the reservoir to shrink substantially (i.e., droplets 2205-2208), while droplets stored in the outer wells (droplets 2201-2204) shrunk much less.

As shown in FIG. 13C, pure water was circulated in the reservoir channel under 15 psi pressure, which caused the initially small droplets to swell (i.e., droplets 2205-2208) because the droplets contained saline solution. In this fashion, all solute concentrations of the stored droplets was reversibly varied. The outer pair of droplets stored farther away from the reservoir channels (droplets 2201-2204) changed size much slower than the droplets stored directly above the reservoir channels (droplets 2205-2208) and approximated the initial droplet conditions.

Although water does dissolve slightly into the bulk of the PDMS microfluidic device and into the carrier oil, this experiment demonstrates that diffusion through the thin PDMS membrane is the dominant mechanism governing drop size, and not solubilization of the droplets in the carrier oil or in the bulk of the PDMS device.

Example 4

FIG. 14 shows use of the microfluidic structure generally illustrated in FIG. 8 to perform reversible microdialysis, particularly, for the crystallization and dissolving of the protein xylanase. The microfluidic structure was made according to the procedures generally described in Example 1. Solutions of xylanase (4.5 mg/mL, Hampton Research), NaCl (0.5 M, Sigma-Aldrich), and buffer (Na/K phosphate 0.17 M, pH 7) were introduced into inlets 2050, 2055, and 2060 and were combined as aqueous co-flows. Oil was introduced into inlets 2045 and 2065. All fluids were introduced into the device using syringe pumps (Harvard Apparatus, PHD2000 Programmable). Droplets of the combined solution were formed when the solution and the oil passed through a nozzle located at intersection 2075. One hundred identical droplets, each having a volume of 2 nL, were stored in microwells of device 2010.

Device 2010 comprised two layers. The upper layer comprised flow channels and microwells which contained the droplets of protein. The lower layer comprised five independent dialysis reservoirs and valves that controlled flow in the protein-containing channels of the upper layer. The two layers were separated by a 15 µm thick semi-permeable barrier 2150 made in PDMS. Square posts 2145 of PDMS covered 25% of the reservoir support the barrier. FIG. 15B is a photograph of device 2010 showing microwells 2130 and square posts 2145 that supported barrier 2150.

Crystallization occurred when dry air was introduced into the reservoir (i.e., at a pressure of 15 psi), which caused water to flow from the protein solution across the barrier and into the reservoir. Once nucleated, the crystals grew to their final size in under 10 seconds. Over 90% of the wells were observed to contain crystals. Next, air in the reservoir was replaced with distilled water (i.e., pressurized at 15 psi). Diffusion of water into the droplet caused the volume of mother liquor surrounding the crystals to increase immediately (FIG. 15C). After 15 minutes, the crystals began to dissolve rapidly and disappeared in another minute. These experiments demonstrate the feasibility of using a microfluidic device of the present invention to crystallize proteins using nanoliter volumes of sample, and the ability of these devices to perform reversible dialysis.

Example 5

FIG. 16A is a diagram showing the energy required for nucleating a crystal. Specifically, FIG. 16A relates free energy of a spherical crystal nucleus ($\Delta G$) to the size of the crystal nucleus (r). Nucleation is an activated process because a crystal of small size costs energy to form due to the liquid-crystal surface energy ($\gamma$). The free energy of a spherical crystal nucleus of radius r is $\Delta G = \gamma 4\pi r^2 - \Delta\mu 4\pi r^3/3$. The height of the nucleation barrier ($\Delta G^*$) and critical nucleus ($r^*$) decrease as the chemical potential difference ($\Delta\mu$) between the crystal and liquid phases increases. A highly supersaturated solution (i.e., large $\Delta\mu$) will have a high nucleation rate, $\Gamma \sim \exp(-\Delta G^*/kT)$ and crystals, once nucleated, will grow rapidly.

Example 6

The following example is a prophetic example. FIG. 17 is a schematic diagram of a typical protein phase diagram showing the relationship between precipitation concentration and protein concentration in a droplet. Experiments will be performed in the device of FIG. 15. Initially, sets of droplets in wells over each of the five reservoirs (e.g., reservoirs 2140-1, 2140-2, 2140-3, 2140-4, and 2140-5 of FIG. 15A) will contain protein solutions of different compositions (triangles). The reservoirs' precipitant concentrations are indicated as horizontal dashed lines. Each protein solution (triangles) can equilibrate with its associated reservoir through the exchange of water between the reservoir and protein solutions. The state of the five sets of protein solutions after equilibration are shown as follows: Solutions remain soluble (open circles); solutions enter two-phase region (filled circles) and phase separate into crystals; and entire solution becomes crystalline (squares). This experiment will demonstrate that entire phase diagrams can be obtained using a single microfluidic device of the present invention.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of", when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method, comprising:
   providing a microfluidic network comprising a plurality of regions and a microfluidic channel in fluid communication with the plurality of regions;
   flowing an oil in the microfluidic channel;
   flowing a first plurality of aqueous droplets into the microfluidic channel through an inlet;
   positioning each of the plurality of aqueous droplets in a plurality of separate regions;
   maintaining the plurality of aqueous droplets in the separate regions while the oil is flowing in the microfluidic channel; and
   removing the plurality of aqueous droplets positioned in the separate regions; wherein the aqueous droplets are removed in the order that they flowed into the microfluidic channel.

2. A method as in claim 1, wherein the oil or the first fluid do not comprise a surfactant.

3. A method as in claim 1, wherein a first portion of the plurality of droplets comprises a first aqueous fluid and a second portion of the plurality of droplets comprises a second fluid.

4. A method as in claim 3, wherein the second fluid does not comprise a surfactant.

5. A method as in claim 3, wherein the first and second portions of aqueous droplets do not come into physical contact with each other during the positioning or maintaining steps.

6. A method as in claim 1, wherein positioning or maintaining a first aqueous droplet in a first region is independent of flow rate of the oil in the microfluidic channel.

7. A method as in claim 1, wherein a first region is closer in distance to the inlet than a second region.

8. A method as in claim 7, wherein a first aqueous droplet is positioned in the first region before a second droplet is positioned in the second region.

9. A method as in claim 8, further comprising removing the first aqueous droplet from the first region and then removing the second aqueous droplet from the second region.

10. A method as in claim 8, comprising flowing a fluid comprising a surfactant in the microfluidic channel.

11. A method as in claim 8, comprising coating the first or second aqueous droplet with a surfactant.

12. A method as in claim 8, comprising dewetting the first or second aqueous droplet from a surface of the microfluidic channel.

13. A method as in claim 8, wherein positioning of the first aqueous droplet in the first region affects a direction of flow of the second aqueous droplet in the microfluidic network.

14. A method as in claim 1, wherein the microfluidic channel comprises an upstream portion, a downstream portion, and first and second fluid paths, at least one fluid path branching from the upstream portion and reconnecting at the downstream portion.

15. A method as in claim 14, wherein the first and second fluid paths have different resistances to flow.

16. A method as in claim 15, wherein the first fluid path comprises a fluid constriction.

17. A method as in claim 16, wherein a first region is positioned within the first fluid path.

18. A method as in claim 16, wherein the first fluid path has less resistance to flow compared to the second fluid path prior to positioning of the first aqueous droplet in the first region, and the first fluid path has greater resistance to flow after positioning of the first aqueous droplet in the first region.

19. A method as in claim 1, wherein a first region comprises a cross-sectional area approximately the same as a cross-sectional area of the microfluidic channel in fluid communication with the first region.

20. The method of claim 1, wherein the microfluidic channel has a maximum cross sectional dimension of 500 microns or smaller.

21. The method of claim 20, wherein the microfluidic channel has a maximum cross sectional dimension of 100 microns or smaller.

22. The method of claim 1, wherein the first aqueous droplet has a volume of less than 1 nL.

23. The method of claim 1, wherein the oil is a fluorinated oil.

24. A method, comprising:
providing a microfluidic network comprising at least a first inlet to a microfluidic channel, a first and a second region for positioning a first and a second aqueous droplet, respectively, the first and second regions in fluid communication with the microfluidic channel, wherein the first region is closer in distance to the first inlet than the second region;

flowing an oil in the microfluidic channel;

flowing the first aqueous droplet in the microfluidic channel through the first inlet;

positioning the first aqueous droplet in the first region;

flowing the second droplet in the microfluidic channel through the first inlet and past the first region without the second aqueous droplet physically contacting the first aqueous droplet;

positioning the second aqueous droplet in the second region;

flowing the first aqueous droplet from the first region toward the first inlet; and flowing the second droplet from the second region past the first region and toward the first inlet without the second aqueous droplet physically contacting the first aqueous droplet, wherein the first and second droplets leave the first inlet in the order in which they entered.

25. The method of claim 24, wherein positioning the first droplet in the first region does not require the use of a surfactant in the oil or the first droplet.

* * * * *